United States Patent
Varkey et al.

(10) Patent No.: US 9,528,162 B2
(45) Date of Patent: Dec. 27, 2016

(54) SEQUENCES AND THEIR USE FOR DETECTION AND CHARACTERIZATION OF STEC BACTERIA

(71) Applicant: E. I. du Pont de Nemours and Company, Wilmington, DE (US)

(72) Inventors: Stephen Varkey, Newark, DE (US); Daniel R. DeMarco, Wilmington, DE (US); Mark A. Jensen, West Chester, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 316 days.

(21) Appl. No.: 14/326,020

(22) Filed: Jul. 8, 2014

(65) Prior Publication Data

US 2014/0323710 A1    Oct. 30, 2014

Related U.S. Application Data

(62) Division of application No. 13/630,045, filed on Sep. 28, 2012, now Pat. No. 8,802,371.

(60) Provisional application No. 61/540,119, filed on Sep. 28, 2011.

(51) Int. Cl.
  *C12P 19/34*   (2006.01)
  *C12Q 1/68*   (2006.01)

(52) U.S. Cl.
  CPC ..................... *C12Q 1/689* (2013.01)

(58) Field of Classification Search
  USPC ................................ 435/6.12, 91.2
  See application file for complete search history.

(56) References Cited

U.S. PATENT DOCUMENTS

| | | | |
|---|---|---|---|
| 4,678,812 | A | 7/1987 | Bollin et al. |
| 4,683,195 | A | 7/1987 | Mullis et al. |
| 4,683,202 | A | 7/1987 | Mullis |
| 4,762,857 | A | 8/1988 | Bollin et al. |
| 5,210,015 | A | 5/1993 | Gelfand et al. |
| 5,487,972 | A | 1/1996 | Gelfand et al. |
| 5,538,848 | A | 7/1996 | Livak et al. |
| 5,804,375 | A | 9/1998 | Gelfand et al. |
| 5,994,056 | A | 11/1999 | Higuchi et al. |
| 6,171,785 | B1 | 1/2001 | Higuchi et al. |
| 6,312,930 | B1 | 11/2001 | Tice et al. |
| 6,326,145 | B1 | 12/2001 | Whitcombe et al. |
| 2011/0020823 | A1 | 1/2011 | Burns |

FOREIGN PATENT DOCUMENTS

| | | |
|---|---|---|
| EP | 2292799 | 3/2011 |
| WO | 9711197 | 3/1997 |
| WO | 9848046 | 10/1998 |
| WO | 0066777 | 9/2000 |
| WO | 2005005659 | 1/2005 |

OTHER PUBLICATIONS

Tabor, et al., A Bacteriophage T7 RNA Polymerase/Promoter System for Controlled Exclusive Expression of Specific Genes: Proc. Nat'l. Acad. Sci. U.S.A. 82: 1074-1078 (1985).
International Search Report for International Patent Application No. PCTUS2012/057795, 2013.
Written Opinion of the International Searching Authority for International Patent Application No. PCTUS2012/057795, 2013.
International Preliminary Report on Patentability Chapter I for International Patent Application No. PCTUS2012/057795, 2014.
Communication from European Patent Office Examining Division for EP Patent Application No. 12772181.9; May 8, 2014.
J. Madic et al, "Simplex and Multiplex Real-Time PCR Assays for the Detection of Flagellar (H-antigen) Flic Alleles and Intimin (eae) Variants Associated with Enterohaemorrhagic *Escherichia coli* (EHEC) Serotypes 026:h11, 0103:h2, 0111:h8, 0145:H28 and 0157:H7" Journal of Applied Microbiology, vol. 109, Jul. 1, 2010, pp. 1696-1705, XP055048359, ISSN: 1364-5072, DOI: 10.111/j.1365-2672.2010.04798.x abstract: table 1: "Materials and Methods".
Siya Ram, "Computing TaqMan Probes for Multiplex PCR Detection of *E. Coli* 0157 Serotypes in Water", in SILICO Biology, vol. 5, Jan. 1, 2005, pp. 499-504, XP055048360, table 3.
Ching-Fang Hsu, "Use of the Duplex TaqMan PCR System for Detection of Shiga-Like Toxin-Producing *Escherichia coli* 0157", Journal of Clinical Microbiology, vol. 43, No. 6, Jan. 1, 2005, pp. 2668-2673, XP055048361, DOI: 10.1128/JCM.43.6.2668-2673. 2005 p. 2669, last paragraph; abstract.
Singh Jitender et al, "A Scorpion Probe-Based Real-Time PCR Assay for Detection of *E. coli* 0157:H7 in Dairy Products", Foodborne Pathogens and Disease, Mary Ann Liebert, Inc., Publishers, US, vol. 6, No. 3, Apr. 1, 2009, pp. 395-400, XP002603978, ISSN: 1535-3141, DOI: 10.1089/FPD.2008.0178 [retrieved on Mar. 9, 2009] abstract; p. 396, col. 2.
Chinese Patent Application No. 201280047286 Office Action dated Jan. 6, 2015.

*Primary Examiner* — Kenneth Horlick

(57) ABSTRACT

This invention relates to a rapid method for detection and characterization of STEC bacteria based on the presence of nucleic acid sequences, in particular, to a PCR-based method for detection, and to oligonucleotide molecules and reagents and kits useful therefore. This method is preferably employed to detect STEC bacteria in a food or water sample, such as a beef enrichment. The present invention further relates to isolated polynucleotides, replication compositions, kits, and reagent tablets for carrying out the method of the present invention.

3 Claims, No Drawings

SEQUENCES AND THEIR USE FOR DETECTION AND CHARACTERIZATION OF STEC BACTERIA

This application is a divisional of U.S. patent application Ser. No. 13/630,045, filed Sep. 28, 2012, now U.S. Pat. No. 8,802,371, which claims the benefit of U.S. Provisional Application 61/540,119 filed Sep. 28, 2011.

FIELD OF INVENTION

This invention relates to methods for detection and characterization of Shiga toxin producing *Escherichia coli* (STEC) bacteria based on the presence of nucleic acid sequences, preferably PCR-based methods for detection, and to oligonucleotide molecules and reagents and kits useful therefor.

BACKGROUND OF INVENTION

*Escherichia coli* (*E. coli*) is a gram-negative, rod-shaped bacterium. Although most strains of *E. coli* are benign and are found as normal intestinal flora of humans and other animals, some strains are pathogenic and can lead to disease. Different strains of pathogenic *E. coli* differ in their epidemiology, clinical course and potential for causing outbreaks of disease.

Shiga toxin producing *Escherichia coli* (STEC) is a type of enterohemorrhagic bacteria that can cause mild to severe intestinal disease, kidney problems, and even central nervous system effects. The pathogenicity of these bacterial strains is due, in large part, to their production of Shiga-like toxins Stx1 and Stx2. Additionally, production of the intimin adherence protein encoded by the eae gene has been linked to pathogenicity of bacteria, as has possession of certain surface antigens, including the O26, O111, O121, O45, O103, and O145 antigens.

One well-known serotype of STEC bacteria is *E. coli* serotype O157:H7, which has been associated with several food and water borne outbreaks. This bacterial serotype is regulated as an adulterant in ground beef by the U.S. Department of Agriculture (USDA) with a zero tolerance standard. Because of its tight regulation, numerous tests for *E. coli* O157:H7 exist in the market. However, numerous other STEC bacteria strains also can cause disease, making detection of other STEC bacterial serotypes, or STEC bacteria in general, important for improved food safety.

It is desirable, therefore, to have a test for the accurate detection and characterization of STEC bacteria in a sample.

SUMMARY OF INVENTION

One aspect of the present invention is a method for detecting the presence of STEC bacteria in a sample, said sample comprising nucleic acids, said method comprising:
(a) providing a reaction mixture comprising suitable primer pairs for amplification of at least a portion of one or more of the eae gene, the Stx1A gene, and the Stx2A gene;
(b) performing PCR amplification of said nucleic acids of said sample using the reaction mixture of step (a); and
(c) detecting the amplification of step (b).

In certain examples, the invention relates to a method for detecting the presence of STEC bacteria in a sample, said sample comprising nucleic acids, said method comprising
(a) providing a reaction mixture comprising a first primer, a second primer, and a probe for amplification and detection of at least a portion of SEQ ID NO: 688 (eae); wherein each of said first primer, second primer, and probe comprises a 5' end and a 3' end; wherein said first primer comprises at least 15 contiguous nucleotides of SEQ ID NO: 145 or a sequence complementary thereto; and wherein said probe comprises at least 15 contiguous nucleotides of SEQ ID NO: 160 or a sequence complementary thereto;
(b) performing PCR amplification of said nucleic acids of said sample using the reaction mixture of step (a); and
(c) detecting the amplification of step (b).

In certain embodiments, the second primer comprises a nucleic acid sequence comprising at least 15 contiguous nucleotides of SEQ ID NO: 191 or a sequence complementary thereto. In further embodiments, the first primer comprises a sequence selected from the group consisting of SEQ ID NOs: 146-159, the second primer comprises a sequence selected from the group consisting of SEQ ID NOs: 192-205, and the probe comprises a sequence selected from the group consisting of SEQ ID NOs: 161-175. In additional embodiments, the 3' end of the probe is directly or indirectly attached to the 5' end of said the primer forming a primer-probe complex. In still further embodiments, the primer-probe complex can be detectably labeled. In additional embodiments, the reaction mixture further comprises a quencher oligonucleotide comprising at least 15 contiguous nucleotides of SEQ ID NO: 176. In some embodiments, the sample comprises a food sample or a water sample.

In other examples, the invention relates to a method for detecting the presence of STEC bacteria in a sample, said sample comprising nucleic acids, said method comprising
(a) providing a reaction mixture comprising a first primer, a second primer, and a probe for amplification and detection of at least a portion of SEQ ID NO: 686 (Stx1A); wherein each of said first primer, second primer, and probe comprises a 5' end and a 3' end; and wherein said first primer and probe are selected from the group consisting of:
(I) a first primer comprising at least 15 contiguous nucleotides of SEQ ID NO: 1 or a sequence complementary thereto and a probe comprising at least 15 contiguous nucleotides of SEQ ID NO: 16 or a sequence complementary thereto;
(II) a first primer comprising at least 15 contiguous nucleotides of SEQ ID NO: 1 or a sequence complementary thereto and a probe comprising at least 15 contiguous nucleotides of SEQ ID NO: 49 or a sequence complementary thereto; and
(III) a first primer comprising SEQ ID NO: 55 or a sequence complementary thereto and probe comprising SEQ ID NO: 56 or a sequence complementary thereto;
(b) performing PCR amplification of said nucleic acids of said sample using the reaction mixture of step (a); and
(c) detecting the amplification of step (b).

In certain embodiments, the second primer comprises a nucleic acid sequence comprising at least 15 contiguous nucleotides of SEQ ID NO: 58 or comprising SEQ ID NO: 73. In other embodiments, the first primer comprises a sequence selected from the group consisting of SEQ ID NOs: 2-15, 48; the second primer comprises a sequence selected from the group consisting of SEQ ID NOs: 59-72; and the probe comprises a sequence selected from the group consisting of SEQ ID NOs: 17-30, 49-52. In further embodiments, the 3' end of the probe is directly or indirectly attached to the 5' end of the first primer forming a primer-probe complex. In still further embodiments, the primer-probe complex can be detectably labeled. In additional embodiments, the reaction mixture further comprises a quencher oligonucleotide comprising SEQ ID NO: 53, 54, or 57, or comprising at least 15 contiguous nucleotides of SEQ ID NO: 31. In some embodiments, the sample comprises a food sample or a water sample.

In still further examples, the present invention relates to a method for detecting the presence of STEC bacteria in a sample, said sample comprising nucleic acids, said method comprising (a) providing a reaction mixture comprising a first primer, a second primer, and a probe for amplification and detection of at least a portion of SEQ ID NO: 687 (Stx2A); wherein each of said first primer, second primer, and probe comprises a 5' end and a 3' end; and wherein said first primer and probe are selected from the group consisting of:
  (I) a first primer comprising at least 15 contiguous nucleotides of SEQ ID NO: 74 or a sequence complementary thereto and a probe comprising at least 15 contiguous nucleotides of SEQ ID NO: 89 or a sequence complementary thereto;
  (II) a first primer comprising SEQ ID NO: 120 or a sequence complementary thereto and a probe comprising SEQ ID NO: 121 or 122 or a sequence complementary thereto; and
  (III) a first primer comprising SEQ ID NO: 125 or a sequence complementary thereto and probe comprising SEQ ID NO: 126 or a sequence complementary thereto;
(b) performing PCR amplification of said nucleic acids of said sample using the reaction mixture of step (a); and
(c) detecting the amplification of step (b).

In certain embodiments, the second primer comprises a nucleic acid sequence comprising at least 15 contiguous nucleotides of SEQ ID NO: 128 or comprising SEQ ID NO: 143 or 144. In other embodiments, the first primer comprises a sequence selected from the group consisting of SEQ ID NOs: 75-88; the second primer comprises a sequence selected from the group consisting of SEQ ID NOs: 129-144; and the probe comprises a sequence selected from the group consisting of SEQ ID NOs: 90-104. In additional embodiments, the 3' end of the probe is directly or indirectly attached to the 5' end of said first primer forming a primer-probe complex. In still further embodiments, the primer-probe complex can be detectably labeled. In additional embodiments, the reaction mixture further comprises a quencher oligonucleotide comprising SEQ ID NO: 123, 124, or 127, or comprising at least 15 contiguous nucleotides of SEQ ID NO: 105. In some embodiments, the sample comprises a food sample or a water sample.

In a further aspect, the invention relates to an isolated polynucleotide comprising a primer-probe complex, wherein said primer probe complex comprises:
(A) a primer region comprising a nucleic acid sequence comprising at least 15 contiguous nucleotides of SEQ ID NO: 1 and a probe region comprising at least 15 contiguous nucleotides of SEQ ID NO: 16;
(B) a primer region comprising SEQ ID NO: 48 and a probe region comprising a nucleic acid sequence selected from the group consisting of SEQ ID NOs: 49-52;
(C) a primer region comprising SEQ ID NO: 55, and a probe region comprising SEQ ID NO: 56;
(D) a primer region comprising at least 15 contiguous nucleotides of SEQ ID NO: 74 and a probe region comprising at least 15 contiguous nucleotides of SEQ ID NO: 89;
(E) a primer region comprising SEQ ID NO: 120 and a probe region comprising a nucleic acid sequence selected from the group consisting of SEQ ID NOs: 121-122;
(F) a primer region comprising SEQ ID NO: 125 and a probe region comprising SEQ ID NO: 126; and
(G) a primer region comprising at least 15 contiguous nucleotides of SEQ ID NO: 145 and a probe region comprising at least 15 contiguous nucleotides of SEQ ID NO: 160;
wherein said probe region and said primer region each have a 5' and 3' terminus, wherein said 3' terminus of said probe region is attached to said 5' terminus of said primer region via a linker moiety, and wherein said primer-probe complex further comprises a detectable label.

In a further aspect, the invention relates to kits and reagent tablets for detection of STEC bacteria in a sample, comprising an isolated polynucleotide of the present invention.

A further aspect of the present invention is a method for detecting the presence of STEC bacteria in a sample, said sample comprising nucleic acids, said method comprising:
(a) providing a reaction mixture comprising suitable primer pairs for amplification of at least a portion of:
  (i) the eae gene; and
  (ii) one or more of the Stx1A and Stx2A genes; and
(b) performing PCR amplification of said nucleic acids of said sample using the reaction mixture of step (a); and
(c) detecting the amplification of step (b).

In certain examples, amplification of a portion of the eae gene comprises amplification of at least a portion of SEQ ID NO: 688. In other examples, amplification of a portion one or more of the Stx1A and Stx2A genes comprises amplification of at least a portion of one or both of SEQ ID NOs: 686 and 687. In certain embodiments, the reaction mixture comprises suitable primer pairs for amplification of at least a portion of all three of SEQ ID NOs: 686-688.

In additional embodiments, the reaction mixture further comprises suitable primer pairs for amplification of at least a portion of one or more of the genes encoding the O26, O111, O121, O45, O103, O145, and O157 surface antigens. In certain examples, such amplification comprises amplification of one or more nucleic acid sequences selected from the group consisting of SEQ ID NOs: 689-696.

In certain examples, a suitable primer pair for amplification of SEQ ID NO: 686 comprises (A) a first primer comprising a nucleic acid sequence selected from the group consisting of SEQ ID NOs: 1-15 and 48, and a second primer comprising a nucleic acid sequence selected from the group consisting of SEQ ID NOs: 58-72; or (B) a first primer comprising SEQ ID NO: 55 and a second primer comprising SEQ ID NO: 73. In additional examples, the reaction mixture further comprises a probe, wherein: (I) where said first primer is selected from SEQ ID NOs: 1-15, said probe comprises a nucleic acid sequence selected from the group consisting of SEQ ID NOs: 31-47; (II) where said first primer comprises SEQ ID NO: 48, said probe comprises a nucleic acid sequence selected from the group consisting of SEQ ID NOs: 49-52; and (III) where said first primer comprises SEQ ID NO: 55, said probe comprises SEQ ID NO: 56. In further examples, the 3' end of the probe is attached to the 5' end of the primer forming a primer-probe complex. In still further examples, the primer-probe complex is detectably labeled. In additional examples, the reaction mixture further comprises a quencher oligonucleotide comprising a nucleic acid sequence selected from the group consisting of SEQ ID NOs: 31-47, 53-54, and 57.

In certain examples, a suitable primer pair for amplification of SEQ ID NO: 687 comprises: (A) a first primer comprising a nucleic acid sequence selected from the group consisting of SEQ ID NOs: 74-88, and a second primer comprising a nucleic acid sequence selected from the group consisting of SEQ ID NOs: 128-142; (B) a first primer comprising SEQ ID NO: 120 and a second primer comprising SEQ ID NO: 143; or (C) a first primer comprising SEQ ID NO: 125 and a second primer comprising SEQ ID NO: 144. In additional examples, the reaction mixture further comprises a probe, wherein: (I) where said first primer is selected from SEQ ID NOs: 74-88, said probe comprises a nucleic acid sequence selected from the group consisting of SEQ ID NOs: 89-104; (II) where said first primer comprises SEQ ID NO: 120, said probe comprises a nucleic acid sequence selected from the group consisting of SEQ ID NOs: 121-122; and (III) where said first primer comprises SEQ ID NO: 125, said probe comprises SEQ ID NO: 126. In further examples, the 3' end of the probe is attached to the 5' end of the primer forming a primer-probe complex. In still further examples, the primer-probe complex is detectably labeled. In additional examples, the reaction mixture further comprises a quencher oligonucleotide comprising a nucleic acid sequence selected from the group consisting of SEQ ID NOs: 105-119, 123-124, and 127.

In certain examples, a said suitable primer pair for amplification of SEQ ID NO: 688 comprises a first primer comprising a nucleic acid sequence selected from the group consisting of SEQ ID NOs: 145-159, and a second primer comprising a nucleic acid sequence selected from the group consisting of SEQ ID NOs: 191-205. In additional examples, the reaction mixture further comprises a probe, wherein the probe comprises a nucleic acid sequence selected from the group consisting of SEQ ID NOs: 160-175. In further examples, the 3' end of the probe is attached to the 5' end of the primer forming a primer-probe complex. In still further examples, the primer-probe complex is detectably labeled. In additional examples, the reaction mixture further comprises a quencher oligonucleotide comprising a nucleic acid sequence selected from the group consisting of SEQ ID NOs: 176-190.

In certain examples, a suitable primer pair for amplification of SEQ ID NO: 689 comprises: (A) a first primer comprising a nucleic acid sequence selected from the group consisting of SEQ ID NOs: 206-220, and a second primer comprising a nucleic acid sequence selected from the group consisting of SEQ ID NOs: 258-272; (B) a first primer comprising SEQ ID NO: 251, and a second primer comprising SEQ ID NO: 273; or (C) a first primer comprising SEQ ID NO: 255, and a second primer comprising SEQ ID NO: 274. In additional examples, the reaction mixture further comprises a probe, wherein the probe comprises: (I) where said first primer is selected from SEQ ID NOs: 206-220, said probe comprises a nucleic acid sequence selected from the group consisting of SEQ ID NOs: 221-235; (II) where said first primer comprises SEQ ID NO: 251, said probe comprises a nucleic acid sequence selected from the group consisting of SEQ ID NOs: 252-253; and (III) where said first primer comprises SEQ ID NO: 255, said probe comprises SEQ ID NO: 256. In further examples, the 3' end of the probe is attached to the 5' end of the primer forming a primer-probe complex. In still further examples, the primer-probe complex is detectably labeled. In additional examples, the reaction mixture further comprises a quencher oligonucleotide comprising a nucleic acid sequence selected from the group consisting of SEQ ID NOs: 236-250, 254, and 257.

In certain examples, a suitable primer pair for amplification of SEQ ID NO: 690 comprises a first primer comprising a nucleic acid sequence selected from the group consisting of SEQ ID NOs: 275-289 and 324, and a second primer comprising a nucleic acid sequence selected from the group consisting of SEQ ID NOs:327-341. In additional examples, the reaction mixture further comprises a probe, wherein the probe comprises: (I) where said first primer is selected from SEQ ID NOs: 275-289, said probe comprises a nucleic acid sequence selected from the group consisting of SEQ ID NOs: 290-306; and (II) where said first primer comprises SEQ ID NO: 324, said probe comprises SEQ ID NO: 325. In further examples, the 3' end of the probe is attached to the 5' end of the primer forming a primer-probe complex. In still further examples. the primer-probe complex is detectably labeled. In additional examples, the reaction mixture further comprises a quencher oligonucleotide comprising a nucleic acid sequence selected from the group consisting of SEQ ID NOs: 307-323 and 326.

In certain examples, a suitable primer pair for amplification of SEQ ID NO: 691 comprises a first primer comprising a nucleic acid sequence selected from the group consisting of SEQ ID NOs: 342-356, and a second primer comprising a nucleic acid sequence selected from the group consisting of SEQ ID NOs: 393-407. In additional examples, the reaction mixture further comprises a probe, wherein said probe comprises a nucleic acid sequence selected from the group consisting of SEQ ID NOs: 357-374. In further examples, the 3' end of the probe is attached to the 5' end of the primer forming a primer-probe complex. In still further examples, the primer-probe complex is detectably labeled. In additional examples, the reaction mixture further comprises a quencher oligonucleotide comprising a nucleic acid sequence selected from the group consisting of SEQ ID NOs: 375-392.

In certain examples, a suitable primer pair for amplification of SEQ ID NO: 692 comprises: (A) a first primer comprising SEQ ID NO: 456, and a second primer comprising SEQ ID NO: 480; (B) a first primer comprising SEQ ID NO: 459, and a second primer comprising SEQ ID NO: 481; or (C) a first primer comprising SEQ ID NO: 462, and a second primer comprising SEQ ID NO: 482. In additional examples, the reaction mixture further comprises a probe, wherein said probe comprises: (I) where said first primer comprises SEQ ID NO: 456, said probe comprises SEQ ID NO: 457; (II) where said first primer comprises SEQ ID NO: 459, said probe comprises of SEQ ID NO: 460; and (III) where said first primer comprises SEQ ID NO: 462, said probe comprises SEQ ID NO: 463. In further examples, the 3' end of the probe is attached to the 5' end of the primer forming a primer-probe complex. In still further examples, the primer-probe complex is detectably labeled. In additional examples, the reaction mixture further comprises a quencher oligonucleotide comprising a nucleic acid sequence selected from the group consisting of SEQ ID NOs: 458, 461, and 464.

In certain examples, a said suitable primer pair for amplification of SEQ ID NO: 693 comprises a first primer comprising a nucleic acid sequence selected from the group consisting of SEQ ID NOs: 408-423, and a second primer comprising a nucleic acid sequence selected from the group consisting of SEQ ID NOs: 465-479. In additional examples, the reaction mixture further comprises a probe, wherein said probe comprises a nucleic acid sequence selected from the group consisting of SEQ ID NOs: 424-439. In further examples, the 3' end of the probe is attached to the 5' end of the primer forming a primer-probe complex. In still further examples, the primer-probe complex is detectably labeled. In additional examples, the reaction mixture further comprises a quencher oligonucleotide comprising a nucleic acid sequence selected from the group consisting of SEQ ID NOs: 440-455.

In certain examples, a suitable primer pair for amplification of SEQ ID NO: 694 comprises: (A) a first primer comprising a nucleic acid sequence selected from the group consisting of SEQ ID NOs: 483-497 and 537, and a second primer comprising a nucleic acid sequence selected from the group consisting of SEQ ID NOs: 540-554; (B) a first primer comprising SEQ ID NO: 528, and a second primer comprising SEQ ID NO: 555; (C) a first primer comprising SEQ ID NO: 531, and a second primer comprising SEQ ID NO: 556; or (D) a first primer comprising SEQ ID NO: 534, and a second primer comprising SEQ ID NO: 557. In additional examples, the reaction mixture further comprises a probe, wherein said probe comprises: (I) where said first primer is selected from SEQ ID NOs: 483-497, said probe comprises a nucleic acid sequence selected from the group consisting of SEQ ID NOs: 498-512; (II) where said first primer comprises SEQ ID NO: 528, said probe comprises SEQ ID NO: 529; (III) where said first primer comprises SEQ ID NO: 531, said probe comprises SEQ ID NO: 532; (IV) where said first primer comprises SEQ ID NO: 534, said probe comprises SEQ ID NO: 535; (V) where said first primer comprises SEQ ID NO: 537, said probe comprises SEQ ID NO: 538. In further examples, the 3' end of the probe is attached to the 5' end of the primer forming a primer-probe complex. In still further examples, the primer-probe complex is detectably labeled. In additional examples, the reaction mixture further comprises a quencher oligonucleotide comprising a nucleic acid sequence selected from the group consisting of SEQ ID NOs: 513-527, 530, 533, 536, and 539.

In certain examples, a suitable primer pair for amplification of SEQ ID NO: 695 comprises a first primer comprising a nucleic acid sequence selected from the group consisting of SEQ ID NOs: 558-572, and a second primer comprising a nucleic acid sequence selected from the group consisting of SEQ ID NOs: 603-617. In additional examples, the reaction mixture further comprises a probe, wherein said probe comprises a nucleic acid sequence selected from the group consisting of SEQ ID NOs: 573-587. In further examples, the 3' end of said probe is attached to the 5' end of said primer forming a primer-probe complex. In still further examples, the primer-probe complex is detectably labeled. In additional examples, the reaction mixture further comprises a quencher oligonucleotide comprising a nucleic acid sequence selected from the group consisting of SEQ ID NOs: 588-602.

In certain examples, a said suitable primer pair for amplification of SEQ ID NO: 696 comprises a first primer comprising a nucleic acid sequence selected from the group consisting of SEQ ID NOs: 618-633, and a second primer comprising a nucleic acid sequence selected from the group consisting of SEQ ID NOs: 671-685. In additional examples, the reaction mixture further comprises a probe, wherein said probe comprises a nucleic acid sequence selected from the group consisting of SEQ ID NOs: 634-653. In further examples, the 3' end of said probe is attached to the 5' end of said primer forming a primer-probe complex. In still further examples, the primer-probe complex is detectably labeled. In additional examples, the reaction mixture further comprises a quencher oligonucleotide comprising a nucleic acid sequence selected from the group consisting of SEQ ID NOs: 654-670.

In one particular embodiment:
(A) a suitable primer pair for amplification of SEQ ID NO: 686 comprises
  (I) a first primer comprising a nucleic acid sequence selected from the group consisting of SEQ ID NOs: 1-15 and 48, and a second primer comprising a nucleic acid sequence selected from the group consisting of SEQ ID NOs: 58-72; or
  (II) a first primer comprising SEQ ID NO: 55 and a second primer comprising SEQ ID NO: 73;
(B) a suitable primer pair for amplification of SEQ ID NO: 687 comprises
  (I) a first primer comprising a nucleic acid sequence selected from the group consisting of SEQ ID NOs: 74-88, and a second primer comprising a nucleic acid sequence selected from the group consisting of SEQ ID NOs: 128-142;
  (II) a first primer comprising SEQ ID NO: 120 and a second primer comprising SEQ ID NO: 143; or
  (III) a first primer comprising SEQ ID NO: 125 and a second primer comprising SEQ ID NO: 144;
(C) a suitable primer pair for amplification of SEQ ID NO: 688 comprises a first primer comprising a nucleic acid sequence selected from the group consisting of SEQ ID NOs: 145-159, and a second primer comprising a nucleic acid sequence selected from the group consisting of SEQ ID NOs: 191-205;
(D) a suitable primer pair for amplification of SEQ ID NO: 689 comprises
  (I) a first primer comprising a nucleic acid sequence selected from the group consisting of SEQ ID NOs: 206-220, and a second primer comprising a nucleic acid sequence selected from the group consisting of SEQ ID NOs: 258-272;
  (II) a first primer comprising SEQ ID NO: 251, and a second primer comprising SEQ ID NO: 273; or
  (III) a first primer comprising SEQ ID NO: 255, and a second primer comprising SEQ ID NO: 274;
(E) a suitable primer pair for amplification of SEQ ID NO: 690 comprises a first primer comprising a nucleic acid sequence selected from the group consisting of SEQ ID NOs: 275-289 and 324, and a second primer comprising a nucleic acid sequence selected from the group consisting of SEQ ID NOs: 327-341;
(F) a suitable primer pair for amplification of SEQ ID NO: 691 comprises a first primer comprising a nucleic acid sequence selected from the group consisting of SEQ ID NOs: 342-356, and a second primer comprising a nucleic acid sequence selected from the group consisting of SEQ ID NOs: 393-407;
(G) a suitable primer pair for amplification of SEQ ID NO: 692 comprises
  (I) a first primer comprising SEQ ID NO: 456, and a second primer comprising SEQ ID NO: 480;
  (II) a first primer comprising SEQ ID NO: 459, and a second primer comprising SEQ ID NO: 481; or
  (III) a first primer comprising SEQ ID NO: 462, and a second primer comprising SEQ ID NO: 482;
(H) a suitable primer pair for amplification of SEQ ID NO: 693 comprises a first primer comprising a nucleic acid sequence selected from the group consisting of SEQ ID NOs: 408-423, and a second primer comprising a nucleic acid sequence selected from the group consisting of SEQ ID NOs: 465-479;

(I) a suitable primer pair for amplification of SEQ ID NO: 694 comprises
  (I) a first primer comprising a nucleic acid sequence selected from the group consisting of SEQ ID NOs: 483-497 and 537, and a second primer comprising a nucleic acid sequence selected from the group consisting of SEQ ID NOs: 540-554;
  (II) a first primer comprising SEQ ID NO: 528, and a second primer comprising SEQ ID NO: 555;
  (III) a first primer comprising SEQ ID NO: 531, and a second primer comprising SEQ ID NO: 556; or
  (IV) a first primer comprising SEQ ID NO: 534, and a second primer comprising SEQ ID NO: 557;
(J) a suitable primer pair for amplification of SEQ ID NO: 695 comprises a first primer comprising a nucleic acid sequence selected from the group consisting of SEQ ID NOs: 558-572, and a second primer comprising a nucleic acid sequence selected from the group consisting of SEQ ID NOs: 603-617; and
(K) a suitable primer pair for amplification of SEQ ID NO: 696 comprises a first primer comprising a nucleic acid sequence selected from the group consisting of SEQ ID NOs: 618-633, and a second primer comprising a nucleic acid sequence selected from the group consisting of SEQ ID NOs: 671-685.

In additional examples, the reaction mixture comprises suitable primer pairs for amplification of SEQ ID NOs: 686-688 and one or more of SEQ ID NOs: 689-696.

In particular examples, the sample comprises a food sample or a water sample.

In additional embodiments, the invention relates to an isolated polynucleotide comprising a nucleic acid sequence selected from the group consisting of SEQ ID NO: 1-685.

In other embodiments, the invention relates to an isolated polynucleotide comprising a primer-probe complex, wherein said primer probe complex comprises:
  (A) a primer region comprising a nucleic acid sequence selected from the group consisting of SEQ ID NOs: 1-15, and a probe region comprising a nucleic acid sequence selected from the group consisting of SEQ ID NOs: 16-30;
  (B) a primer region comprising SEQ ID NO: 48, and a probe region comprising a nucleic acid sequence selected from the group consisting of SEQ ID NOs: 49-52;
  (C) a primer region comprising SEQ ID NO: 55, and a probe region comprising SEQ ID NO: 56;
  (D) a primer region comprising a nucleic acid sequence selected from the group consisting of SEQ ID NOs: 74-88, and a probe region comprising a nucleic acid sequence selected from the group consisting of SEQ ID NOs: 89-104;
  (E) a primer region comprising SEQ ID NO: 120, and a probe region comprising a nucleic acid sequence selected from the group consisting of SEQ ID NOs: 121-122;
  (F) a primer region comprising SEQ ID NO: 125, and a probe region comprising SEQ ID NO: 126;
  (G) a primer region comprising a nucleic acid sequence selected from the group consisting of SEQ ID NOs: 145-159, and a probe region comprising a nucleic acid sequence selected from the group consisting of SEQ ID NOs: 160-175;
  (H) a primer region comprising a nucleic acid sequence selected from the group consisting of SEQ ID NOs: 206-220, and a probe region comprising a nucleic acid sequence selected from the group consisting of SEQ ID NOs: 221-235;
  (I) a primer region comprising SEQ ID NO: 251, and a probe region comprising a nucleic acid sequence selected from the group consisting of SEQ ID NOs: 252-253;
  (J) a primer region comprising a nucleic acid sequence selected from the group consisting of SEQ ID NO: 255, and a probe region comprising a nucleic acid sequence selected from the group consisting of SEQ ID NO: 256;
  (K) a primer region comprising a nucleic acid sequence selected from the group consisting of SEQ ID NOs: 275-289, and a probe region comprising a nucleic acid sequence selected from the group consisting of SEQ ID NOs: 290-306;
  (L) a primer region comprising SEQ ID NO: 324, and a probe region comprising SEQ ID NO: 325;
  (M) a primer region comprising a nucleic acid sequence selected from the group consisting of SEQ ID NOs: 342-356, and a probe region comprising a nucleic acid sequence selected from the group consisting of SEQ ID NOs: 357-374;
  (N) a primer region comprising a nucleic acid sequence selected from the group consisting of SEQ ID NOs: 408-423, and a probe region comprising a nucleic acid sequence selected from the group consisting of SEQ ID NOs: 424-439;
  (O) a primer region comprising SEQ ID NO: 456, and a probe region comprising SEQ ID NOs: 457;
  (P) a primer region comprising SEQ ID NO: 459, and a probe region comprising SEQ ID NO: 460;
  (Q) a primer region comprising SEQ ID NO: 462, and a probe region comprising SEQ ID NO: 463;
  (R) a primer region comprising a nucleic acid sequence selected from the group consisting of SEQ ID NOs: 483-497, and a probe region comprising a nucleic acid sequence selected from the group consisting of SEQ ID NOs: 498-512;
  (S) a primer region comprising SEQ ID NO: 528, and a probe region comprising SEQ ID NO: 529;
  (T) a primer region comprising SEQ ID NO: 531, and a probe region comprising SEQ ID NO: 532;
  (U) a primer region comprising SEQ ID NO: 534, and a probe region comprising SEQ ID NO: 535;
  (V) a primer region comprising SEQ ID NO: 537, and a probe region comprising SEQ ID NO: 538;
  (W) a primer region comprising a nucleic acid sequence selected from the group consisting of SEQ ID NOs: 558-572, and a probe region comprising a nucleic acid sequence selected from the group consisting of SEQ ID NOs: 573-587;
  (X) a primer region comprising a nucleic acid sequence selected from the group consisting of SEQ ID NOs: 618-633, and a probe region comprising a nucleic acid sequence selected from the group consisting of SEQ ID NOs: 634-653.

In certain examples, the probe region and primer region each have a 5' and 3' terminus, wherein the 3' terminus of the probe region is attached to the 5' terminus of the primer region via a linker moiety. In other examples, the primer-probe complex further comprises a detectable label.

In still further embodiments, the invention relates to a kit for detection of STEC bacteria in a sample, comprising an isolated polynucleotide of the present application. In other embodiments, the invention relates to a reagent tablet comprising a replication composition of the present application.

SUMMARY OF THE SEQUENCES

SEQ ID NOs: 1-30 are nucleotide sequences capable of use as primers or probes for amplifying and detecting a portion of an *E. coli* Stx1A gene target, such as the target sequence provided herein as SEQ ID NO: 686. Amplification using a primer selected from SEQ ID NOs: 1-30 can be performed in conjunction with a suitable reverse primer, such as one selected from SEQ ID NOs: 58-72. In certain embodiments, one of SEQ ID NOs: 1-15 is used as a primer in conjunction with a probe selected from SEQ ID NOs: 16-30. In certain other embodiments, the 3'terminus of the selected probe is attached to the 5' terminus of the selected primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as an oligonucleotide selected from SEQ ID NOs: 31-47.

SEQ ID NOs: 48-52 are nucleotide sequences capable of use as primers or probes for amplifying and detecting a portion of an *E. coli* Stx1A gene target, such as the target sequence provided herein as SEQ ID NO: 686. Amplification using a primer selected from SEQ ID NOs: 48-52 can be performed in conjunction with a suitable reverse primer, such as one selected from SEQ ID NOs: 58-72. In certain embodiments, SEQ ID NO: 48 is used as a primer in conjunction with a probe selected from SEQ ID NOs: 49-52. In certain other embodiments, the 3' terminus of the selected probe is attached to the 5' terminus of the selected primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as an oligonucleotide selected from SEQ ID NOs: 53-54.

SEQ ID NOs: 55-56 are nucleotide sequences capable of use as primers or probes for amplifying and detecting a portion of an *E. coli* Stx1A gene target, such as the target sequence provided herein as SEQ ID NO: 686. Amplification using a primer selected from SEQ ID NOs: 55-56 can be performed in conjunction with a suitable reverse primer, such as SEQ ID NO: 73. In certain embodiments, SEQ ID NO: 55 is used as a primer in conjunction with a probe comprising SEQ ID NO: 56. In certain other embodiments, the 3' terminus of the SEQ ID NO: 56 probe is attached to the 5' terminus of the SEQ ID NO: 55 primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as SEQ ID NO: 57.

SEQ ID NOs: 74-104 are nucleotide sequences capable of use as primers or probes for amplifying and detecting a portion of an *E. coli* Stx2A gene target, such as the target sequence provided herein as SEQ ID NO: 687. Amplification using a primer selected from SEQ ID NOs: 74-104 can be performed in conjunction with a suitable reverse primer, such as one selected from SEQ ID NOs: 128-142. In certain embodiments, one of SEQ ID NOs: 74-88 is used as a primer in conjunction with a probe selected from SEQ ID NOs: 89-104. In certain other embodiments, the 3' terminus of the selected probe is attached to the 5' terminus of the selected primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as an oligonucleotide selected from SEQ ID NOs: 105-119.

SEQ ID NOs: 120-122 are nucleotide sequences capable of use as primers or probes for amplifying and detecting a portion of an *E. coli* Stx2A gene target, such as the target sequence provided herein as SEQ ID NO: 687. Amplification using a primer selected from SEQ ID NOs: 120-122 can be performed in conjunction with a suitable reverse primer, such as SEQ ID NO: 143. In certain embodiments, SEQ ID NO: 120 is used as a primer in conjunction with a probe selected from SEQ ID NOs: 121-122. In certain other embodiments, the 3' terminus of the selected probe is attached to the 5' terminus of the selected primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as an oligonucleotide selected from SEQ ID NOs: 123-124.

SEQ ID NOs: 125-126 are nucleotide sequences capable of use as primers or probes for amplifying and detecting a portion of an *E. coli* Stx2A gene target, such as the target sequence provided herein as SEQ ID NO: 687. Amplification using a primer selected from SEQ ID NOs: 125-126 can be performed in conjunction with a suitable reverse primer, such as SEQ ID NO: 144. In certain embodiments, SEQ ID NO: 125 is used as a primer in conjunction with a probe comprising SEQ ID NO: 126. In certain other embodiments, the 3' terminus of the SEQ ID NO: 126 probe is attached to the 5' terminus of the SEQ ID NO: 125 primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as SEQ ID NO: 127.

SEQ ID NOs: 145-175 are nucleotide sequences capable of use as primers or probes for amplifying and detecting a portion of an *E. coli* eae gene target, such as the target sequence provided herein as SEQ ID NO: 688. Amplification using a primer selected from SEQ ID NOs: 145-175 can be performed in conjunction with a suitable reverse primer, such as one selected from SEQ ID NOs: 191-205. In certain embodiments, one of SEQ ID NOs: 145-159 is used as a primer in conjunction with a probe selected from SEQ ID NOs: 160-175. In certain other embodiments, the 3' terminus of the selected probe is attached to the 5' terminus of the selected primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as an oligonucleotide selected from SEQ ID NOs: 176-190.

SEQ ID NOs: 206-235 are nucleotide sequences capable of use as primers or probes for amplifying and detecting a portion of an *E. coli* O26 surface antigen gene target, such as the target sequence provided herein as SEQ ID NO: 689. Amplification using a primer selected from SEQ ID NOs: 206-235 can be performed in conjunction with a suitable reverse primer, such as one selected from SEQ ID NOs: 258-272. In certain embodiments, one of SEQ ID NOs: 206-220 is used as a primer in conjunction with a probe selected from SEQ ID NOs: 221-235. In certain other embodiments, the 3' terminus of the selected probe is attached to the 5'terminus of the selected primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as an oligonucleotide selected from SEQ ID NOs: 236-250.

SEQ ID NOs: 251-253 are nucleotide sequences capable of use as primers or probes for amplifying and detecting a portion of an *E. coli* O26 surface antigen gene target, such as the target sequence provided herein as SEQ ID NO: 689. Amplification using a primer selected from SEQ ID NOs: 251-253 can be performed in conjunction with a suitable reverse primer, such as SEQ ID NO: 273. In certain embodiments, SEQ ID NO: 251 is used as a primer in conjunction with a probe selected from SEQ ID NOs: 252-253. In certain other embodiments, the 3' terminus of the selected probe is attached to the 5' terminus of the SEQ ID NO: 251 primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as SEQ ID NO: 254.

SEQ ID NOs: 255-256 are nucleotide sequences capable of use as primers or probes for amplifying and detecting a portion of an *E. coli* O26 surface antigen gene target, such as the target sequence provided herein as SEQ ID NO: 689. Amplification using a primer selected from SEQ ID NOs: 255-256 can be performed in conjunction with a suitable reverse primer, such as SEQ ID NO: 274. In certain embodiments, SEQ ID NO: 255 is used as a primer in conjunction with a probe comprising SEQ ID NO: 256. In certain other embodiments, the 3' terminus of the SEQ ID NO: 256 probe is attached to the 5' terminus of the SEQ ID NO: 255 primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as SEQ ID NO: 257.

SEQ ID NOs: 275-306 are nucleotide sequences capable of use as primers or probes for amplifying and detecting a portion of an *E. coli* S0111 surface antigen gene target, such as the target sequence provided herein as SEQ ID NO: 690. Amplification using a primer selected from SEQ ID NOs: 275-306 can be performed in conjunction with a suitable reverse primer, such as one selected from SEQ ID NOs: 327-341. In certain embodiments, one of SEQ ID NOs: 275-289 is used as a primer in conjunction with a probe selected from SEQ ID NOs: 290-306. In certain other embodiments, the 3' terminus of the selected probe is attached to the 5' terminus of the selected primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as an oligonucleotide selected from SEQ ID NOs: 307-323.

SEQ ID NOs: 324-325 are nucleotide sequences capable of use as primers or probes for amplifying and detecting a portion of an *E. coli* S0111 surface antigen gene target, such as the target sequence provided herein as SEQ ID NO: 690. Amplification using a primer selected from SEQ ID NOs: 324-325 can be performed in conjunction with a suitable reverse primer, such as one selected from SEQ ID NOs: 327-341. In certain embodiments, SEQ ID NO: 324 is used as a primer in conjunction with a probe comprising SEQ ID NO: 325. In certain other embodiments, the 3' terminus of the SEQ ID NO: 325 probe is attached to the 5' terminus of the SEQ ID NO: 324 primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as SEQ ID NO: 326.

SEQ ID NOs: 342-374 are nucleotide sequences capable of use as primers or probes for amplifying and detecting a portion of an *E. coli* O121 surface antigen gene target, such as the target sequence provided herein as SEQ ID NO: 691. Amplification using a primer selected from SEQ ID NOs: 342-374 can be performed in conjunction with a suitable reverse primer, such as one selected from SEQ ID NOs: 393-407. In certain embodiments, one of SEQ ID NOs: 342-356 is used as a primer in conjunction with a probe selected from SEQ ID NOs: 357-374. In certain other embodiments, the 3' terminus of the selected probe is attached to the 5' terminus of the selected primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as an oligonucleotide selected from SEQ ID NOs: 375-392.

SEQ ID NOs: 408-439 are nucleotide sequences capable of use as primers or probes for amplifying and detecting a portion of an *E. coli* O45 surface antigen gene target, such as the target sequence provided herein as SEQ ID NO: 693. Amplification using a primer selected from SEQ ID NOs: 408-439 can be performed in conjunction with a suitable reverse primer, such as one selected from SEQ ID NOs: 465-479. In certain embodiments, one of SEQ ID NOs: 408-423 is used as a primer in conjunction with a probe selected from SEQ ID NOs: 424-439. In certain other embodiments, the 3' terminus of the selected probe is attached to the 5' terminus of the selected primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as an oligonucleotide selected from SEQ ID NOs: 440-455.

SEQ ID NOs: 456-457 are nucleotide sequences capable of use as primers or probes for amplifying and detecting a portion of an *E. coli* O45 surface antigen gene target, such as the target sequence provided herein as SEQ ID NO: 692. Amplification using a primer selected from SEQ ID NOs: 456-457 can be performed in conjunction with a suitable reverse primer, such as SEQ ID NO: 480. In certain embodiments, SEQ ID NO: 456 is used as a primer in conjunction with a probe comprising SEQ ID NO: 457. In certain other embodiments, the 3' terminus of the SEQ ID NO: 457 probe is attached to the 5' terminus of the SEQ ID NO: 456 primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as SEQ ID NO: 458.

SEQ ID NOs: 459-460 are nucleotide sequences capable of use as primers or probes for amplifying and detecting a portion of an *E. coli* O45 surface antigen gene target, such as the target sequence provided herein as SEQ ID NO: 692. Amplification using a primer selected from SEQ ID NOs: 459-460 can be performed in conjunction with a suitable reverse primer, such as SEQ ID NO: 481. In certain embodiments, SEQ ID NO: 459 is used as a primer in conjunction with a probe comprising SEQ ID NO: 460. In certain other embodiments, the 3' terminus of the SEQ ID NO: 460 probe is attached to the 5' terminus of the SEQ ID NO: 459 primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as SEQ ID NO: 461.

SEQ ID NOs: 462-464 are nucleotide sequences capable of use as primers or probes for amplifying and detecting a portion of an *E. coli* O45 surface antigen gene target, such as the target sequence provided herein as SEQ ID NO: 692. Amplification using a primer selected from SEQ ID NOs: 464-464 can be performed in conjunction with a suitable reverse primer, such as SEQ ID NO: 482. In certain embodiments, SEQ ID NO: 462 is used as a primer in conjunction with a probe comprising SEQ ID NO: 463. In certain other embodiments, the 3' terminus of the SEQ ID NO: 463 probe is attached to the 5' terminus of the SEQ ID NO: 462 primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as SEQ ID NO: 464.

SEQ ID NOs: 483-512 are nucleotide sequences capable of use as primers or probes for amplifying and detecting a portion of an *E. coli* O103 surface antigen gene target, such as the target sequence provided herein as SEQ ID NO: 694. Amplification using a primer selected from SEQ ID NOs: 483-512 can be performed in conjunction with a suitable reverse primer, such as one selected from SEQ ID NOs: 540-554. In certain embodiments, one of SEQ ID NOs: 483-497 is used as a primer in conjunction with a probe selected from SEQ ID NOs: 498-512. In certain other embodiments, the 3' terminus of the selected probe is attached to the 5' terminus of the selected primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as an oligonucleotide selected from SEQ ID NOs: 513-527.

SEQ ID NOs: 528-529 are nucleotide sequences capable of use as primers or probes for amplifying and detecting a portion of an *E. coli* O103 surface antigen gene target, such as the target sequence provided herein as SEQ ID NO: 694. Amplification using a primer selected from SEQ ID NOs: 528-529 can be performed in conjunction with a suitable reverse primer, such as SEQ ID NO: 555. In certain embodiments, SEQ ID NO: 528 is used as a primer in conjunction with a probe comprising SEQ ID NO: 529. In certain other embodiments, the 3' terminus of the SEQ ID NO: 529 probe is attached to the 5' terminus of the SEQ ID NO: 528 primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as SEQ ID NO: 530.

SEQ ID NOs: 531-532 are nucleotide sequences capable of use as primers or probes for amplifying and detecting a portion of an *E. coli* O103 surface antigen gene target, such as the target sequence provided herein as SEQ ID NO: 694. Amplification using a primer selected from SEQ ID NOs: 531-532 can be performed in conjunction with a suitable reverse primer, such as SEQ ID NO: 556. In certain embodiments, SEQ ID NO: 531 is used as a primer in conjunction with a probe comprising SEQ ID NO: 532. In certain other embodiments, the 3' terminus of the SEQ ID NO: 532 probe is attached to the 5' terminus of the SEQ ID NO: 531 primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as SEQ ID NO: 533.

SEQ ID NOs: 534-535 are nucleotide sequences capable of use as primers or probes for amplifying and detecting a portion of an *E. coli* O103 surface antigen gene target, such as the target sequence provided herein as SEQ ID NO: 694. Amplification using a primer selected from SEQ ID NOs: 534-535 can be performed in conjunction with a suitable reverse primer, such as SEQ ID NO: 557. In certain embodiments, SEQ ID NO: 534 is used as a primer in conjunction with a probe comprising SEQ ID NO: 535. In certain other embodiments, the 3' terminus of the SEQ ID NO: 535 probe is attached to the 5' terminus of the SEQ ID NO: 534 primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as SEQ ID NO: 536.

SEQ ID NOs: 537-538 are nucleotide sequences capable of use as primers or probes for amplifying and detecting a portion of an *E. coli* O103 surface antigen gene target, such as the target sequence provided herein as SEQ ID NO: 694. Amplification using a primer selected from SEQ ID NOs: 537-538 can be performed in conjunction with a suitable reverse primer, such as one selected from SEQ ID NOs: 540-554. In certain embodiments, SEQ ID NO: 537 is used as a primer in conjunction with a probe comprising SEQ ID NO: 538. In certain other embodiments, the 3' terminus of the SEQ ID NO: 538 probe is attached to the 5' terminus of the SEQ ID NO: 537 primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as SEQ ID NO: 539.

SEQ ID NOs: 558-587 are nucleotide sequences capable of use as primers or probes for amplifying and detecting a portion of an *E. coli* O145 surface antigen gene target, such as the target sequence provided herein as SEQ ID NO: 695. Amplification using a primer selected from SEQ ID NOs: 558-587 can be performed in conjunction with a suitable reverse primer, such as one selected from SEQ ID NOs: 603-617. In certain embodiments, one of SEQ ID NOs: 558-572 is used as a primer in conjunction with a probe selected from SEQ ID NOs: 573-587. In certain other embodiments, the 3' terminus of the selected probe is attached to the 5' terminus of the selected primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as an oligonucleotide selected from SEQ ID NOs: 588-602.

SEQ ID NOs: 618-653 are nucleotide sequences capable of use as primers or probes for amplifying and detecting a portion of an *E. coli* O157 prophage pathogenicity factor gene target, such as the target sequence provided herein as SEQ ID NO: 696. Amplification using a primer selected from SEQ ID NOs: 618-653 can be performed in conjunction with a suitable reverse primer, such as one selected from SEQ ID NOs: 671-685. In certain embodiments, one of SEQ ID NOs: 618-633 is used as a primer in conjunction with a probe selected from SEQ ID NOs: 634-653. In certain other embodiments, the 3' terminus of the selected probe is attached to the 5' terminus of the selected primer via a suitable linker moiety, such as an 18-carbon spacer. In additional embodiments, the probe is detectably labeled and is used in conjunction with a separate quencher oligonucleotide capable of hybridizing to the probe and quenching its fluorescence, such as an oligonucleotide selected from SEQ ID NOs: 654-670.

SEQ ID NO: 686 is the nucleotide sequence of a portion of an E. coli Stx1A gene that is useful for detecting the presence of the Stx1A gene in a sample, and, ultimately, the presence of STEC bacteria in a sample. Suitable primers useful for amplification of SEQ ID NO: 686 include SEQ ID NOs: 1-30, 48-52, 55-56, and 58-73. In certain embodiments, amplification is performed with a forward primer selected from SEQ ID NOs: 1-15 and a reverse primer selected from SEQ ID NOs: 58-72, while detection is accomplished using a probe selected from SEQ ID NOs: 16-30 and, optionally, a quencher oligonucleotide selected from SEQ ID NOs: 31-47. In other embodiments, amplification is performed using SEQ ID NO: 48 as a forward primer and a reverse primer selected from SEQ ID NOs: 58-72, while detection is accomplished using a probe selected from SEQ ID NOs: 49-52 and, optionally, a quencher oligonucleotide selected from SEQ ID NOs: 53-54. In still further embodiments, amplification is performed using SEQ ID NO: 55 as a forward primer and SEQ ID NO: 73 as a reverse primer, while detection is accomplished using SEQ ID NO: 56 as a probe and, optionally, SEQ ID NO: 57 as a quencher oligonucleotide.

SEQ ID NO: 687 is the nucleotide sequence of a portion of an E. coli Stx2A gene that is useful for detecting the presence of the Stx2A gene in a sample, and, ultimately, the presence of STEC bacteria in a sample. Suitable primers useful for amplification of SEQ ID NO: 687 include SEQ ID NOs: 74-104, 120-122, 125-126, and 128-144. In certain embodiments, amplification is performed with a forward primer selected from SEQ ID NOs: 74-88 and a reverse primer selected from SEQ ID NOs: 128-142, while detection is accomplished using a probe selected from SEQ ID NOs: 89-104 and, optionally, a quencher oligonucleotide selected from SEQ ID NOs: 105-119. In other embodiments, amplification is performed using SEQ ID NO: 120 as a forward primer and SEQ ID NO: 143 as a reverse primer, while detection is accomplished using a probe selected from SEQ ID NOs: 121-122 and, optionally, a quencher oligonucleotide selected from SEQ ID NOs: 123-124. In still further embodiments, amplification is performed using SEQ ID NO: 125 as a forward primer and SEQ ID NO: 144 as a reverse primer, while detection is accomplished using SEQ ID NO: 126 as a probe and, optionally, SEQ ID NO: 127 as a quencher oligonucleotide.

SEQ ID NO: 688 is the nucleotide sequence of a portion of an E. coli eae gene that is useful for detecting the presence of the eae gene in a sample, and, ultimately, the presence of STEC bacteria in a sample. Suitable primers useful for amplification of SEQ ID NO: 688 include SEQ ID NOs: 145-175. In certain embodiments, amplification is performed with a forward primer selected from SEQ ID NOs: 145-159 and a reverse primer selected from SEQ ID NOs: 191-205, while detection is accomplished using a probe selected from SEQ ID NOs: 160-175 and, optionally, a quencher oligonucleotide selected from SEQ ID NOs: 176-190.

SEQ ID NO: 689 is the nucleotide sequence of a portion of an E. coli O26 surface antigen gene that is useful for detecting the presence of the 026 surface antigen gene in a sample, and, ultimately, the presence of STEC bacteria in a sample. Suitable primers useful for amplification of SEQ ID NO: 689 include SEQ ID NOs: 206-235, 251-253, 255-256, and 258-274. In certain embodiments, amplification is performed with a forward primer selected from SEQ ID NOs: 206-220 and a reverse primer selected from SEQ ID NOs: 258-272, while detection is accomplished using a probe selected from SEQ ID NOs: 221-235 and, optionally, a quencher oligonucleotide selected from SEQ ID NOs: 236-250. In other embodiments, amplification is performed using SEQ ID NO: 251 as a forward primer and SEQ ID NO: 273 as a reverse primer, while detection is accomplished using a probe selected from SEQ ID NOs: 252-253 and, optionally, SEQ ID NO: 254 as a quencher oligonucleotide. In still further embodiments, amplification is performed using SEQ ID NO: 255 as a forward primer and SEQ ID NO: 274 as a reverse primer, while detection is accomplished using SEQ ID NO: 256 as a probe and, optionally, SEQ ID NO: 257 as a quencher oligonucleotide.

SEQ ID NO: 690 is the nucleotide sequence of a portion of an E. coli O111 surface antigen gene that is useful for detecting the presence of the 0111 surface antigen gene in a sample, and, ultimately, the presence of STEC bacteria in a sample. Suitable primers useful for amplification of SEQ ID NO: 690 include SEQ ID NOs: 275-306, 324-325, and 327-341. In certain embodiments, amplification is performed with a forward primer selected from SEQ ID NOs: 275-289 and a reverse primer selected from SEQ ID NOs: 327-341, while detection is accomplished using a probe selected from SEQ ID NOs: 290-306 and, optionally, a quencher oligonucleotide selected from SEQ ID NOs: 307-323. In other embodiments, amplification is performed using SEQ ID NO: 324 as a forward primer and a reverse primer selected from SEQ ID NOs: 327-341, while detection is accomplished using a probe comprising SEQ ID NO: 325 and, optionally, a quencher oligonucleotide comprising SEQ ID NO: 326.

SEQ ID NO: 691 is the nucleotide sequence of a portion of an E. coli O121 surface antigen gene that is useful for detecting the presence of the 0121 surface antigen gene in a sample, and, ultimately, the presence of STEC bacteria in a sample. Suitable primers useful for amplification of SEQ ID NO: 691 include SEQ ID NOs: 342-356 and 393-407. In certain embodiments, amplification is performed with a forward primer selected from SEQ ID NOs: 342-356 and a reverse primer selected from SEQ ID NOs: 393-407, while detection is accomplished using a probe selected from SEQ ID NOs: 357-374 and, optionally, a quencher oligonucleotide selected from SEQ ID NOs: 375-392.

SEQ ID NO: 692 is the nucleotide sequence of a portion of an E. coli O45 surface antigen gene that is useful for detecting the presence of the O45 surface antigen gene in a sample, and, ultimately, the presence of STEC bacteria in a sample. Suitable primers useful for amplification of SEQ ID NO: 692 include SEQ ID NOs: 456-457, 459-460, 462-463, and 480-482. In certain embodiments, amplification is performed using SEQ ID NO: 456 as a forward primer and SEQ ID NO: 480 as a reverse primer, while detection is accomplished using a probe comprising SEQ ID NO: 457 and, optionally, a quencher oligonucleotide comprising SEQ ID NO: 458. In further embodiments, amplification is performed using SEQ ID NO: 459 as a forward primer and SEQ ID NO: 481 as a reverse primer, while detection is accomplished using a probe comprising SEQ ID NO: 460 and, optionally, a quencher oligonucleotide comprising SEQ ID NO: 461. In still further embodiments, amplification is performed using SEQ ID NO: 462 as a forward primer and SEQ ID NO: 482 as a reverse primer, while detection is accomplished using a probe comprising SEQ ID NO: 463 and, optionally, a quencher oligonucleotide comprising SEQ ID NO: 464.

SEQ ID NO: 693 is the nucleotide sequence of a portion of an *E. coli* O45 surface antigen gene that is useful for detecting the presence of the O45 surface antigen gene in a sample, and, ultimately, the presence of STEC bacteria in a sample. Suitable primers useful for amplification of SEQ ID NO: 692 include SEQ ID NOs: 408-439 and 465-479. In certain embodiments, amplification is performed with a forward primer selected from SEQ ID NOs: 408-423 and a reverse primer selected from SEQ ID NOs: 465-479, while detection is accomplished using a probe selected from SEQ ID NOs: 424-439 and, optionally, a quencher oligonucleotide selected from SEQ ID NOs: 44-455.

SEQ ID NO: 694 is the nucleotide sequence of a portion of an *E. coli* O103 surface antigen gene that is useful for detecting the presence of the 0103 surface antigen gene in a sample, and, ultimately, the presence of STEC bacteria in a sample. Suitable primers useful for amplification of SEQ ID NO: 694 include SEQ ID NOs: 483-512, 528-529, 531-532, 534-535, 537-538, and 540-557. In certain embodiments, amplification is performed with a forward primer selected from SEQ ID NOs: 483-497 and a reverse primer selected from SEQ ID NOs: 550-554, while detection is accomplished using a probe selected from SEQ ID NOs: 498-512 and, optionally, a quencher oligonucleotide selected from SEQ ID NOs: 513-527. In other embodiments, amplification is performed using SEQ ID NO: 528 as a forward primer and SEQ ID NO: 555 as a reverse primer, while detection is accomplished using SEQ ID NO: 529 as a probe and, optionally, a SEQ ID NO: 530 as a quencher oligonucleotide. In still further embodiments, amplification is performed using SEQ ID NO: 531 as a forward primer and SEQ ID NO: 556 as a reverse primer, while detection is accomplished using SEQ ID NO: 532 as a probe and, optionally, SEQ ID NO: 533 as a quencher oligonucleotide. In additional embodiments, amplification is performed using SEQ ID NO: 534 as a forward primer and SEQ ID NO: 557 as a reverse primer, while detection is accomplished using SEQ ID NO: 535 as a probe and, optionally, SEQ ID NO: 536 as a quencher oligonucleotide. In yet further embodiments, amplification is performed using SEQ ID NO: 537 as a forward primer and a reverse primer selected from SEQ ID NOs: 550-554, while detection is accomplished using SEQ ID NO: 538 as a probe and, optionally, SEQ ID NO: 539 as a quencher oligonucleotide.

SEQ ID NO: 695 is the nucleotide sequence of a portion of an *E. coli* O145 surface antigen gene that is useful for detecting the presence of the 0145 surface antigen gene in a sample, and, ultimately, the presence of STEC bacteria in a sample. Suitable primers useful for amplification of SEQ ID NO: 695 include SEQ ID NOs: 558-587 and 603-617. In certain embodiments, amplification is performed with a forward primer selected from SEQ ID NOs: 558-572 and a reverse primer selected from SEQ ID NOs: 603-617, while detection is accomplished using a probe selected from SEQ ID NOs: 573-587 and, optionally, a quencher oligonucleotide selected from SEQ ID NOs: 588-602.

SEQ ID NO: 696 is the nucleotide sequence of a portion of an *E. coli* O157 prophage pathogenicity factor gene that is useful for detecting the presence of the O157 prophage pathogenicity factor gene in a sample, and, ultimately, the presence of STEC bacteria in a sample. Suitable primers useful for amplification of SEQ ID NO: 696 include SEQ ID NOs: 618-653 and 671-685. In certain embodiments, amplification is performed with a forward primer selected from SEQ ID NOs: 618-633 and a reverse primer selected from SEQ ID NOs: 671-685, while detection is accomplished using a probe selected from SEQ ID NOs: 634-653 and, optionally, a quencher oligonucleotide selected from SEQ ID NOs: 654-670.

SEQ ID NOs: 697-700 comprise nucleotide sequences useful for amplifying SV40 DNA, which, in some examples, is employed as a positive control reaction. In certain examples, amplification is performed using SEQ ID NO: 697 or 698 as a forward primer in conjunction with SEQ ID NO: 700 as a reverse primer. In certain embodiments, one of SEQ ID NOs: 697 or 698 is used as a primer in conjunction with SEQ ID NO: 699 as a probe. In certain other embodiments, the 3' terminus the SEQ ID NO: 699 probe is attached to the 5' terminus of the selected primer via a suitable linker moiety, such as an 18-carbon spacer. In additional embodiments, the probe is detectably labeled with a reporter-quencher pair and possesses self-complementary sequences flanking the probe region, thereby allowing the nucleic acid molecule to self-hybridize into a stem-loop structure, thus allowing for quenching of the reporter signal by the quencher molecule.

The sequences conform with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

DETAILED DESCRIPTION OF PREFERRED EMBODIMENTS

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

DEFINITIONS

In this disclosure, a number of terms and abbreviations are used. The following definitions are provided.

As used herein, the term "about" or "approximately" means within 20%, preferably within 10%, and more preferably within 5% of a given value or range.

The term "comprising" is intended to include embodiments encompassed by the terms "consisting essentially of" and "consisting of:" Similarly, the term "consisting essentially of" is intended to include embodiments encompassed by the term "consisting of:"

"Polymerase chain reaction" is abbreviated PCR.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The terms "polynucleotide," "polynucleotide sequence," "nucleic acid sequence," "nucleic acid fragment," and "oligonucleotide" are used interchangeably herein. These terms encompass nucleotide sequences and the like. A polynucleotide may be a polymer of RNA or DNA that is single- or double-stranded, that optionally contains synthetic, non-natural, or altered nucleotide bases. A polynucleotide in the form of a polymer of DNA may be comprised of one or more strands of cDNA, genomic DNA, synthetic DNA, or mixtures thereof.

The term "amplification product" or "amplicon" refers to nucleic acid fragments produced during a primer-directed amplification reaction. Typical methods of primer-directed amplification include polymerase chain reaction (PCR), ligase chain reaction (LCR), or strand displacement amplification (SDA). If PCR methodology is selected, the replication composition may comprise the components for nucleic acid replication, for example: nucleotide triphosphates, two (or more) primers with appropriate sequences, thermostable polymerase, buffers, solutes, and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.). If LCR methodology is selected, then the nucleic acid replication compositions may comprise, for example: a thermostable ligase (e.g., *Thermus aquaticus* ligase), two sets of adjacent oligonucleotides (wherein one member of each set is complementary to each of the target strands), Tris-HCl buffer, KCl, EDTA, NAD, dithiothreitol, and salmon sperm DNA. See, for example, Tabor et al., *Proc. Natl. Acad. Sci. U.S.A.* 82:1074-1078 (1985).

The term "primer" refers to an oligonucleotide (synthetic or occurring naturally) that is capable of acting as a point of initiation of nucleic acid synthesis or replication along a complementary strand when placed under conditions in which synthesis of a complementary strand is catalyzed by a polymerase. A primer can further contain a detectable label, for example a 5' end label. In certain embodiments, primers of the present invention are 8-60 nucleic acids in length. In other embodiments, primers are 10-50, 14-40, or 20-30 nucleic acids in length. In particular embodiments, a primer is at least about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 49, or 60 nucleotides in length.

The term "probe" refers to an oligonucleotide (synthetic or occurring naturally) that is complementary (though not necessarily fully complementary) to a polynucleotide of interest and forms a duplexed structure by hybridization with at least one strand of the polynucleotide of interest. A probe or primer-probe complex can further contain a detectable label. In certain embodiments, probes of the present invention are 8-60 nucleic acids in length. In other embodiments, probes are 10-50, 14-40, or 20-30 nucleic acids in length. In particular embodiments, a probe is at least about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 49, or 60 nucleotides in length.

A probe can either be an independent entity or complexed with or otherwise attached to a primer, such as where a probe is connected via its 3' terminus to a primer's 5' terminus. Such an attachment can be either direct or indirect, such as when the attachment is accomplished through a linker, which may be a nucleotide or non-nucleotide linker and which may be a non-amplifiable linker, such as a hexethylene glycol (HEG) or 18-carbon linker. In such a case, this would be termed a "primer-probe complex." One example of such a primer-probe complex can be found in U.S. Pat. No. 6,326,145, incorporated herein by reference in its entirety, which are frequently referred to as "Scorpion probes" or "Scorpion primers."

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, semiconductor nanocrystals, ligands (e.g., biotin, avidin, streptavidin, or haptens), and the like. A detectable label can also include a combination of a reporter and a quencher.

The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter.

As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

Preferably, the reporter may be selected from fluorescent organic dyes modified with a suitable linking group for attachment to the oligonucleotide, such as to the terminal 3' carbon or terminal 5' carbon. The quencher may also be selected from organic dyes, which may or may not be fluorescent, depending on the embodiment of the present invention. Generally, whether the quencher is fluorescent or simply releases the transferred energy from the reporter by non-radiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, Handbook of Fluorescence Spectra of Aromatic Molecules, 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland, Handbook of Fluorescent Probes and Research Chemicals, Molecular Probes of Eugene, Oreg., 1992, the content of which is incorporated herein by reference.

Preferred reporter-quencher pairs may be selected from xanthene dyes including fluoresceins and rhodamine dyes. Many suitable forms of these compounds are available commercially with substituents on the phenyl groups, which can be used as the site for bonding or as the bonding functionality for attachment to an oligonucleotide. Another preferred group of fluorescent compounds for use as reporters are the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like.

Most preferably, the reporters and quenchers are selected from fluorescein and rhodamine dyes. These dyes and appropriate linking methodologies for attachment to oligonucleotides are well known in the art.

Suitable examples of quenchers may be selected from 6-carboxy-tetramethyl-rhodamine, 4-(4-dimethylaminophenylazo) benzoic acid (DABYL), tetramethylrhodamine (TAMRA), BHQ-0™, BHQ-1™, BHQ-2™, and BHQ-3™, each of which are available from Biosearch Technologies, Inc. of Novato, Calif., QSY-7™, QSY-9™, QSY-21™ and QSY-35™, each of which are available from Molecular Probes, Inc., and the like.

Suitable examples of reporters may be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from available from Applied Biosystems, and the like.

One example of a probe which contains a reporter and a quencher is a Scorpion probe in either a unimolecular or bimolecular conformation. In a unimolecular Scorpion, the probe portion of the primer-probe complex is flanked by self-complementary regions which allow the probe to form into a stem-loop structure when the probe is unbound from its target DNA. Further, in a unimolecular Scorpion, a reporter is typically attached at or near one of the self-complementary regions, such as at the 5' terminus of the Scorpion probe, and a quencher is attached at or near the other self-complementary region, such as immediately 5' to the non-amplifiable linker, such that the quencher is in sufficiently close proximity to the reporter to cause quenching when the probe is in its stem-loop conformation. In a bimolecular Scorpion, self-complementary flanking regions are not typically employed, but rather a separate "blocking oligonucleotide" or "quenching oligonucleotide" is employed in conjunction with the Scorpion probe. This blocking oligonucleotide is capable of hybridizing to the probe region of the Scorpion probe when the probe is unbound from its target DNA. Further, in a bimolecular Scorpion, the reporter is typically attached to the probe region of the Scorpion probe, such as at the 5' terminus of the Scorpion probe, while the quencher is attached to the blocking oligonucleotide, such as at the 3' terminus of the blocking oligonucleotide, such that the quencher is in sufficiently close proximity to the reporter to cause quenching when the probe is unbound from its target DNA and is instead hybridized to the blocking oligonucleotide.

Another example of a probe which contains a reporter and a quencher is a probe that is to be used in a 5'-exonuclease assay, such as the Taqman® real-time PCR technique. In this context, the oligonucleotide probe will have a sufficient number of phosphodiester linkages adjacent to its 5' end so that the 5' to 3' nuclease activity employed can efficiently degrade the bound probe to separate the reporters and quenchers. Yet another example of a probe which contains a reporter and quencher is a Molecular Beacon type probe, which contains a probe region flanked by self-complementary regions that allow the probe to form a stem-loop structure when unbound from the probe's target sequence. Such probes typically have a reporter attached at or near one terminus and a quencher attached at or near the other terminus such that the quencher is in sufficiently close proximity to the reporter to cause quenching when the probe is in its unbound, and thus stem-loop, form.

The term "replication inhibitor moiety" refers to any atom, molecule or chemical group that is attached to the 3' terminal hydroxyl group of an oligonucleotide that will block the initiation of chain extension for replication of a nucleic acid strand. Examples include, but are not limited to: 3'-deoxynucleotides (e.g., cordycepin), dideoxynucleotides, phosphate, ligands (e.g., biotin and dinitrophenol), reporter molecules (e.g., fluorescein and rhodamine), carbon chains (e.g., propanol), a mismatched nucleotide or polynucleotide, or peptide nucleic acid units. The term "non-participatory" refers to the lack of participation of a probe or primer in a reaction for the amplification of a nucleic acid molecule. Specifically a non-participatory probe or primer is one that will not serve as a substrate for, or be extended by, a DNA or RNA polymerase. A "non-participatory probe" is inherently incapable of being chain extended by a polymerase. It may or may not have a replication inhibitor moiety.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, for example, in Sambrook, J., Fritsch, E. F. and Maniatis, T., *Molecular Cloning: A Laboratory Manual*, 2nd ed., Cold Spring Harbor Laboratory Cold Spring Harbor, N.Y. (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55° C., can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one preferred embodiment, the length for a hybridizable nucleic acid is at least about 10 nucleotides. More preferably a minimum length for a hybridizable nucleic acid is at least about 11 nucleotides, at least about 12 nucleotides, at least about 13 nucleotides, at least about 14 nucleotides, at least about 15 nucleotides, at least about 16 nucleotides, at least about 17 nucleotides, at least about 18 nucleotides, at least about 19 nucleotides, at least about 20 nucleotides, at least about 21 nucleotides, at least about 22 nucleotides, at least about 23 nucleotides, at least about 24 nucleotides, at least about 25 nucleotides, at least about 26 nucleotides, at least about 27 nucleotides, at least about 28 nucleotides, at least about 29 nucleotides, or, most preferably, at least 30 nucleotides. Furthermore, the skilled artisan will recognize that the temperature and wash solution salt concentration may be adjusted as necessary according to factors such as length of the probe.

Standard recombinant DNA and molecular cloning techniques used here are well known in the art and are described by, e.g., Sambrook et al. (supra); and by Ausubel, F. M. et al., *Current Protocols in Molecular Biology*, published by Greene Publishing Assoc. and Wiley-Interscience (1987).

Oligonucleotides

Methods have been developed for detecting STEC bacteria by detecting one or more gene targets selected from Stx1A, Stx2A, eae, O26, O111, O121, O45, O103, O145, and O157. In certain embodiments, the methods involve detecting one or both of Stx1A and Stx2A, as well as detecting eae, and, optionally, one or more of O26, O111, O121, O45, O103, O145, and O157. In still further embodiments, the methods involve detecting one or more of SEQ ID NOs: 686-688. In certain embodiments, the method involves detecting one or both of SEQ ID NOs: 686-687, as well as detecting SEQ ID NO: 688, and, optionally, one or more of SEQ ID NOs: 689-696. Oligonucleotides have been developed for the detection of such nucleotide sequences and the subsequent detection and identification of STEC bacteria, including forward and reverse primers, probes, and quencher oligonucleotides. Oligonucleotides of the instant invention may be used as primers for PCR amplification. Exemplary primer pairs and their corresponding targets, blocking oligonucleotides, and probes are shown in Table 1.

TABLE 1

Target sequences and the primers, probes, and quenchers related thereto

| Target Gene Name | Target Gene SEQ ID NO. | 5' (Forward) Primer(s) SEQ ID NO(s) | Probe(s) SEQ ID NO(s) | Quencher Oligo(s) SEQ ID NO(s) | 3' (Reverse) Primer(s) SEQ ID NO(s) |
|---|---|---|---|---|---|
| Stx1A | 686 | 1-15 | 16-30 | 41-47 | 58-72 |
| | | 48 | 49-52 | 53-54 | 58-72 |
| | | 55 | 56 | 57 | 73 |
| Stx2A | 687 | 74-88 | 89-104 | 105-119 | 128-142 |
| | | 120 | 121-122 | 123-124 | 143 |
| | | 125 | 126 | 127 | 144 |
| Eae | 688 | 145-159 | 160-175 | 176-190 | 191-205 |
| O26 | 689 | 206-220 | 221-235 | 236-250 | 258-272 |
| | | 251 | 252-253 | 254 | 273 |
| | | 255 | 256 | 257 | 274 |

TABLE 1-continued

Target sequences and the primers, probes, and quenchers related thereto

| Target Gene Name | Target Gene SEQ ID NO. | 5' (Forward) Primer(s) SEQ ID NO(s) | Probe(s) SEQ ID NO(s) | Quencher Oligo(s) SEQ ID NO(s) | 3' (Reverse) Primer(s) SEQ ID NO(s) |
|---|---|---|---|---|---|
| O111 | 690 | 275-289 | 290-306 | 307-323 | 327-341 |
| | | 324 | 325 | 326 | 327-341 |
| O121 | 691 | 342-356 | 357-374 | 375-392 | 393-407 |
| O45 | 692 | 456 | 457 | 458 | 480 |
| | | 459 | 460 | 461 | 481 |
| | | 462 | 463 | 464 | 482 |
| | 693 | 408-423 | 424-439 | 440-455 | 465-479 |
| O103 | 694 | 483-497 | 498-512 | 513-527 | 540-554 |
| | | 528 | 529 | 530 | 555 |
| | | 531 | 532 | 533 | 556 |
| | | 534 | 535 | 536 | 557 |
| | | 537 | 538 | 539 | 540-555 |
| O145 | 695 | 558-572 | 573-587 | 588-602 | 603-617 |
| O157 | 696 | 618-633 | 634-653 | 654-670 | 671-685 |

Each of these primers and probes was designed based on sequence analysis of its corresponding region of the *E. coli* genome.

In certain embodiments, a primer for amplifying and/or detecting SEQ ID NO: 686 comprises at least about 15 contiguous nucleotides of SEQ ID NO: 1, 48, or 55, or a sequence complementary thereto. In other embodiments a probe for amplifying and/or detecting SEQ ID NO: 686 comprises at least about 15 contiguous nucleotides of SEQ ID NO: 16, 49-52, or 56, or a sequence complementary thereto. In further embodiments, a quencher useful for quenching the signal of such a probe comprises at least about 15 contiguous nucleotides of SEQ ID NO: 41, 53, 54, or 57, or a sequence complementary thereto. In additional embodiments a second primer, or reverse primer, for amplifying and/or detecting SEQ ID NO: 686 comprises at least about 15 contiguous nucleotides of SEQ ID NO: 58 or 73, or a sequence complementary thereto. In still further embodiments, at least about 16, 17, 18, 19, 20, 21, 22, 23, 24, 25, 26, 27, 28, 29, or 30 contiguous nucleotides of these sequences could be used.

In certain embodiments, a primer for amplifying and/or detecting SEQ ID NO: 687 comprises at least about 15 contiguous nucleotides of SEQ ID NO: 74, 120, or 125, or a sequence complementary thereto. In other embodiments a probe for amplifying and/or detecting SEQ ID NO: 687 comprises at least about 15 contiguous nucleotides of SEQ ID NO: 89, 121, 122, or 126, or a sequence complementary thereto. In further embodiments, a quencher useful for quenching the signal of such a probe comprises at least about 15 contiguous nucleotides of SEQ ID NO: 105, 123, 124, or 127, or a sequence complementary thereto. In additional embodiments a second primer, or reverse primer, for amplifying and/or detecting SEQ ID NO: 687 comprises at least about 15 contiguous nucleotides of SEQ ID NO: 128, 143, or 144, or a sequence complementary thereto. In still further embodiments, at least about 16, 17, 18, 19, 20, 21, 22, 23, 24, 25, 26, 27, 28, 29, or 30 contiguous nucleotides of these sequences could be used.

In certain embodiments, a primer for amplifying and/or detecting SEQ ID NO: 688 comprises at least about 15 contiguous nucleotides of SEQ ID NO: 145, or a sequence complementary thereto. In other embodiments a probe for amplifying and/or detecting SEQ ID NO: 688 comprises at least about 15 contiguous nucleotides of SEQ ID NO: 160, or a sequence complementary thereto. In further embodiments, a quencher useful for quenching the signal of such a probe comprises at least about 15 contiguous nucleotides of SEQ ID NO: 176, or a sequence complementary thereto. In additional embodiments a second primer, or reverse primer, for amplifying and/or detecting SEQ ID NO: 688 comprises at least about 15 contiguous nucleotides of SEQ ID NO: 191, or a sequence complementary thereto. In still further embodiments, at least about 16, 17, 18, 19, 20, 21, 22, 23, 24, 25, 26, 27, 28, 29, or contiguous nucleotides of these sequences could be used.

These oligonucleotide primers may also be useful for other nucleic acid amplification methods such as the ligase chain reaction (LCR) (Backman et al., 1989, EP 0 320 308; Carrino et al., 1995, *J. Microbiol. Methods* 23: 3-20); nucleic acid sequence-based amplification (NASBA), (Carrino et al., 1995, supra); and self-sustained sequence replication (3SR) and 'Q replicase amplification' (Pfeffer et al., 1995 *Veterinary Res. Comm.* 19: 375-407).

The oligonucleotide primers of the present invention can also contain a detectable label, for example a 5' end label.

In addition, oligonucleotides of the present invention also may be used as hybridization probes. Some examples of useful probes are provided in Table 1. Hybridization using DNA probes has been frequently used for the detection of pathogens in food, clinical and environmental samples, and the methodologies are generally known to one skilled in the art. It is generally recognized that the degree of sensitivity and specificity of probe hybridization is lower than that achieved through the previously described amplification techniques. The nucleic acid probes of the present invention can also possess a detectable label, such as a reporter-quencher combination as are employed in Scorpion probe assays or in 5'-exonuclease detection assays, such as the Taqman® assay.

The 3' terminal nucleotide of the nucleic acid probe may be rendered incapable of extension by a nucleic acid polymerase in one embodiment of the invention. Such blocking may be carried out, for example by the attachment of a replication inhibitor moiety, such as a reporter or quencher, to the terminal 3' carbon of the nucleic acid probe by a linking moiety, or by making the 3'-terminal nucleotide a dideoxynucleotide. Alternatively, the 3' end of the nucleic acid probe may be rendered impervious to the 3' to 5' extension activity of a polymerase by incorporating one or more modified internucleotide linkages onto the 3' end of the oligonucleotide. Minimally, the 3' terminal internucleotide linkage must be modified, however, additional internucleotide linkages may be modified. Internucleotide modifications which prevent elongation from the 3' end of the nucleic acid probe and/or which block the 3' to 5' exonuclease activity of the DNA polymerase during PCR may include phosphorothioate linkages, methylphosphonate linkages, boranophosphate linkages, and other similar polymerase-resistant internucleotide linkages. An alternative method to block 3' extension of the probe is to form an adduct at the 3' end of the probe using mitomycin C or other like antitumor antibiotics such as described in Basu et al., Biochemistry 32:4708-4718, 1993. Thus, the precise mechanism by which the 3' end of the nucleic acid probe is protected from cleavage is not essential so long as the quencher is not cleaved from the nucleic acid probe.

A nucleic acid probe sequence can also optionally be employed with the primer sequence pairs of the present invention in an amplification based detection technique, such as in the 3'-exonuclease assay. Preferred primer/probe combinations are indicated in Table 1.

In some embodiments a corresponding primer and probe are used together in a primer-probe complex. In such embodiments, the 3' terminus of the probe is typically attached to the 5' terminus of the primer. These primer probe complexes of the instant invention can contain a non-amplifiable linker that connects the 3' terminus of the probe region to the 5' terminus of the primer region. This non-amplifiable linker stops extension of a complementary strand from proceeding into the probe region of the primer-probe complex. Examples of such non-amplifiable linkages include hexethylene glycol (HEG) and, preferably, 18-carbon linkers. Primer-probe complexes of the present invention can also contain a self-complementary region that allows the primer-probe complex to form a stem-loop structure when the probe is unbound from its target DNA, which may be useful, for example, in bringing the reporter and quencher into sufficiently close proximity to one another to cause the reporter signal to be quenched. In some instances, a quencher oligonucleotide can be employed with a primer-probe complex, which quencher oligonucleotide is capable of hybridizing to the probe region of the primer-probe complex when the probe region is unbound from its target DNA. If the reporter is attached to the primer-probe complex and the quencher is attached to the blocking oligonucleotide, this can bring the reporter and quencher into sufficiently close proximity to one another to allow quenching to occur. Examples of corresponding primers, probes, and quenchers are provided in Table 1.

Assay Methods

Detection of the selected gene targets and/or the genomic DNA regions identified by SEQ ID NOs: 686-696, and subsequent detection of the presence of STEC bacteria in a sample, may be accomplished in any suitable manner. Preferred methods are primer-directed amplification methods and nucleic acid hybridization methods. These methods may be used to detect STEC bacteria in a sample that is either a complex matrix or a purified culture, e.g., from an animal, environmental, or food source suspected of contamination.

A preferred embodiment of the instant invention comprises (1) culturing a complex sample mixture in a non-selective growth media to resuscitate the target bacteria, (2) releasing total target bacterial DNA, and (3) subjecting the total DNA to an amplification protocol with a primer pair of the invention and optionally with a nucleic acid probe comprising a detectable label.

Primer-Directed Amplification Assay Methods

A variety of primer-directed nucleic acid amplification methods are known in the art which can be employed in the present invention, including thermal cycling methods (e.g., PCR, RT-PCR, and LCR), as well as isothermal methods and strand displacement amplification (SDA). The preferred method is PCR. In one preferred embodiment, the corresponding forward and reverse primer pairs listed in Table 1 may be used as primers for use in primer-directed nucleic acid amplification for the detection of the target genes of interest and/or SEQ ID NOs: 686-696, and, ultimately, the detection and identification of STEC bacteria.

Sample Preparation:

The oligonucleotides and methods according to the instant invention may be used directly with any suitable clinical or environmental samples, without any need for sample preparation. In order to achieve higher sensitivity, and in situations where time is not a limiting factor, it is preferred that the samples be pre-treated and that pre-amplification enrichment is performed.

The minimum industry standard for the detection of food-borne bacterial pathogens is a method that will reliably detect the presence of one pathogen cell in 25 g of food matrix as described in Andrews et al., 1984, "Food Sample and Preparation of Sample Homogenate", Chapter 1 in *Bacteriological Analytical Manual*, 8th Edition, Revision A, Association of Official Analytical Chemists, Arlington, Va. In order to satisfy this stringent criterion, enrichment methods and media have been developed to enhance the growth of the target pathogen cell in order to facilitate its detection by biochemical, immunological or nucleic acid hybridization means. Typical enrichment procedures employ media that will enhance the growth and health of the target bacteria and also inhibit the growth of any background or non-target microorganisms present. For example, the USDA has set forth a protocol for enrichment of samples of ground beef to be tested for pathogenic *E. coli* (U.S. Food and Drug Administration, Bacterial Analytical Manual).

Selective media have been developed for a variety of bacterial pathogens and one of skill in the art will know to select a medium appropriate for the particular organism to be enriched. A general discussion and recipes of non-selective media are described in the FDA Bacteriological Analytical Manual. (1998) published and distributed by the Association of Analytical Chemists, Suite 400, 2200 Wilson Blvd, Arlington, Va. 22201-3301.

After selective growth, a sample of the complex mixtures is removed for further analysis. This sampling procedure may be accomplished by a variety of means well known to those skilled in the art. In a preferred embodiment, 5 µl of the enrichment culture is removed and added to 200 µl of lysis solution containing protease. The lysis solution is heated at 37° C. for 20 min followed by protease inactivation at 95° C. for 10 min as described in the BAX® System User's Guide, DuPont Qualicon, Inc., Wilmington, Del.

PCR Assay Methods:

A preferred method for detecting the presence of the present invention's gene targets and subsequently STEC bacteria in a sample comprises (a) performing PCR amplification of two or more of SEQ ID NOs: 686-696 using primer pairs listed in Table 1 to produce a PCR amplification result; and (b) detecting the amplification, whereby a positive detection of the amplification indicates the presence of STEC bacteria in the sample.

In another preferred embodiment, prior to performing PCR amplification, a step of preparing the sample may be carried out. The preparing step may comprise at least one of the following processes: (1) bacterial enrichment, (2) separation of bacterial cells from the sample, (3) cell lysis, and (4) total DNA extraction.

Amplification Conditions:

A skilled person will understand that any generally acceptable PCR conditions may be used for successfully detecting the gene targets and the target STEC bacteria using the oligonucleotides of the instant invention, and depending on the sample to be tested and other laboratory conditions, routine optimization for the PCR conditions may be necessary to achieve optimal sensitivity and specificity. Optimally, they achieve PCR amplification results from all of the intended specific targets while giving no PCR results for other, non-target species.

Detection/Examination/Analysis:

Primer-directed amplification products of SEQ ID NOs: 686-696 can be analyzed using various methods. Homogenous detection refers to a preferred method for the detection of amplification products where no separation (such as by gel electrophoresis) of amplification products from template or primers is necessary. Homogeneous detection is typically accomplished by measuring the level of fluorescence of the reaction mixture during or immediately following amplification. In addition, heterogeneous detection methods, which involve separation of amplification products during or prior to detection, can be employed in the present invention.

Homogenous detection may be employed to carry out "real-time" primer-directed nucleic acid amplification and detection, using primer pairs of the instant invention (e.g., "real-time" PCR and "real-time" RT-PCR). Preferred "real-time" methods are set forth in U.S. Pat. Nos. 6,171,785, 5,994,056, 6,326,145, 5,804,375, 5,538,848, 5,487,972, and 5,210,015, each of which is hereby incorporated by reference in its entirety.

A particularly preferred "real-time" detection method is the Scorpion probe assay as set forth in U.S. Pat. No. 6,326,145, which is hereby incorporated by reference in its entirety. In the Scorpion probe assay, PCR amplification is performed using a Scorpion probe (either unimolecular or bimolecular) as a primer-probe complex, the Scorpion probe possessing an appropriate reporter-quencher pair to allow the detectable signal of the reporter to be quenched prior to elongation of the primer. Post-elongation, the quenching effect is eliminated and the amount of signal present is quantitated. As the amount of amplification product increases, an equivalent increase in detectable signal will be observed, thus allowing the amount of amplification product present to be determined as a function of the amount of detectable signal measured. When more than one Scorpion probe is employed in a Scorpion probe assay of present invention, each probe can have a different detectable label (e.g., reporter-quencher pair) attached, thus allowing each probe to be detected independently of the other probes.

In a certain embodiment, amplification and detection of two or more of SEQ ID NOs: 686-696 is performed using differentially labeled Scorpion probes. Examples of primers and probes, including the target sequences to which they are directed, are provided in Table 1. Additional specific examples of primers, probes, and quenchers which can be employed alone or in combination for detection of STEC bacteria are provided in Tables 2, 3, and 8.

Another preferred "real-time" detection method is the 5'-exonuclease detection method, as set forth in U.S. Pat. Nos. 5,804,375, 5,538,848, 5,487,972, and 5,210,015, each of which is hereby incorporated by reference in its entirety. In the 5'-exonuclease detection assay a modified probe is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are preferably attached to the probe within a few nucleotides of one another, usually within 30 nucleotides of one another, more preferably with a separation of from about 6 to 16 nucleotides. Typically, this separation is achieved by attaching one member of a reporter-quencher pair to the 5' end of the probe and the other member to a nucleotide about 6 to 16 nucleotides away.

Again, when more than one Taqman® probe is employed in a 5'-exonuclease detection assay of present invention, such as one directed to two or more of SEQ ID NOs: 686-696, each probe can have a different detectable label (e.g., reporter-quencher pair) attached, thus allowing each probe to be detected independently of the other probes.

Another preferred method of homogenous detection involves the use of DNA melting curve analysis, particularly with the BAX® System hardware and reagent tablets from DuPont Qualicon Inc. The details of the system are given in U.S. Pat. No. 6,312,930 and PCT Publication Nos. WO 97/11197 and WO 00/66777, each of which is hereby incorporated by reference in its entirety.

Melting curve analysis detects and quantifies double stranded nucleic acid molecule ("dsDNA" or "target") by monitoring the fluorescence of the target amplification product ("target amplicon") during each amplification cycle at selected time points.

As is well known to the skilled artisan, the two strands of a dsDNA separate or melt, when the temperature is higher than its melting temperature. Melting of a dsDNA molecule is a process, and under a given solution condition, melting starts at a temperature (designated $T_{MS}$ hereinafter), and completes at another temperature (designated $T_{ME}$ hereinafter). The familiar term, $T_m$, designates the temperature at which melting is 50% complete.

A typical PCR cycle involves a denaturing phase where the target dsDNA is melted, a primer annealing phase where the temperature optimal for the primers to bind to the now-single-stranded target, and a chain elongation phase (at a temperature $T_E$) where the temperature is optimal for DNA polymerase to function.

According to the present invention, $T_{MS}$ should be higher than $T_E$, and $T_{ME}$ should be lower (often substantially lower) than the temperature at which the DNA polymerase is heat-inactivated. Melting characteristics are effected by the intrinsic properties of a given dsDNA molecule, such as deoxynucleotide composition and the length of the dsDNA.

Intercalating dyes will bind to double stranded DNA. The dye/dsDNA complex will fluoresce when exposed to the appropriate excitation wavelength of light, which is dye dependent, and the intensity of the fluorescence may be proportionate to concentration of the dsDNA. Methods taking advantage of the use of DNA intercalating dyes to detect and quantify dsDNA are known in the art. Many dyes are known and used in the art for these purposes. The instant methods also take advantage of such relationship.

Examples of such intercalating dyes include, but are not limited to, SYBR Green-I®, ethidium bromide, propidium iodide, TOTO®-1 {Quinolinium, 1-1'-[1,3-propanediylbis[(dimethyliminio)-3,1-propanediyl]]bis[4-[(3-methyl-2(3H)-benzothiazolylidene)methyl]]-, tetraiodide}, and YoPro® {Quinolinium, 4-[(3-methyl-2(3H)-benzoxazolylidene)methyl]-1-[3-(trimethylammonio)-propyl]-,diiodide}. Most preferred for the instant invention is a non-asymmetrical cyanide dye such as SYBR Green-I®, manufactured by Molecular Probes, Inc. (Eugene, Oreg.).

Melting curve analysis is achieved by monitoring the change in fluorescence while the temperature is increased. When the temperature reaches the $T_{MS}$ specific for the target amplicon, the dsDNA begins to denature. When the dsDNA denatures, the intercalating dye dissociates from the DNA and fluorescence decreases. Mathematical analysis of the negative of the change of the log of fluorescence divided by the change in temperature plotted against the temperature results in the graphical peak known as a melting curve.

It should be understood that the present invention could be operated using a combination of these techniques, such as by having a Scorpion probe directed to one target region and a Taqman® probe directed to a second target region. It should also be understood that the invention is not limited to the above described techniques. Rather, one skilled in the art would recognize that other techniques for detecting amplification as known in the art may also be used. For example, techniques such as PCR-based quantitative sequence detection (QSD) may be performed using nucleic acid probes which, when present in the single-stranded state in solution, are configured such that the reporter and quencher are sufficiently close to substantially quench the reporter's emission. However, upon hybridization of the intact reporter-quencher nucleic acid probe with the amplified target nucleic acid sequence, the reporter and quenchers become sufficiently distant from each other. As a result, the quenching is substantially abated causing an increase in the fluorescence emission detected.

In addition to homogenous detection methods, a variety of other heterogeneous detection methods are known in the art which can be employed in the present invention, including standard non-denaturing gel electrophoresis (e.g., acrylamide or agarose), denaturing gradient gel electrophoresis, and temperature gradient gel electrophoresis. Standard non-denaturing gel electrophoresis is a simple and quick method of PCR detection, but may not be suitable for all applications.

Denaturing Gradient Gel Electrophoresis (DGGE) is a separation method that detects differences in the denaturing behavior of small DNA fragments (200-700 bp). The principle of the separation is based on both fragment length and nucleotide sequence. In fragments that are the same length, a difference as little as one base pair can be detected. This is in contrast to non-denaturing gel electrophoresis, where DNA fragments are separated only by size. This limitation of non-denaturing gel electrophoresis results because the difference in charge density between DNA molecules is near neutral and plays little role in their separation. As the size of the DNA fragment increases, its velocity through the gel decreases.

DGGE is primarily used to separate DNA fragments of the same size based on their denaturing profiles and sequence. Using DGGE, two strands of a DNA molecule separate, or melt, when heat or a chemical denaturant is applied. The denaturation of a DNA duplex is influenced by two factors: 1) the hydrogen bonds formed between complimentary base pairs (since GC rich regions melt at higher denaturing conditions than regions that are AT rich); and 2) the attraction between neighboring bases of the same strand, or "stacking." Consequently, a DNA molecule may have several melting domains with each of their individual characteristic denaturing conditions determined by their nucleotide sequence. DGGE exploits the fact that otherwise identical DNA molecules having the same length and DNA sequence, with the exception of only one nucleotide within a specific denaturing domain, will denature at different temperatures or Tm. Thus, when the double-stranded (ds) DNA fragment is electrophoresed through a gradient of increasing chemical denaturant it begins to denature and undergoes both a conformational and mobility change. The dsDNA fragment will travel faster than a denatured single-stranded (ss) DNA fragment, since the branched structure of the single-stranded moiety of the molecule becomes entangled in the gel matrix. As the denaturing environment increases, the dsDNA fragment will completely dissociate and mobility of the molecule through the gel is retarded at the denaturant concentration at which the particular low denaturing domains of the DNA strand dissociate. In practice, the electrophoresis is conducted at a constant temperature (around 60° C.) and chemical denaturants are used at concentrations that will result in 100% of the DNA molecules being denatured (i.e., 40% formamide and 7M urea). This variable denaturing gradient is created using a gradient maker, such that the composition of each DGGE gel gradually changes from 0% denaturant up to 100% denaturant. Of course, gradients containing a reduced range of denaturant (e.g., 35% to 60%) may also be poured for increased separation of DNA.

The principle used in DGGE can also be applied to a second method that uses a temperature gradient instead of a chemical denaturant gradient. This method is known as Temperature Gradient Gel Electrophoresis (TGGE). This method makes use of a temperature gradient to induce the conformational change of dsDNA to ssDNA to separate fragments of equal size with different sequences. As in DGGE, DNA fragments with different nucleotide sequences will become immobile at different positions in the gel. Variations in primer design can be used to advantage in increasing the usefulness of DGGE for characterization and identification of the PCR products. These methods and principles of using primer design variations are described in PCR Technology Principles and Applications, Henry A. Erlich Ed., M. Stockton Press, NY, pages 71 to 88 (1988).

Instrumentation:

When homogenous detection is employed, the level of fluorescence is preferably measured using a laser fluorometer such as, for example, an ABI Prism Model 7500 Fast Sequence Detector. However, similar detection systems for measuring the level of fluorescence in a sample are included in the invention.

Reagents and Kits:

Any suitable nucleic acid replication composition ("replication composition") in any format can be used. A typical replication composition for PCR amplification may comprise, for example, dATP, dCTP, dGTP, dTTP, target specific primers and a suitable polymerase.

If the replication composition is in liquid form, suitable buffers known in the art may be used (Sambrook, J. et al., supra).

Alternatively, if the replication composition is contained in a tablet form, then typical tabletization reagents may be included such as stabilizers and binding agents. Preferred tabletization technology is set forth in U.S. Pat. Nos. 4,762,857 and 4,678,812, each of which is hereby incorporated by reference in its entirety.

A preferred replication composition of the instant invention comprises (a) at least one primer pair selected from Table 1, and (b) thermostable DNA polymerase. Another preferred replication composition comprises (a) at least two primer pairs selected from Table 1, each directed toward a different target DNA region; and (b) thermostable DNA polymerase. In some embodiments, primer pairs directed to three or more of SEQ ID NOs: 686-696 are included. In further embodiments, primer pairs directed to four or more of SEQ ID NOs: 686-696 are included. In still further embodiments, primer pairs directed to five or more of SEQ ID NOs: 686-696 are included.

A more preferred replication composition of the present invention comprises (a) at least two primer pairs and any corresponding probe or blocking oligonucleotide selected from Table 1, wherein each nucleic acid probe or primer-probe complex employed comprises a detectable label; and (b) thermostable DNA polymerase. Preferably the detectable label comprises a reporter capable of emitting a detectable signal and a quencher capable of substantially quenching the reporter and preventing the emission of the detectable signal when the reporter and quencher are in sufficiently close proximity to one another.

A preferred kit of the instant invention comprises any one of the above replication compositions. A preferred tablet of the instant invention comprises any one of the above replication compositions. More preferably, a kit of the instant invention comprises the foregoing preferred tablet.

In some instances, an internal positive control can be included in the reaction. The internal positive control can include control template nucleic acids (e.g. DNA or RNA), control primers, and control nucleic acid probe. The advantages of an internal positive control contained within a PCR reaction have been previously described (U.S. Pat. No. 6,312,930 and PCT Application No. WO 97/11197, each of which is hereby incorporated by reference in its entirety), and include: (i) the control may be amplified using a single primer; (ii) the amount of the control amplification product is independent of any target DNA or RNA contained in the sample; (iii) the control DNA can be tabletted with other amplification reagents for ease of use and high degree of reproducibility in both manual and automated test procedures; (iv) the control can be used with homogeneous detection, i.e., without separation of product DNA from reactants; and (v) the internal control has a melting profile that is distinct from other potential amplification products in the reaction and/or a detectable label on the control nucleic acid that is distinct from the detectable label on the nucleic acid probe directed to the target.

Control DNA will be of appropriate size and base composition to permit amplification in a primer-directed amplification reaction. The control template DNA sequence may be obtained from the *E. coli* genome, or from another source, but must be reproducibly amplified under the same conditions that permit the amplification of the target amplification product.

Preferred control sequences include, for example, control primers and probes directed toward SV40 DNA.

The control reaction is useful to validate the amplification reaction. Amplification of the control DNA occurs within the same reaction tube as the sample that is being tested, and therefore indicates a successful amplification reaction when samples are target negative, i.e. no target amplification product is produced. In order to achieve significant validation of the amplification reaction, a suitable number of copies of the control DNA template must be included in each amplification reaction.

In some instances it may be useful to include an additional negative control replication composition. The negative control replication composition will contain the same reagents as the replication composition but without the polymerase. The primary function of such a control is to monitor spurious background fluorescence in a homogeneous format when the method employs a fluorescent means of detection.

Replication compositions may be modified depending on whether they are designed to be used to amplify target DNA or the control DNA. Replication compositions that will amplify the target DNA (test replication compositions) may include (i) a polymerase (generally thermostable), (ii) a primer pair capable of hybridizing to the target DNA and (iii) necessary buffers for the amplification reaction to proceed. Replication compositions that will amplify the control DNA (positive control, or positive replication composition) may include (i) a polymerase (generally thermostable) (ii) the control DNA; (iii) at least one primer capable of hybridizing to the control DNA; and (iv) necessary buffers for the amplification reaction to proceed. In addition, the replication composition for either target DNA or control DNA amplification can contain a nucleic acid probe, preferably possessing a detectable label.

Nucleic Acid Hybridization Methods

In addition to primer-directed amplification assay methods, nucleic acid hybridization assay methods can be employed in the present invention for detection of STEC bacteria. The basic components of a nucleic acid hybridization test include a probe, a sample suspected of containing STEC bacteria, and a specific hybridization method. Typically the probe length can vary from as few as 5 bases to the full length of the diagnostic sequence and will depend upon the specific test to be done. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Probes particularly useful in nucleic acid hybridization methods are any of SEQ ID NOs: 1-696, or sequences derived therefrom.

The sample may or may not contain STEC bacteria. The sample may take a variety of forms, however will generally be extracted from an animal, environmental or food source suspected of contamination. The DNA may be detected directly but most preferably, the sample nucleic acid must be made available to contact the probe before any hybridization of probe and target molecule can occur. Thus the organism's DNA is preferably free from the cell and placed under the proper conditions before hybridization can occur. Methods of in-solution hybridization necessitate the purification of the DNA in order to be able to obtain hybridization of the sample DNA with the probe. This has meant that utilization of the in-solution method for detection of target sequences in a sample requires that the nucleic acids of the sample must first be purified to eliminate protein, lipids, and other cell components, and then contacted with the probe under hybridization conditions. Methods for the purification of the sample nucleic acid are common and well known in the art (Sambrook et al., supra).

In one preferred embodiment, hybridization assays may be conducted directly on cell lysates, without the need to extract the nucleic acids. This eliminates several steps from the sample-handling process and speeds up the assay. To perform such assays on crude cell lysates, a chaotropic agent is typically added to the cell lysates prepared as described above. The chaotropic agent stabilizes nucleic acids by inhibiting nuclease activity. Furthermore, the chaotropic agent allows sensitive and stringent hybridization of short oligonucleotide probes to DNA at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30-50% (v/v).

Alternatively, one can purify the sample nucleic acids prior to probe hybridization. A variety of methods are known to one of skill in the art (e.g., phenol-chloroform extraction, Isoquick extraction (MicroProbe Corp., Bothell, Wash.), and others). Pre-hybridization purification is particularly useful for standard filter hybridization assays. Furthermore, purification facilitates measures to increase the assay sensitivity by incorporating in vitro RNA amplification methods such as self-sustained sequence replication (see for example Fahy et al., In *PCR Methods and Applications*, Cold Spring Harbor Laboratory: Cold Spring Harbor, N.Y. (1991), pp. 25-33) or reverse transcriptase PCR (Kawasaki, In *PCR Protocols: A Guide to Methods and Applications*, M. A. Innis et al., Eds., (1990), pp. 21-27).

Once the DNA is released, it can be detected by any of a variety of methods. However, the most useful embodiments have at least some characteristics of speed, convenience, sensitivity, and specificity.

Hybridization methods are well known in the art. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed.

Various hybridization solutions can be employed. Typically, these comprise from about 20 to 60% volume, preferably 30%, of a polar organic solvent. A common hybridization solution employs about 30-50% v/v formamide, about 0.15 to 1M sodium chloride, about 0.05 to 0.1 M buffers, such as sodium citrate, Tris-HCl, PIPES or HEPES (pH range about 6-9), about 0.05 to 0.2% detergent, such as sodium dodecylsulfate, or between 0.5-20 mM EDTA, FICOLL (Pharmacia Inc.) (about 300-500 kilodaltons), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents which include a variety of polar water-soluble or swellable agents (e.g., polyethylene glycol), anionic polymers (e.g., polyacrylate or polymethylacrylate), and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the DNA sequence.

The sandwich assay may be encompassed in an assay kit. This kit would include a first component for the collection of samples suspected of contamination and buffers for the disbursement and lysis of the sample. A second component would include media in either dry or liquid form for the hybridization of target and probe polynucleotides, as well as for the removal of undesirable and nonduplexed forms by washing. A third component includes a solid support (dipstick) upon which is fixed (or to which is conjugated)

unlabeled nucleic acid probe(s) that is (are) complementary to one or more targets of interest, for instance one or more of SEQ ID NOs: 686-696. A fourth component would contain labeled probe that is complementary to a second and different region of the same DNA strand to which the immobilized, unlabeled nucleic acid probe of the third component is hybridized.

In a preferred embodiment, SEQ ID NOs: 1-685 or derivations thereof may be used as 3' blocked detection probes in either a homogeneous or heterogeneous assay format. For example, a probe generated from these sequences may be 3' blocked or non-participatory and will not be extended by, or participate in, a nucleic acid amplification reaction. Additionally, the probe incorporates a label that can serve as a reactive ligand that acts as a point of attachment for the immobilization of the probe/analyte hybrid or as a reporter to produce detectable signal. Accordingly, genomic or cDNA isolated from a sample suspected of $E.\ coli$ contamination is amplified by standard primer-directed amplification protocols in the presence of an excess of the 3' blocked detection probe to produce amplification products. Because the probe is 3' blocked, it does not participate or interfere with the amplification of the target. After the final amplification cycle, the detection probe anneals to the relevant portion of the amplified DNA and the annealed complex is then captured on a support through the reactive ligand.

In some instances it is desirable to incorporate a ligand labeled dNTP, with the label probe in the replication composition to facilitate immobilization of the PCR reaction product on a support and then detection of the immobilized product by means of the labeled probe reagent. For example a biotin, digoxigenin, or digoxin labeled dNTP could be added to PCR reaction composition. The biotin, digoxigenin, or digoxin incorporated in the PCR product could then be immobilized respectively on to a strepavidin, anti-digoxin or antidigoxigenin antibody support. The immobilized PCR product could then be detected by the presence of the probe label.

EXAMPLES

The present invention is further defined in the following Examples. It should be understood that these Examples, while indicating preferred embodiments of the invention, are given by way of illustration only.

Example 1

Determination of Inclusivity/Exclusivity of the Stx, Eae, O157, O45, O103, and O145 Primers and Probes Samples of organisms were analyzed to establish inclusivity and exclusivity of Scorpion® probes of the present invention directed toward stx1/2, eae, O157, O45, O103, and O145 targets. For inclusivity, independent, bona fide STEC isolates appropriate for each assay (O157:H7, O45, O103 and O145, and various other organisms containing $stx_1$, $stx_2$, and eae) were used. For exclusivity, closely related non-target organisms, including other STEC organisms that were not targets of the assays, were used to ensure that the assay would discriminate the target organisms from other non-target organisms.

DNA Lysate Preparation

Material tested was overnight growth pure cultures of the target and non-target organisms grown at 37° C. in BHI media. Pure cultures were grown overnight to cell densities of approximately $1 \times 10^9$ cfu/ml. For exclusivity, non-diluted overnight cultures were tested. For inclusivity, overnight cultures were diluted approximately 1:10,000 into TSB. 20 µl of the material to be tested was added to 200 µl of BAX® lysis reagent (DuPont Qualicon, Wilmington, Del.). The mixture was incubated at 37° C. for 20 minutes, then further incubated at 95° C. for 10 minutes, and finally cooled to 5° C.

PCR Conditions 5-30 µl of the DNA lysate was used to hydrate lyophylized PCR reaction components to obtain DNA lysate/PCR reaction component mixtures. The PCR reaction components included lyophilized reagent tablets containing APTATaq DNA Polymerase (Roche, Mannheim, Germany), deoxynucleotides (Roche Diagnostics, Indianapolis, Ind.), BSA, surfactamps (Sigma-Aldrich, St. Louis, Mo.), and positive control DNA. In addition, the primers, quenchers, and Scorpions® listed in Tables 2 and 3 were included in the amounts provided. For the Scorpion® probes, the 5' end label and linker are also provided in Tables 2 and 3. Each of these Scorpion® probes was designed as a bi-molecular Scorpion®, such that its structure includes (in 5' to 3' order) a 5' fluorescent end label, a probe sequence, an 18-carbon non-amplifiable linker, and a primer sequence. Tables 2 and 3 also list the quenching label that was attached to the 3' terminus of the corresponding quencher oligonucleotides.

TABLE 2

Nucleic acid primers, probes, and quenchers used for inclusivity and exclusivity testing

| | | | | | For Scorpions | | |
| --- | --- | --- | --- | --- | --- | --- | --- |
| Nucleotide Name | Target | Amt. Per Reaction | SEQ ID NO: | End Label | Primer SEQ ID NO: | Internal Label/ Linker | Probe SEQ ID NO: |
| Scorpion O45A-807B | O45 | 20-250 nM | | Cal Fluor Red 610 | 415 | 18-Carbon Spacer | 431 |
| Forward primer O45A807-24 | O45 | 100-500 nM | 423 | | | | |
| Quencher O45A-807B | O45 | 100-1300 nM | 447 | BHQ2 | | | |
| Reverse Primer O45Arc901-24 | O45 | 100-250 nM | 472 | | | | |
| Scorpion | O103 | 20-250 | | Cal | 490 | 18- | 505 |

TABLE 2-continued

Nucleic acid primers, probes, and quenchers used for inclusivity and exclusivity testing

| Nucleotide Name | Target | Amt. Per Reaction | SEQ ID NO: | End Label | For Scorpions Primer SEQ ID NO: | Internal Label/ Linker | Probe SEQ ID NO: |
|---|---|---|---|---|---|---|---|
| O103A-rc851 | | nM | | Fluor Gold 540 | | Carbon Spacer | |
| Forward Primer O103Arc851-22 | O103 | 100-500 nM | 490 | | | | |
| Quencher O103A-rc851 | O103 | 100-1300 nM | 520 | BHQ1 | | | |
| Reverse Primer O103A707-24 | O103 | 100-250 nM | 547 | | | | |
| Scorpion O145A-rc713 | O145 | 20-250 nM | | Quasar 670 | 565 | 18- Carbon Spacer | 580 |
| Forward Primer O145Arc713-22 | O145 | 100-500 nM | 565 | | | | |
| Quencher O145A-rc713 | O145 | 100-1300 nM | 595 | BHQ2 | | | |
| Reverse Primer O145A620-22 | O145 | 100-250 nM | 610 | | | | |
| Scorpion (Unimolecular) SV40 scorpion 1 | Pos. Control | 10-100 nM | | Tamra | 697 | BHQ2/ 18- Carbon Linker | 699 |
| Forward Primer SV4312 | Pos. Control | 25-150 nM | 698 | | | | |
| Reverse Primer SV4222 | Pos. Control | 100-400 nM | 700 | | | | |

TABLE 3

Nucleic acid primers, probes, and quenchers used for inclusivity and exclusivity testing

| Nucleotide Name | Target | Amt. Per reaction | SEQ ID NO: | End Label | For Scorpions Primer SEQ ID NO: | Internal Label/ Linker | Probe SEQ ID NO: |
|---|---|---|---|---|---|---|---|
| Scorpion O157i-rc478 | O157 | 20-250 nM | | Cal Fluor Gold 540 | 625 | 18- Carbon Spacer | 641 |
| Quencher #3 O157i rc478 | O157 | 100-1300 nM | 661 | BHQ1 | | | |
| Forward Primer O157irc478-26 | O157 | 100-500 nM | 625 | | | | |
| Reverse Primer O157i346-23 | O157 | 100-500 nM | 678 | | | | |
| Scorpion Stx1A-rc203B | Stx1A | 20-250 nM | | Cal Fluor Red 610 | 8 | 18- Carbon Spacer | 23 |
| Quencher Stx1A-rc203B | Stx1A | 100-1300 nM | 38 | BHQ2 | | | |
| Forward Primer Stx1A-rc203 | Stx1A | 100-500 nM | 8 | | | | |
| Reverse Primer Stx1A114-27 | Stx1A | 100-500 nM | 65 | | | | |
| Scorpion stx2A-rc650 | Stx2A | 20-250 nM | | Cal Fluor Red 610 | 81 | 18- Carbon Spacer | 96 |
| Quencher stx2A-rc650 | Stx2A | 100-1300 nM | 112 | BHQ2 | | | |
| Forward Primer stx2Arc650-24 | Stx2A | 100-500 nM | 81 | | | | |

TABLE 3-continued

Nucleic acid primers, probes, and quenchers used for inclusivity and exclusivity testing

| Nucleotide Name | Target | Amt. Per reaction | SEQ ID NO: | End Label | For Scorpions Primer SEQ ID NO: | Internal Label/ Linker | Probe SEQ ID NO: |
|---|---|---|---|---|---|---|---|
| Reverse Primer Stx2A594-26 | Stx2A | 100-500 nM | 135 | | | | |
| Scorpion EAE-rc745 | EAE | 20-250 nM | | Quasar 670 | 152 | 18-Carbon Spacer | 167 |
| Quencher EAE-rc745 | EAE | 100-1300 nM | 183 | BHQ2 | | | |
| Forward Primer EAErc745-24 | EAE | 100-500 nM | 152 | | | | |
| Reverse Primer EAE685-29 | EAE | 100-500 nM | 198 | | | | |
| Scorpion (Unimolecular) SV40 scorpion 1 | Pos. Control | 10-100 nM | | Tamra | 697 | BHQ2/ 18-Carbon Linker | 699 |
| Forward Primer SV4312 | Pos. Control | 25-150 nM | 698 | | | | |
| Reverse Primer SV4222 | Pos. Control | 100-400 nM | 700 | | | | |

Amplification and testing were performed on the BAX® Q7 instrument (DuPont Qualicon, Wilmington, Del.). The thermal cycling conditions were as follows: 2 minutes at 94° C., followed by 43 cycles of 94° C. for 10 seconds and 63° C. for 40 seconds, with the fluorescent signal captured during the 63° C. step at each cycle.

Results

As can be seen in Tables 4 through 7, the individual Scorpion® probes were each able to distinguish the various targets from non-targets.

TABLE 4

O45, O103, and O145 inclusivity

| Sample ID | Source | O-Type | BAX ® System Result O45 | O103 | O145 |
|---|---|---|---|---|---|
| R62 | MSU | O45 | Positive | Negative | Negative |
| R63 | MSU | O45 | Positive | Negative | Negative |
| R64 | MSU | O45 | Positive | Negative | Negative |
| R66 | MSU | O103 | Negative | Positive | Negative |
| R67 | MSU | O103 | Negative | Positive | Negative |
| R68 | MSU | O103 | Negative | Positive | Negative |
| R77 | MSU | O145 | Negative | Negative | Positive |
| R78 | MSU | O145 | Negative | Negative | Positive |
| R79 | MSU | O145 | Negative | Negative | Positive |
| R80 | MSU | O145 | Negative | Negative | Positive |
| R163 | USDA-MARC | O103 | Negative | Positive | Negative |
| R164 | USDA-MARC | O103 | Negative | Positive | Negative |
| R165 | USDA-MARC | O103 | Negative | Positive | Negative |
| R166 | USDA-MARC | O103 | Negative | Positive | Negative |
| R167 | USDA-MARC | O103 | Negative | Positive | Negative |
| R168 | USDA-MARC | O103 | Negative | Positive | Negative |
| R198 | USDA-MARC | O145 | Negative | Negative | Positive |
| DD2439 | DuPont | O145 | Negative | Negative | Positive |
| DD2450 | DuPont | O45 | Positive | Negative | Negative |
| DD2483 | DuPont | O145 | Negative | Negative | Positive |
| DD2521 | DuPont | O103 | Negative | Positive | Negative |
| DD2526 | DuPont | O145 | Negative | Negative | Positive |
| DD2530 | DuPont | O103 | Negative | Positive | Negative |
| DD13349 | USDA-ARS | O45 | Positive | Negative | Negative |
| DD13350 | USDA-ARS | O45 | Positive | Negative | Negative |
| DD13351 | USDA-ARS | O45 | Positive | Negative | Negative |
| DD13352 | USDA-ARS | O45 | Positive | Negative | Negative |
| DD13353 | USDA-ARS | O45 | Positive | Negative | Negative |
| DD13354 | USDA-ARS | O45 | Positive | Negative | Negative |
| DD13355 | USDA-ARS | O45 | Positive | Negative | Negative |
| DD13358 | USDA-ARS | O45 | Positive | Negative | Negative |
| DD13359 | USDA-ARS | O45 | Positive | Negative | Negative |
| DD13360 | USDA-ARS | O45 | Positive | Negative | Negative |
| DD13361 | USDA-ARS | O45 | Positive | Negative | Negative |
| DD13373 | USDA-ARS | O103 | Negative | Positive | Negative |
| DD13374 | USDA-ARS | O103 | Negative | Positive | Negative |
| DD13375 | USDA-ARS | O103 | Negative | Positive | Negative |
| DD13376 | USDA-ARS | O103 | Negative | Positive | Negative |
| DD13377 | USDA-ARS | O103 | Negative | Positive | Negative |
| DD13378 | USDA-ARS | O103 | Negative | Positive | Negative |
| DD13379 | USDA-ARS | O103 | Negative | Positive | Negative |
| DD13380 | USDA-ARS | O103 | Negative | Positive | Negative |
| DD13381 | USDA-ARS | O103 | Negative | Positive | Negative |
| DD13382 | USDA-ARS | O103 | Negative | Positive | Negative |
| DD13383 | USDA-ARS | O103 | Negative | Positive | Negative |
| DD13384 | USDA-ARS | O103 | Negative | Positive | Negative |
| DD13385 | USDA-ARS | O103 | Negative | Positive | Negative |
| DD13386 | USDA-ARS | O103 | Negative | Positive | Negative |
| DD13387 | USDA-ARS | O103 | Negative | Positive | Negative |
| DD13388 | USDA-ARS | O103 | Negative | Positive | Negative |
| DD13389 | USDA-ARS | O103 | Negative | Positive | Negative |
| DD13390 | USDA-ARS | O145 | Negative | Negative | Positive |
| DD13391 | USDA-ARS | O145 | Negative | Negative | Positive |
| DD13392 | USDA-ARS | O145 | Negative | Negative | Positive |
| DD13393 | USDA-ARS | O145 | Negative | Negative | Positive |
| DD13394 | USDA-ARS | O145 | Negative | Negative | Positive |
| DD13395 | USDA-ARS | O145 | Negative | Negative | Positive |

TABLE 4-continued

O45, O103, and O145 inclusivity

| Sample ID | Source | O-Type | BAX ® System Result O45 | O103 | O145 |
|---|---|---|---|---|---|
| DD13397 | USDA-ARS | O145 | Negative | Negative | Positive |
| DD13398 | USDA-ARS | O145 | Negative | Negative | Positive |

TABLE 5

O157:H7, stx, and eae inclusivity

| Sample ID | Source | O-Type | BAX ® System Result stx$_1$ and/or stx$_2$ | eae |
|---|---|---|---|---|
| TD8136 | DuPont | O157:H7 | Positive | Positive |
| MA6 | DuPont | O157:H7 | Positive | Positive |
| 493/89 | DuPont | O157:H7 | Positive | Positive |
| R81 | MDP04-01392 | O-:H52 | Positive | Positive |
| R88 | MDP06-00245 | O141:H38 | Positive | Positive |
| DD1450 | DuPont | O157:H7 | Positive | Positive |
| DD2530 | DuPont | O103:H2 | Positive | Positive |
| DD12787 | DuPont | O157:H7 | Negative | Positive |
| DD13040 | DuPont | O157:H7 | Negative | Positive |
| DD13469 | DuPont | O157:H7 | Positive | Positive |
| DD640 | DuPont | O157:H7 | Positive | Positive |
| DD642 | DuPont | O157:H7 | Positive | Positive |
| DD1385 | DuPont | O157:H7 | Positive | Positive |
| DD12797 | DuPont | O157:H7 | Positive | Positive |
| DD1452 | DuPont | O157:H7 | Positive | Positive |
| DD1460 | DuPont | O157:H7 | Positive | Positive |
| DD1461 | DuPont | O157:H7 | Positive | Positive |
| DD1972 | DuPont | O157:H7 | Positive | Positive |
| DD1976 | DuPont | O157:H7 | Positive | Positive |
| DD1977 | DuPont | O157:H7 | Positive | Positive |
| DD1979 | DuPont | O157:H7 | Positive | Positive |
| DD1982 | DuPont | O157:H7 | Positive | Positive |
| DD1987 | DuPont | O157:H7 | Positive | Positive |
| DD1988 | DuPont | O157:H7 | Positive | Positive |
| DD1989 | DuPont | O157:H7 | Positive | Positive |
| DD1991 | DuPont | O157:H7 | Positive | Positive |
| DD5896 | DuPont | O157:H7 | Positive | Positive |
| DD7101 | DuPont | O157:H7 | Positive | Positive |
| DD8295 | DuPont | O157:H7 | Positive | Positive |
| DD8300 | DuPont | O157:H7 | Positive | Positive |
| DD8856 | DuPont | O157:H7 | Positive | Positive |
| DD8865 | DuPont | O157:H7 | Positive | Positive |
| DD8872 | DuPont | O157:H7 | Positive | Positive |
| DD8873 | DuPont | O157:H7 | Positive | Positive |
| DD10133 | DuPont | O157:H7 | Positive | Positive |
| DD10901 | DuPont | O157:H7 | Positive | Positive |
| DD10911 | DuPont | O157:H7 | Positive | Positive |
| DD12817 | DuPont | O157:H7 | Positive | Positive |
| DD12901 | DuPont | O157:H7 | Positive | Positive |
| DD13038 | DuPont | O157:H7 | Positive | Positive |
| DD10920 | DuPont | O157:H7 | Positive | Positive |
| DD10921 | DuPont | O157:H7 | Positive | Positive |
| DD12807 | DuPont | O157:H7 | Positive | Positive |
| DD13054 | DuPont | O157:H7 | Positive | Positive |
| DD13055 | DuPont | O157:H7 | Positive | Positive |
| DD13072 | DuPont | O157:H7 | Positive | Positive |
| DD13077 | DuPont | O157:H7 | Positive | Positive |
| DD13078 | DuPont | O157:H7 | Positive | Positive |
| DD13174 | DuPont | O157:H7 | Positive | Positive |
| DD13175 | DuPont | O157:H7 | Positive | Positive |
| DD13176 | DuPont | O157:H7 | Positive | Positive |
| DD13182 | DuPont | O157:H7 | Positive | Positive |
| DD13189 | DuPont | O157:H7 | Positive | Positive |
| DD13190 | DuPont | O157:H7 | Positive | Positive |
| DD13196 | DuPont | O157:H7 | Positive | Positive |
| DD13197 | DuPont | O157:H7 | Positive | Positive |
| DD13199 | DuPont | O157:H7 | Positive | Positive |
| DD13241 | DuPont | O157:H7 | Positive | Positive |
| DD13262 | DuPont | O157:H7 | Positive | Positive |

TABLE 6

Non-*E. coli* exclusivity

| Sample ID | Source | Organism | BAX ® System Result O45 | O103 | O145 | stx$_1$ and/or stx$_2$ | eae | O157: H7 |
|---|---|---|---|---|---|---|---|---|
| DD373 | DuPont | *Klebsiella pneumoniae* | Neg. | Neg. | Neg. | Neg. | Neg. | Neg. |
| DD374 | DuPont | *Proteus mirabilis* | Neg. | Neg. | Neg. | Neg. | Neg. | Neg. |
| DD383 | DuPont | *Citrobacter freundii* | Neg. | Neg. | Neg. | Neg. | Neg. | Neg. |
| DD657 | DuPont | *Klebsiella ozaenae* | Neg. | Neg. | Neg. | Neg. | Neg. | Neg. |
| DD658 | DuPont | *Klebsiella oxytoca* | Neg. | Neg. | Neg. | Neg. | Neg. | Neg. |
| DD2389 | DuPont | *Hafnia alvei* | Neg. | Neg. | Neg. | Neg. | Neg. | Neg. |
| DD2417 | DuPont | *Serratia liquefaciens* | Neg. | Neg. | Neg. | Neg. | Neg. | Neg. |
| DD2558 | DuPont | *Citrobacter freundii* | Neg. | Neg. | Neg. | Neg. | Neg. | Neg. |
| DD3064 | DuPont | *Morganella morganii* | Neg. | Neg. | Neg. | Neg. | Neg. | Neg. |
| DD3982 | DuPont | *Pseudomonas aeruginosa* | Neg. | Neg. | Neg. | Neg. | Neg. | Neg. |
| DD5588 | DuPont | *Hafnia alvei* | Neg. | Neg. | Neg. | Neg. | Neg. | Neg. |
| DD6121 | DuPont | Gram negative rod | Neg. | Neg. | Neg. | Neg. | Neg. | Neg. |
| DD7083 | DuPont | Unknown | Neg. | Neg. | Neg. | Neg. | Neg. | Neg. |
| DD13142 | DuPont | *Morganella morganii* | Neg. | Neg. | Neg. | Neg. | Neg. | Neg. |

TABLE 6-continued

Non-*E. coli* exclusivity

| | | | BAX ® System Result | | | | | |
|---|---|---|---|---|---|---|---|---|
| Sample ID | Source | Organism | O45 | O103 | O145 | stx$_1$ and/or stx$_2$ | eae | O157: H7 |
| DD13147 | DuPont | *Providencia rettgeri* | Neg. | Neg. | Neg. | Neg. | Neg. | Neg. |
| DD13148 | DuPont | *Pseudomonas aeruginosa* | Neg. | Neg. | Neg. | Neg. | Neg. | Neg. |
| DD13186 | DuPont | *Enterobacter amnigenus* | Neg. | Neg. | Neg. | Neg. | Neg. | Neg. |
| DD13187 | DuPont | *Enterobacter amnigenus* | Neg. | Neg. | Neg. | Neg. | Neg. | Neg. |
| DD13094 | DuPont | *Enterobacter sakazakii* | Neg. | Neg. | Neg. | Neg. | Neg. | Neg. |
| DD13099 | DuPont | *Enterobacter sakazakii* | Neg. | Neg. | Neg. | Neg. | Neg. | Neg. |
| DD13134 | DuPont | *Enterobacter sakazakii* | Neg. | Neg. | Neg. | Neg. | Neg. | Neg. |
| DD13135 | DuPont | *Enterobacter cloacae* | Neg. | Neg. | Neg. | Neg. | Neg. | Neg. |
| DD13151 | DuPont | *Escherichia hermanii* | Neg. | Neg. | Neg. | Neg. | Neg. | Neg. |
| DD13162 | DuPont | *Enterobacter hormaechei* | Neg. | Neg. | Neg. | Neg. | Neg. | Neg. |
| DD13163 | DuPont | *Enterobacter turicensis* | Neg. | Neg. | Neg. | Neg. | Neg. | Neg. |
| DD13161 | DuPont | *Enterobacter asburiae* | Neg. | Neg. | Neg. | Neg. | Neg. | Neg. |
| DD1535 | DuPont | *Salmonella* | Neg. | Neg. | Neg. | Neg. | Neg. | Neg. |
| DD1774 | DuPont | *Salmonella diarazoniae* | Neg. | Neg. | Neg. | Neg. | Neg. | Neg. |

TABLE 7

*E. coli* exclusivity

| | | | BAX ® System Results | | | | | |
|---|---|---|---|---|---|---|---|---|
| Sample ID | Location | O type | O45 | O103 | O145 | stx$_1$ and/or stx$_2$ | eae | O157:H7 |
| R61 | MSU | O45 | Pos. | Neg. | Neg. | nt | nt | nt |
| R65 | MSU | O103 | Neg. | Pos. | Neg. | nt | nt | nt |
| R77 | MSU | O145 | Neg. | Neg. | Pos. | nt | nt | nt |
| DD640 | DuPont | O157 | Neg. | Neg. | Neg. | nt | nt | nt |
| DD641 | DuPont | O157 | Neg. | Neg. | Neg. | nt | nt | nt |
| DD1718 | DuPont | O128 | Neg. | Neg. | Neg. | Neg. | Pos. | Neg. |
| DD1721 | DuPont | O114 | Neg. | Neg. | Neg. | Neg. | Neg. | Neg. |
| DD1730 | DuPont | O86 | Neg. | Neg. | Neg. | Neg. | Neg. | Neg. |
| DD1732 | DuPont | O143 | Neg. | Neg. | Neg. | Neg. | Neg. | Neg. |
| DD1762 | DuPont | O164 | Neg. | Neg. | Neg. | Neg. | Neg. | Neg. |
| DD1769 | DuPont | O139 | Neg. | Neg. | Neg. | Pos. | Neg. | Neg. |
| DD1770 | DuPont | O115 | Neg. | Neg. | Neg. | Neg. | Neg. | Neg. |
| DD1803 | DuPont | O25 | Neg. | Neg. | Neg. | Neg. | Neg. | Neg. |
| DD1814 | DuPont | O6 | Neg. | Neg. | Neg. | Pos. | Neg. | Neg. |
| DD1821 | DuPont | O55 | Neg. | Neg. | Neg. | Neg. | Neg. | Neg. |
| DD1827 | DuPont | O20 | Neg. | Neg. | Neg. | Neg. | Neg. | Neg. |
| DD1835 | DuPont | O127 | Neg. | Neg. | Neg. | Neg. | Neg. | Neg. |
| DD1836 | DuPont | O125 | Neg. | Neg. | Neg. | Neg. | Neg. | Neg. |
| DD1842 | DuPont | O78 | Neg. | Neg. | Neg. | Neg. | Neg. | Neg. |
| DD1861 | DuPont | O126 | Neg. | Neg. | Neg. | Neg. | Neg. | Neg. |
| DD1889 | DuPont | O152 | Neg. | Neg. | Neg. | Neg. | Neg. | Neg. |
| DD1915 | DuPont | O28 | Neg. | Neg. | Neg. | Neg. | Neg. | Neg. |
| DD2432 | DuPont | O165 | Neg. | Neg. | Neg. | Neg. | Neg. | Neg. |
| DD2434 | DuPont | O1 | Neg. | Neg. | Neg. | Neg. | Neg. | Neg. |
| DD2438 | DuPont | O118 | Neg. | Neg. | Neg. | Neg. | Neg. | Neg. |
| DD2441 | DuPont | O117 | Neg. | Neg. | Neg. | Neg. | Neg. | Neg. |
| DD2445 | USDA | O113 | Neg. | Neg. | Neg. | Neg. | Neg. | Neg. |
| DD2480 | USDA | O4 | Neg. | Neg. | Neg. | Neg. | Neg. | Neg. |
| DD3124 | USDA | O2 | Neg. | Neg. | Neg. | Neg. | Neg. | Neg. |
| DD3130 | USDA | O8 | Neg. | Neg. | Neg. | Neg. | Neg. | Neg. |
| DD5884 | USDA | O91 | Neg. | Neg. | Neg. | Pos. | Neg. | Neg. |
| DD13415 | USDA | O165 | Neg. | Neg. | Neg. | Pos. | Pos. | Neg. |
| DD13417 | USDA | O4 | Neg. | Neg. | Neg. | Pos. | Pos. | Neg. |
| DD13418 | USDA | O14 | Neg. | Neg. | Neg. | Pos. | Pos. | Neg. |
| DD13419 | USDA | O22 | Neg. | Neg. | Neg. | Pos. | Neg. | Neg. |
| DD13420 | USDA | O28 | Neg. | Neg. | Neg. | Pos. | Neg. | Neg. |
| DD13421 | USDA | O38 | Neg. | Neg. | Neg. | Pos. | Neg. | Neg. |
| DD13422 | USDA | O48 | Neg. | Neg. | Neg. | Pos. | Neg. | Neg. |
| DD13423 | USDA | O79 | Neg. | Neg. | Neg. | Pos. | Neg. | Neg. |
| DD13424 | USDA | O83 | Neg. | Neg. | Neg. | Pos. | Pos. | Neg. |
| DD13425 | USDA | O88 | Neg. | Neg. | Neg. | Pos. | Neg. | Neg. |
| DD13426 | USDA | O93 | Neg. | Neg. | Neg. | Pos. | Neg. | Neg. |
| DD13427 | USDA | O104 | Neg. | Neg. | Neg. | Pos. | Neg. | Neg. |
| DD13428 | USDA | O117 | Neg. | Neg. | Neg. | Pos. | Neg. | Neg. |
| DD13429 | USDA | O119 | Neg. | Neg. | Neg. | Pos. | Neg. | Neg. |
| DD13430 | USDA | O125 | Neg. | Neg. | Neg. | Pos. | Pos. | Neg. |
| DD13431 | USDA | O126 | Neg. | Neg. | Neg. | Pos. | Neg. | Neg. |
| DD13432 | USDA | O128 | Neg. | Neg. | Neg. | Pos. | Neg. | Neg. |
| DD13433 | USDA | O137 | Neg. | Neg. | Neg. | Pos. | Neg. | Neg. |
| DD13434 | USDA | O146 | Neg. | Neg. | Neg. | Pos. | Neg. | Neg. |
| DD13435 | USDA | O165 | Neg. | Neg. | Neg. | Pos. | Pos. | Neg. |
| DD13436 | USDA | OX3 | Neg. | Neg. | Neg. | Pos. | Neg. | Neg. |
| DD13437 | USDA | O113 | Neg. | Neg. | Neg. | Pos. | Neg. | Neg. |
| DD13438 | USDA | O165 | Neg. | Neg. | Neg. | Pos. | Pos. | Neg. |
| DD13439 | USDA | O5 | Neg. | Neg. | Neg. | Pos. | Pos. | Neg. |
| DD13440 | USDA | O55 | Neg. | Neg. | Neg. | Pos. | Pos. | Neg. |
| DD13441 | USDA | O91 | Neg. | Neg. | Neg. | Pos. | Neg. | Neg. |
| DD13442 | USDA | O2 | Neg. | Neg. | Neg. | Pos. | Neg. | Neg. |
| DD13443 | USDA | O2 | Neg. | Neg. | Neg. | Pos. | Neg. | Neg. |
| DD13444 | USDA | O2 | Neg. | Neg. | Neg. | Pos. | Neg. | Neg. |
| DD13445 | USDA | O128 | Neg. | Neg. | Neg. | Pos. | Neg. | Neg. |
| DD13446 | USDA | O128 | Neg. | Neg. | Neg. | Pos. | Neg. | Neg. |
| DD13447 | USDA | O63 | Neg. | Neg. | Neg. | Neg. | Pos. | Neg. |
| DD13448 | USDA | O63 | Neg. | Neg. | Neg. | Pos. | Pos. | Neg. |

TABLE 7-continued

E. coli exclusivity

| | | BAX ® System Results | | | | | |
|---|---|---|---|---|---|---|---|
| Sample ID | O Location type | O45 | O103 | O145 | stx$_1$ and/or stx$_2$ | eae | O157:H7 |
| DD13449 | USDA O63 | Neg. | Neg. | Neg. | Pos. | Neg. | Neg. |
| DD13450 | USDA O113 | Neg. | Neg. | Neg. | Pos. | Neg. | Neg. |
| DD13451 | USDA O113 | Neg. | Neg. | Neg. | Pos. | Neg. | Neg. |
| DD13452 | USDA O113 | Neg. | Neg. | Neg. | Pos. | Neg. | Neg. |
| DD13453 | USDA O91 | Neg. | Neg. | Neg. | Pos. | Neg. | Neg. |
| DD13454 | USDA O91 | Neg. | Neg. | Neg. | Pos. | Neg. | Neg. |
| DD13455 | USDA O2 | Neg. | Neg. | Neg. | Neg. | Pos. | Neg. |
| DD13456 | USDA O2 | Neg. | Neg. | Neg. | Pos. | Pos. | Neg. |
| DD13457 | USDA O2 | Neg. | Neg. | Neg. | Pos. | Neg. | Neg. |
| DD13458 | USDA O174 | Neg. | Neg. | Neg. | Pos. | Neg. | Neg. |
| DD13459 | USDA O55 | Neg. | Neg. | Neg. | Pos. | Pos. | Neg. |
| DD13460 | USDA O128 | Neg. | Neg. | Neg. | Neg. | Pos. | Neg. |
| DD13461 | USDA O177 | Neg. | Neg. | Neg. | Pos. | Pos. | Neg. |
| DD13462 | USDA O111 | Neg. | Neg. | Neg. | Pos. | Pos. | Neg. |
| DD13463 | USDA O113 | Neg. | Neg. | Neg. | Pos. | Neg. | Neg. |
| DD13464 | USDA O103 | Neg. | Pos. | Neg. | Pos. | Pos. | Neg. |
| DD13465 | USDA O26 | Neg. | Neg. | Neg. | Pos. | Pos. | Neg. |
| DD13466 | USDA O41 | Neg. | Neg. | Neg. | Pos. | Pos. | Neg. | nt = not tested

Example 2

Determination of Inclusivity/Exclusivity of the O26, O111, and O121 Primers and Probes As O26, O111, and O121 are additional strains of STEC bacteria, samples of organisms were analyzed to establish inclusivity and exclusivity of a multiplex of O26, O111, and O121 Scorpion® probes of the present invention. For inclusivity, independent, bona fide E. coli O26, O111, and O121 isolates were used. For exclusivity, non-E. coli species and E. coli that did not belong to any of these three serotypes were used to ensure that the assay would discriminate the target organisms (O26, O111, and O121) from other bacteria.

DNA Lysate Preparation

DNA lysates were prepare using the methodology described in Example 1

PCR Conditions

30 μl of the DNA lysate was used to hydrate lyophilized PCR reaction components to achieve a DNA lysate/PCR reaction component mixture as described in Example 1. The primers and probes listed in Table 8 were included in the amounts provided. For the Scorpion® probes, the 5' end label, internal label, and linker are also provided in Table 8. Each of these Scorpion® probes was designed as a unimolecular Scorpion®, such that its structure includes (in 5' to 3' order) a 5' fluorescent end label, a 5' stem sequence, a probe sequence, a 3' stem sequence, an internal quencher, an 18-carbon non-amplifiable linker, and a primer sequence, wherein the 5' and 3' stem sequences are reverse complements of one another such that they form a stem-loop structure that results in quenching of the 5' end label when the probe is not bound to its target.

TABLE 8

Nucleic acid primers, probes, and quenchers used for inclusivity and exclusivity testing

| | | | | For Scorpions | | | |
|---|---|---|---|---|---|---|---|
| Nucleotide Name | Target | Amt. Per reaction | SEQ ID NO: | End Label | Probe SEQ ID NO: | Internal Label/ Linker | Primer SEQ ID NO: |
| Scorpion (Unimolecular) O26A-944 UM02 | O26 | 0.75 pMole | | Cal Fluor Red 610 | 228 | BHQ2/ 18-Carbon Linker | 213 |
| Forward Primer O26A944-29 | O26 | 5.25 pMole | 213 | | | | |
| Reverse Primer O26Arc1070-28 | O26 | 6.0 pMole | 265 | | | | |
| Scorpion (Unimolecular) O111-rc320 UM02 | O111 | 1.5 pMole | | Cal Fluor Gold 540 | 297 | BHQ1/ 18-Carbon Linker | 282 |
| Forward Primer O111Arc320-29 | O111 | 4.5 pMole | 282 | | | | |
| Reverse Primer O111A158-22 | O111 | 6.0 pMole | 334 | | | | |
| Scorpion (Unimolecular) O121A-rc214B UM01 | O121 | 1.5 pMole | | Quasar 670 | 364 | BHQ2/ 18-Carbon Linker | 349 |
| Forward Primer O121A-rc214-22 | O121 | 4.5 pMole | 349 | | | | |
| Reverse Primer O121A90-27 | O121 | 6.0 pMole | 400 | | | | |
| Scorpion (Unimolecular) SV40 scorpion 1 | Pos. Control | 1.05 pMole | | Tamra | 697 | BHQ2/ 18-Carbon Linker | 699 |

TABLE 8-continued

Nucleic acid primers, probes, and quenchers used for inclusivity and exclusivity testing

| Nucleotide Name | Target | Amt. Per reaction | SEQ ID NO: | For Scorpions | | | |
|---|---|---|---|---|---|---|---|
| | | | | End Label | Probe SEQ ID NO: | Internal Label/ Linker | Primer SEQ ID NO: |
| Forward Primer SV4312 | Pos. Control | 2.25 pMole | 698 | | | | |
| Reverse Primer SV4222 | Pos. Control | 4.5 pMole | 700 | | | | |

Amplification and testing were performed on the BAX® Q7 machine (DuPont Qualicon, Wilmington, Del.). The thermal cycling conditions were as follows: 2 minutes at 94° C., followed by 40 cycles of 94° C. for 10 seconds and 63° C. for 40 seconds, with the fluorescent signal captured during the 63° C. step at each cycle.

Results

As is shown in Tables 9-11, using a multiplex of Scorpion® probes, the method of the present invention was able to discriminate O26, O111, and O121 serotypes from non-target strains, including other O-type *E. coli* strains and non-*E. coli* strains (blank results indicate a negative result).

TABLE 9

O26, O111, and O121 inclusivity

| Sample ID | Location | O type | BAX result | | |
|---|---|---|---|---|---|
| | | | O26 | O111 | O121 |
| R58 | MSU | O26 | Pos. | | |
| R59 | MSU | O26 | Pos. | | |
| R60 | MSU | O26 | Pos. | | |
| R70 | MSU | O111 | | Pos. | |
| R71 | MSU | O111 | | Pos. | |
| R72 | MSU | O111 | | Pos. | |
| R75 | MSU | O121 | | | Pos. |
| R76 | MSU | O121 | | | Pos. |
| R84 | MDP | O121 | | | Pos. |
| R144 | MARC | O26 | Pos. | | |
| R184 | MARC | O121 | | | Pos. |
| R185 | MARC | O121 | | | Pos. |
| R186 | MARC | O121 | | | Pos. |
| R187 | MARC | O121 | | | Pos. |
| R188 | MARC | O121 | | | Pos. |
| DD1720 | DD collection | O26 | Pos. | | |

TABLE 9-continued

O26, O111, and O121 inclusivity

| Sample ID | Location | O type | BAX result | | |
|---|---|---|---|---|---|
| | | | O26 | O111 | O121 |
| DD1729 | DD collection | O111 | | Pos. | |
| DD1807 | DD collection | O26 | Pos. | | |
| DD1808 | DD collection | O111 | | Pos. | |
| DD1809 | DD collection | O111 | | Pos. | |
| DD1831 | DD collection | O26 | Pos. | | |
| DD1858 | DD collection | O111 | | Pos. | |
| DD1913 | DD collection | O26 | Pos. | | |
| DD1927 | DD collection | O111 | | Pos. | |
| DD2440 | DD collection | O121 | | | Pos. |
| DD2460 | DD collection | O121 | | | Pos. |
| DD5902 | DD collection | O26 | Pos. | | |
| DD5903 | DD collection | O26 | Pos. | | |
| DD5904 | DD collection | O26 | Pos. | | |
| DD5905 | DD collection | O26 | Pos. | | |
| DD9704 | DD collection | O26 | Pos. | | |
| DD9705 | DD collection | O26 | Pos. | | |
| DD9706 | DD collection | O26 | Pos. | | |
| DD9707 | DD collection | O26 | Pos. | | |
| DD13362 | USDA | O121 | | | Pos. |
| DD13363 | USDA | O121 | | | Pos. |
| DD13364 | USDA | O121 | | | Pos. |
| DD13365 | USDA | O121 | | | Pos. |
| DD13366 | USDA | O121 | | | Pos. |
| DD13367 | USDA | O121 | | | Pos. |
| DD13368 | USDA | O121 | | | Pos. |
| DD13370 | USDA | O121 | | | Pos. |
| DD133400 | USDA | O111 | Pos. | Pos. | |
| DD133401 | USDA | O111 | | Pos. | |
| DD133402 | USDA | O111 | | Pos. | |
| DD133403 | USDA | O111 | | Pos. | |

TABLE 10

Exclusivity to non-*E. coli* species

| Sample ID | Location | Species | BAX result | | |
|---|---|---|---|---|---|
| | | | O26 | O111 | O121 |
| DD373 | DD collection | *Klebsiella pneumoniae* | Negative | Negative | Negative |
| DD374 | DD collection | *Proteus mirabilis* | Negative | Negative | Negative |
| DD383 | DD collection | *Citrobacter freundii* | Negative | Negative | Negative |
| DD657 | DD collection | *Klebsiella ozaenae* | Negative | Negative | Negative |
| DD658 | DD collection | *Klebsiella oxytoca* | Negative | Negative | Negative |
| DD2389 | DD collection | *Hafnia alvei* | Negative | Negative | Negative |
| DD2417 | DD collection | *Serratia liquefaciens* | Negative | Negative | Negative |
| DD2558 | DD collection | *Citrobacter freundii* | Negative | Negative | Negative |
| DD3064 | DD collection | *Morganella morganii* | Negative | Negative | Negative |
| DD3982 | DD collection | *Pseudomonas aeruginosa* | Negative | Negative | Negative |
| DD5588 | DD collection | *Hafnia alvei* | Negative | Negative | Negative |
| DD6121 | DD collection | Gram negative rod | Negative | Negative | Negative |

TABLE 10-continued

Exclusivity to non-E. coli species

| | | | BAX result | | |
|---|---|---|---|---|---|
| Sample ID | Location | Species | O26 | O111 | O121 |
| DD13142 | DD collection | Morganella morganii | Negative | Negative | Negative |
| DD13147 | DD collection | Providencia rettgeri | Negative | Negative | Negative |
| DD13148 | DD collection | Pseudomonas aeruginosa | Negative | Negative | Negative |
| DD13186 | DD collection | Enterobacter amnigenus | Negative | Negative | Negative |
| DD13187 | DD collection | Enterobacter amnigenus | Negative | Negative | Negative |
| DD13094 | DD collection | Enterobacter sakazakii | Negative | Negative | Negative |
| DD13099 | DD collection | Enterobacter sakazakii | Negative | Negative | Negative |
| DD13134 | DD collection | Enterobacter sakazakii | Negative | Negative | Negative |
| DD13135 | DD collection | Enterobacter cloacae | Negative | Negative | Negative |
| DD13151 | DD collection | Escherichia hermanii | Negative | Negative | Negative |
| DD13162 | DD collection | Enterobacter hormaechei | Negative | Negative | Negative |
| DD13163 | DD collection | Enterobacter turicensis | Negative | Negative | Negative |
| DD13161 | DD collection | Enterobacter asburiae | Negative | Negative | Negative |
| DD1535 | DD collection | Salmonella | Negative | Negative | Negative |
| DD1774 | DD collection | Salmonella diarazoniae | Negative | Negative | Negative |

TABLE 11

Exclusivity versus other E. coli o-types

| | | | BAX result | | |
|---|---|---|---|---|---|
| Sample ID | Location | O type | O26 | O111 | O121 |
| R61 | MSU | O45 | Negative | Negative | Negative |
| R65 | MSU | O103 | Negative | Negative | Negative |
| R77 | MSU | O145 | Negative | Negative | Negative |
| DD640 | DD collection | O157 | Negative | Negative | Negative |
| DD641 | DD collection | O157 | Negative | Negative | Negative |
| DD1718 | DD collection | O128 | Negative | Negative | Negative |
| DD1721 | DD collection | O114 | Negative | Negative | Negative |
| DD1730 | DD collection | O86 | Negative | Negative | Negative |
| DD1732 | DD collection | O143 | Negative | Negative | Negative |
| DD1762 | DD collection | O164 | Negative | Negative | Negative |
| DD1769 | DD collection | O139 | Negative | Negative | Negative |
| DD1770 | DD collection | O115 | Negative | Negative | Negative |
| DD1803 | DD collection | O25 | Negative | Negative | Negative |
| DD1814 | DD collection | O6 | Negative | Negative | Negative |
| DD1821 | DD collection | O55 | Negative | Negative | Negative |
| DD1827 | DD collection | O20 | Negative | Negative | Negative |
| DD1835 | DD collection | O127 | Negative | Negative | Negative |
| DD1836 | DD collection | O125 | Negative | Negative | Negative |
| DD1842 | DD collection | O78 | Negative | Negative | Negative |
| DD1861 | DD collection | O126 | Negative | Negative | Negative |
| DD1889 | DD collection | O152 | Negative | Negative | Negative |
| DD1915 | DD collection | O28 | Negative | Negative | Negative |
| DD2432 | DD collection | O165 | Negative | Negative | Negative |
| DD2434 | DD collection | O1 | Negative | Negative | Negative |
| DD2438 | DD collection | O118 | Negative | Negative | Negative |
| DD2441 | DD collection | O117 | Negative | Negative | Negative |
| DD2445 | USDA | O113 | Negative | Negative | Negative |
| DD2480 | USDA | O4 | Negative | Negative | Negative |
| DD3124 | USDA | O2 | Negative | Negative | Negative |
| DD3130 | USDA | O8 | Negative | Negative | Negative |
| DD5884 | USDA | O91 | Negative | Negative | Negative |
| DD13415 | USDA | O165 | Negative | Negative | Negative |
| DD13417 | USDA | O4 | Negative | Negative | Negative |
| DD13418 | USDA | O14 | Negative | Negative | Negative |
| DD13419 | USDA | O22 | Negative | Negative | Negative |
| DD13420 | USDA | O28 | Negative | Negative | Negative |
| DD13421 | USDA | O38 | Negative | Negative | Negative |
| DD13422 | USDA | O48 | Negative | Negative | Negative |
| DD13423 | USDA | O79 | Negative | Negative | Negative |
| DD13424 | USDA | O83 | Positive | Negative | Negative |
| DD13425 | USDA | O88 | Negative | Negative | Negative |
| DD13426 | USDA | O93 | Negative | Negative | Negative |
| DD13427 | USDA | O104 | Negative | Negative | Negative |
| DD13428 | USDA | O117 | Negative | Negative | Negative |
| DD13429 | USDA | O119 | Negative | Negative | Negative |
| DD13430 | USDA | O125 | Negative | Negative | Negative |
| DD13431 | USDA | O126 | Negative | Negative | Negative |
| DD13432 | USDA | O128 | Negative | Negative | Negative |
| DD13433 | USDA | O137 | Negative | Negative | Negative |
| DD13434 | USDA | O146 | Negative | Negative | Negative |
| DD13435 | USDA | O165 | Negative | Negative | Negative |
| DD13436 | USDA | OX3 | Negative | Negative | Negative |
| DD13437 | USDA | O113 | Negative | Negative | Negative |
| DD13438 | USDA | O165 | Negative | Negative | Negative |
| DD13439 | USDA | O5 | Negative | Negative | Negative |
| DD13440 | USDA | O55 | Negative | Negative | Negative |
| DD13441 | USDA | O91 | Negative | Negative | Negative |
| DD13442 | USDA | O2 | Negative | Negative | Negative |
| DD13443 | USDA | O2 | Negative | Negative | Negative |
| DD13444 | USDA | O2 | Negative | Negative | Negative |
| DD13445 | USDA | O128 | Negative | Negative | Negative |
| DD13446 | USDA | O128 | Negative | Negative | Negative |
| DD13447 | USDA | O63 | Negative | Negative | Negative |
| DD13448 | USDA | O63 | Negative | Negative | Negative |
| DD13449 | USDA | O63 | Negative | Negative | Negative |
| DD13450 | USDA | O113 | Negative | Negative | Negative |
| DD13451 | USDA | O113 | Negative | Negative | Negative |
| DD13452 | USDA | O113 | Negative | Negative | Negative |
| DD13453 | USDA | O91 | Negative | Negative | Negative |
| DD13454 | USDA | O91 | Negative | Negative | Negative |
| DD13455 | USDA | O2 | Negative | Negative | Negative |
| DD13456 | USDA | O2 | Negative | Negative | Negative |
| DD13457 | USDA | O2 | Negative | Negative | Negative |
| DD13458 | USDA | O174 | Negative | Negative | Negative |
| DD13459 | USDA | O55 | Negative | Negative | Negative |
| DD13460 | USDA | O128 | Negative | Negative | Negative |
| DD13461 | USDA | O177 | Negative | Negative | Negative |
| DD13462 | USDA | O111 | Negative | Positive | Negative |
| DD13463 | USDA | O113 | Negative | Negative | Negative |
| DD13464 | USDA | O103 | Negative | Negative | Negative |
| DD13465 | USDA | O26 | Positive | Negative | Negative |
| DD13466 | USDA | O41 | Negative | Negative | Negative |

What is claimed is:

1. An isolated polynucleotide comprising a primer-probe complex, wherein said primer probe complex comprises:
   (A) a primer region comprising a nucleic acid sequence comprising at least 15 contiguous nucleotides of SEQ ID NO: 1 and a probe region comprising at least 15 contiguous nucleotides of SEQ ID NO: 16;
   (B) a primer region comprising SEQ ID NO: 48 and a probe region comprising a nucleic acid sequence selected from the group consisting of SEQ ID NOs: 49-52;
   (C) a primer region comprising SEQ ID NO: 55, and a probe region comprising SEQ ID NO: 56;
   (D) a primer region comprising at least 15 contiguous nucleotides of SEQ ID NO: 74 and a probe region comprising at least 15 contiguous nucleotides of SEQ ID NO: 89;
   (E) a primer region comprising SEQ ID NO: 120 and a probe region comprising a nucleic acid sequence selected from the group consisting of SEQ ID NOs: 121-122;
   (F) a primer region comprising SEQ ID NO: 125 and a probe region comprising SEQ ID NO: 126; or
   (G) a primer region comprising at least 15 contiguous nucleotides of SEQ ID NO: 145 and a probe region comprising at least 15 contiguous nucleotides of SEQ ID NO: 160;

wherein said probe region and said primer region each have a 5' and 3' terminus, wherein said 3' terminus of said probe region is attached to said 5' terminus of said primer region via a linker moiety, and wherein said primer-probe complex further comprises a detectable label.

2. A kit for detection of STEC bacteria in a sample, comprising an isolated polynucleotide of claim 1.

3. A reagent tablet comprising an isolated polynucleotide of claim 1.

* * * * *

SEQUENCE LISTING

```
<160> NUMBER OF SEQ ID NOS: 700

<210> SEQ ID NO 1
<211> LENGTH: 39
<212> TYPE: DNA
<213> ORGANISM: Artificial Sequence
<220> FEATURE:
<223> OTHER INFORMATION: Primer/Probe/Quencher Sequence

<400> SEQUENCE: 1
tccctctgac atcaactgca aacaaattat ccccctgtgc                              39

<210> SEQ ID NO 2
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 2
tccctctgac atcaactgca aacaaat                                            27

<210> SEQ ID NO 3
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 3
ccctctgaca tcaactgcaa acaaatt                                            27

<210> SEQ ID NO 4
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 4
cctctgacat caactgcaaa caaatta                                            27

<210> SEQ ID NO 5
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 5
ctctgacatc aactgcaaac aaattat                                            27

<210> SEQ ID NO 6
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 6
tctgacatca actgcaaaca aattatc                                            27

<210> SEQ ID NO 7
<211> LENGTH: 27
<212> TYPE: DNA
<213> ORGANISM: Artificial Sequence
```

```
<220> FEATURE:
<223> OTHER INFORMATION: Primer/Probe/Quencher Sequence

<400> SEQUENCE: 7
ctgacatcaa ctgcaaacaa attatcc                                          27

<210> SEQ ID NO 8
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 8
tgacatcaac tgcaaacaaa ttatccc                                          27

<210> SEQ ID NO 9
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 9
gacatcaact gcaaacaaat tatcccc                                          27

<210> SEQ ID NO 10
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 10
acatcaactg caaacaaatt atcccct                                          27

<210> SEQ ID NO 11
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 11
catcaactgc aaacaaatta tccctg                                           27

<210> SEQ ID NO 12
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 12
atcaactgca aacaaattat ccctgt                                           27

<210> SEQ ID NO 13
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 13
tcaactgcaa acaaattatc ccctgtg                                          27
```

<210> SEQ ID NO 14
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 14
caactgcaaa caaattatcc cctgtgc                                27

<210> SEQ ID NO 15
<211> LENGTH: 21
<212> TYPE: DNA
<213> ORGANISM: Artificial Sequence
<220> FEATURE:
<223> OTHER INFORMATION: Primer/Probe/Quencher Sequence

<400> SEQUENCE: 15
catcaactgc aaacaaatta t                                      21

<210> SEQ ID NO 16
<211> LENGTH: 45
<212> TYPE: DNA
<213> ORGANISM: Artificial Sequence
<220> FEATURE:
<223> OTHER INFORMATION: Primer/Probe/Quencher Sequence

<400> SEQUENCE: 16
ttcatcagga ggtacgtctt tactgatgat tgatagtggc acagg            45

<210> SEQ ID NO 17
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 17
ttcatcagga ggtacgtctt tactgatgat tga                         33

<210> SEQ ID NO 18
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 18
tcatcaggag gtacgtcttt actgatgatt gat                         33

<210> SEQ ID NO 19
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 19
catcaggagg tacgtcttta ctgatgattg ata                         33

<210> SEQ ID NO 20
<211> LENGTH: 33
<212> TYPE: DNA
<213> ORGANISM: Artificial Sequence
<220> FEATURE:
<223> OTHER INFORMATION: Primer/Probe/Quencher Sequence -continued

<400> SEQUENCE: 20
atcaggaggt acgtctttac tgatgattga tag                                    33

<210> SEQ ID NO 21
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 21
tcaggaggta cgtctttact gatgattgat agt                                    33

<210> SEQ ID NO 22
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 22
caggaggtac gtctttactg atgattgata gtg                                    33

<210> SEQ ID NO 23
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 23
aggaggtacg tctttactga tgattgatag tgg                                    33

<210> SEQ ID NO 24
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 24
ggaggtacgt ctttactgat gattgatagt ggc                                    33

<210> SEQ ID NO 25
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 25
gaggtacgtc tttactgatg attgatagtg gca                                    33

<210> SEQ ID NO 26
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 26
aggtacgtct ttactgatga ttgatagtgg cac                                    33

<210> SEQ ID NO 27

```
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 27
ggtacgtctt tactgatgat tgatagtggc aca                                  33

<210> SEQ ID NO 28
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 28
gtacgtcttt actgatgatt gatagtggca cag                                  33

<210> SEQ ID NO 29
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 29
tacgtcttta ctgatgattg atagtggcac agg                                  33

<210> SEQ ID NO 30
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 30
aggtacgtct ttactgatga ttgatag                                         27

<210> SEQ ID NO 31
<211> LENGTH: 45
<212> TYPE: DNA
<213> ORGANISM: Artificial Sequence
<220> FEATURE:
<223> OTHER INFORMATION: Primer/Probe/Quencher Sequence

<400> SEQUENCE: 31
cctgtgccac tatcaatcat cagtaaagac gtacctcctg atgaa                     45

<210> SEQ ID NO 32
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 32
cctgtgccac tatcaatcat cagtaaagac gta                                  33

<210> SEQ ID NO 33
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 33
```
ctgtgccact atcaatcatc agtaaagacg tac                                          33

<210> SEQ ID NO 34
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 34
tgtgccacta tcaatcatca gtaaagacgt acc                                          33

<210> SEQ ID NO 35
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 35
gtgccactat caatcatcag taaagacgta cct                                          33

<210> SEQ ID NO 36
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 36
tgccactatc aatcatcagt aaagacgtac ctc                                          33

<210> SEQ ID NO 37
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 37
gccactatca atcatcagta aagacgtacc tcc                                          33

<210> SEQ ID NO 38
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 38
ccactatcaa tcatcagtaa agacgtacct cct                                          33

<210> SEQ ID NO 39
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 39
cactatcaat catcagtaaa gacgtacctc ctg                                          33

<210> SEQ ID NO 40
<211> LENGTH: 33
<212> TYPE: DNA

```
<213> ORGANISM: Artificial Sequence
<220> FEATURE:
<223> OTHER INFORMATION: Primer/Probe/Quencher Sequence

<400> SEQUENCE: 40
actatcaatc atcagtaaag acgtacctcc tga                              33

<210> SEQ ID NO 41
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 41
ctatcaatca tcagtaaaga cgtacctcct gat                              33

<210> SEQ ID NO 42
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 42
tatcaatcat cagtaaagac gtacctcctg atg                              33

<210> SEQ ID NO 43
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 43
atcaatcatc agtaaagacg tacctcctga tga                              33

<210> SEQ ID NO 44
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 44
tcaatcatca gtaaagacgt acctcctgat gaa                              33

<210> SEQ ID NO 45
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 45
ctatcaatca tcagtaaaga cgtacct                                     27

<210> SEQ ID NO 46
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 46
atcaatcatc agtaaagacg tacctcct                                    28
```

-continued

<210> SEQ ID NO 47
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 47
tcatcagtaa agacgtacct cct                                           23

<210> SEQ ID NO 48
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 48
tggatctatc cctctgacat caactgc                                       27

<210> SEQ ID NO 49
<211> LENGTH: 41
<212> TYPE: DNA
<213> ORGANISM: Artificial Sequence
<220> FEATURE:
<223> OTHER INFORMATION: Primer/Probe/Quencher Sequence

<400> SEQUENCE: 49
ccgcaggctt gatagtggca caggggataa ttagcctgcg g                       41

<210> SEQ ID NO 50
<211> LENGTH: 39
<212> TYPE: DNA
<213> ORGANISM: Artificial Sequence
<220> FEATURE:
<223> OTHER INFORMATION: Primer/Probe/Quencher Sequence

<400> SEQUENCE: 50
cgcaggcttg atagtggcac agggataat tagcctgcg                           39

<210> SEQ ID NO 51
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 51
ttgatagtgg cacaggggat aatt                                          24

<210> SEQ ID NO 52
<211> LENGTH: 32
<212> TYPE: DNA
<213> ORGANISM: Artificial Sequence
<220> FEATURE:
<223> OTHER INFORMATION: Primer/Probe/Quencher Sequence

<400> SEQUENCE: 52
ctgatgattg atagtggcac agggataat tt                                  32

<210> SEQ ID NO 53
<211> LENGTH: 24
<212> TYPE: DNA
<213> ORGANISM: Artificial Sequence
<220> FEATURE:

<223> OTHER INFORMATION: Primer/Probe/Quencher Sequence

<400> SEQUENCE: 53
aattatcccc tgtgccacta tcaa                                              24

<210> SEQ ID NO 54
<211> LENGTH: 32
<212> TYPE: DNA
<213> ORGANISM: Artificial Sequence
<220> FEATURE:
<223> OTHER INFORMATION: Primer/Probe/Quencher Sequence

<400> SEQUENCE: 54
aaattatccc ctgtgccact atcaatcatc ag                                     32

<210> SEQ ID NO 55
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 55
agtcaacgaa tggcgattta tctgc                                             25

<210> SEQ ID NO 56
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 56
cgtgttgcag ggatcagtcg tacgg                                             25

<210> SEQ ID NO 57
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 57
ccgtacgact gatccctgca acacg                                             25

<210> SEQ ID NO 58
<211> LENGTH: 39
<212> TYPE: DNA
<213> ORGANISM: Artificial Sequence
<220> FEATURE:
<223> OTHER INFORMATION: Primer/Probe/Quencher Sequence

<400> SEQUENCE: 58
gacttctcga ctgcaaagac gtatgtagat tcgctgaat                              39

<210> SEQ ID NO 59
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 59
gacttctcga ctgcaaagac gtatgta                                           27

```
<210> SEQ ID NO 60
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 60
acttctcgac tgcaaagacg tatgtag                                  27

<210> SEQ ID NO 61
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 61
cttctcgact gcaaagacgt atgtaga                                  27

<210> SEQ ID NO 62
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 62
ttctcgactg caaagacgta tgtagat                                  27

<210> SEQ ID NO 63
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 63
tctcgactgc aaagacgtat gtagatt                                  27

<210> SEQ ID NO 64
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 64
ctcgactgca aagacgtatg tagattc                                  27

<210> SEQ ID NO 65
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 65
tcgactgcaa agacgtatgt agattcg                                  27

<210> SEQ ID NO 66
<211> LENGTH: 27
<212> TYPE: DNA
<213> ORGANISM: Artificial Sequence
<220> FEATURE:
<223> OTHER INFORMATION: Primer/Probe/Quencher Sequence
```

<400> SEQUENCE: 66
cgactgcaaa gacgtatgta gattcgc                               27

<210> SEQ ID NO 67
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 67
gactgcaaag acgtatgtag attcgct                               27

<210> SEQ ID NO 68
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 68
actgcaaaga cgtatgtaga ttcgctg                               27

<210> SEQ ID NO 69
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 69
ctgcaaagac gtatgtagat tcgctga                               27

<210> SEQ ID NO 70
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 70
tgcaaagacg tatgtagatt cgctgaa                               27

<210> SEQ ID NO 71
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 71
gcaaagacgt atgtagattc gctgaat                               27

<210> SEQ ID NO 72
<211> LENGTH: 21
<212> TYPE: DNA
<213> ORGANISM: Artificial Sequence
<220> FEATURE:
<223> OTHER INFORMATION: Primer/Probe/Quencher Sequence

<400> SEQUENCE: 72
actgcaaaga cgtatgtaga t                                     21

<210> SEQ ID NO 73
<211> LENGTH: 25

```
<212> TYPE: DNA
<213> ORGANISM: Artificial Sequence
<220> FEATURE:
<223> OTHER INFORMATION: Primer/Probe/Quencher Sequence

<400> SEQUENCE: 73
cctttccagg tacaacagcg gttac                                       25

<210> SEQ ID NO 74
<211> LENGTH: 36
<212> TYPE: DNA
<213> ORGANISM: Artificial Sequence
<220> FEATURE:
<223> OTHER INFORMATION: Primer/Probe/Quencher Sequence

<400> SEQUENCE: 74
ttcgccccca gttcagagtg aggtccacgt ctcccg                           36

<210> SEQ ID NO 75
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 75
ttcgccccca gttcagagtg aggt                                        24

<210> SEQ ID NO 76
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 76
tcgcccccag ttcagagtga ggtc                                        24

<210> SEQ ID NO 77
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 77
cgcccccagt tcagagtgag gtcc                                        24

<210> SEQ ID NO 78
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 78
gcccccagtt cagagtgagg tcca                                        24

<210> SEQ ID NO 79
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 79
```

```
cccccagttc agagtgaggt ccac                                          24
```

<210> SEQ ID NO 80
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 80

```
ccccagttca gagtgaggtc cacg                                          24
```

<210> SEQ ID NO 81
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 81

```
cccagttcag agtgaggtcc acgt                                          24
```

<210> SEQ ID NO 82
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 82

```
ccagttcaga gtgaggtcca cgtc                                          24
```

<210> SEQ ID NO 83
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 83

```
cagttcagag tgaggtccac gtct                                          24
```

<210> SEQ ID NO 84
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 84

```
agttcagagt gaggtccacg tctc                                          24
```

<210> SEQ ID NO 85
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 85

```
gttcagagtg aggtccacgt ctcc                                          24
```

<210> SEQ ID NO 86
<211> LENGTH: 24
<212> TYPE: DNA
<213> ORGANISM: Artificial Sequence

```
<220> FEATURE:
<223> OTHER INFORMATION: Primer/Probe/Quencher Sequence

<400> SEQUENCE: 86
ttcagagtga ggtccacgtc tccc                                           24

<210> SEQ ID NO 87
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 87
tcagagtgag gtccacgtct cccg                                           24

<210> SEQ ID NO 88
<211> LENGTH: 18
<212> TYPE: DNA
<213> ORGANISM: Artificial Sequence
<220> FEATURE:
<223> OTHER INFORMATION: Primer/Probe/Quencher Sequence

<400> SEQUENCE: 88
agttcagagt gaggtcca                                                  18

<210> SEQ ID NO 89
<211> LENGTH: 38
<212> TYPE: DNA
<213> ORGANISM: Artificial Sequence
<220> FEATURE:
<223> OTHER INFORMATION: Primer/Probe/Quencher Sequence

<400> SEQUENCE: 89
ctgaaactgc tcctgtgtat acgatgacgc cgggagac                            38

<210> SEQ ID NO 90
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 90
ctgaaactgc tcctgtgtat acgatg                                         26

<210> SEQ ID NO 91
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 91
tgaaactgct cctgtgtata cgatga                                         26

<210> SEQ ID NO 92
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 92
gaaactgctc ctgtgtatac gatgac                                         26
```

<210> SEQ ID NO 93
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 93
aaactgctcc tgtgtatacg atgacg                                         26

<210> SEQ ID NO 94
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 94
aactgctcct gtgtatacga tgacgc                                         26

<210> SEQ ID NO 95
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 95
actgctcctg tgtatacgat gacgcc                                         26

<210> SEQ ID NO 96
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 96
ctgctcctgt gtatacgatg acgccg                                         26

<210> SEQ ID NO 97
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 97
tgctcctgtg tatacgatga cgccgg                                         26

<210> SEQ ID NO 98
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 98
gctcctgtgt atacgatgac gccggg                                         26

<210> SEQ ID NO 99
<211> LENGTH: 26
<212> TYPE: DNA
<213> ORGANISM: Artificial Sequence
<220> FEATURE:
<223> OTHER INFORMATION: Primer/Probe/Quencher Sequence -continued

<400> SEQUENCE: 99
ctcctgtgta tacgatgacg ccggga                                    26

<210> SEQ ID NO 100
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 100
tcctgtgtat acgatgacgc cgggag                                    26

<210> SEQ ID NO 101
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 101
cctgtgtata cgatgacgcc gggaga                                    26

<210> SEQ ID NO 102
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 102
ctgtgtatac gatgacgccg ggagac                                    26

<210> SEQ ID NO 103
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 103
ctcctgtgta tacgatgacg                                           20

<210> SEQ ID NO 104
<211> LENGTH: 36
<212> TYPE: DNA
<213> ORGANISM: Artificial Sequence
<220> FEATURE:
<223> OTHER INFORMATION: Primer/Probe/Quencher Sequence

<400> SEQUENCE: 104
tagcggcctg ctcctgtgta tacgatgacg ccgcta                         36

<210> SEQ ID NO 105
<211> LENGTH: 38
<212> TYPE: DNA
<213> ORGANISM: Artificial Sequence
<220> FEATURE:
<223> OTHER INFORMATION: Primer/Probe/Quencher Sequence

<400> SEQUENCE: 105
gtctcccggc gtcatcgtat acacaggagc agtttcag                       38

<210> SEQ ID NO 106

```
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 106
gtctcccggc gtcatcgtat acacag                                          26

<210> SEQ ID NO 107
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 107
tctcccggcg tcatcgtata cacagg                                          26

<210> SEQ ID NO 108
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 108
ctcccggcgt catcgtatac acagga                                          26

<210> SEQ ID NO 109
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 109
tcccggcgtc atcgtataca caggag                                          26

<210> SEQ ID NO 110
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 110
cccggcgtca tcgtatacac aggagc                                          26

<210> SEQ ID NO 111
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 111
ccggcgtcat cgtatacaca ggagca                                          26

<210> SEQ ID NO 112
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 112
```
cggcgtcatc gtatacacag gagcag                    26

<210> SEQ ID NO 113
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 113
ggcgtcatcg tatacacagg agcagt                    26

<210> SEQ ID NO 114
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 114
gcgtcatcgt atacacagga gcagtt                    26

<210> SEQ ID NO 115
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 115
cgtcatcgta tacacaggag cagttt                    26

<210> SEQ ID NO 116
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 116
gtcatcgtat acacaggagc agtttc                    26

<210> SEQ ID NO 117
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 117
tcatcgtata cacaggagca gtttca                    26

<210> SEQ ID NO 118
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 118
catcgtatac acaggagcag tttcag                    26

<210> SEQ ID NO 119
<211> LENGTH: 20
<212> TYPE: DNA

<213> ORGANISM: Artificial Sequence
<220> FEATURE:
<223> OTHER INFORMATION: Primer/Probe/Quencher Sequence

<400> SEQUENCE: 119
cgtcatcgta tacacaggag                                         20

<210> SEQ ID NO 120
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 120
gcttgatgtc tatcaggcgc gtttt                                   25

<210> SEQ ID NO 121
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 121
ttattttgct caataatcag acgaagat                                28

<210> SEQ ID NO 122
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 122
taaattattt tgctcaataa tcagacgaag atg                          33

<210> SEQ ID NO 123
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 123
atcttcgtct gattattgag caaaataa                                28

<210> SEQ ID NO 124
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 124
catcttcgtc tgattattga gcaaaataat tta                          33

<210> SEQ ID NO 125
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 125
tcagtcgtca ctcactggtt tcatcata                                28

<210> SEQ ID NO 126
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 126
tggtcattgt attaccactg aactccatta acg                          33

<210> SEQ ID NO 127
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 127
cgttaatgga gttcagtggt aatacaatga cca                          33

<210> SEQ ID NO 128
<211> LENGTH: 38
<212> TYPE: DNA
<213> ORGANISM: Artificial Sequence
<220> FEATURE:
<223> OTHER INFORMATION: Primer/Probe/Quencher Sequence

<400> SEQUENCE: 128
cagaagcctt acgcttcagg cagatacaga gagaattt                     38

<210> SEQ ID NO 129
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 129
cagaagcctt acgcttcagg cagata                                  26

<210> SEQ ID NO 130
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 130
agaagcctta cgcttcaggc agatac                                  26

<210> SEQ ID NO 131
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 131
gaagccttac gcttcaggca gataca                                  26

<210> SEQ ID NO 132
<211> LENGTH: 26
<212> TYPE: DNA
<213> ORGANISM: Artificial Sequence
<220> FEATURE:

<223> OTHER INFORMATION: Primer/Probe/Quencher Sequence

<400> SEQUENCE: 132
aagccttacg cttcaggcag atacag                                              26

<210> SEQ ID NO 133
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 133
agccttacgc ttcaggcaga tacaga                                              26

<210> SEQ ID NO 134
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 134
gccttacgct tcaggcagat acagag                                              26

<210> SEQ ID NO 135
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 135
ccttacgctt caggcagata cagaga                                              26

<210> SEQ ID NO 136
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 136
cttacgcttc aggcagatac agagag                                              26

<210> SEQ ID NO 137
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 137
ttacgcttca ggcagataca gagaga                                              26

<210> SEQ ID NO 138
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 138
tacgcttcag gcagatacag agagaa                                              26

```
<210> SEQ ID NO 139
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 139
acgcttcagg cagatacaga gagaat                                        26

<210> SEQ ID NO 140
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 140
cgcttcaggc agatacagag agaatt                                        26

<210> SEQ ID NO 141
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 141
gcttcaggca gatacagaga gaattt                                        26

<210> SEQ ID NO 142
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 142
tacgcttcag gcagatacag                                               20

<210> SEQ ID NO 143
<211> LENGTH: 30
<212> TYPE: DNA
<213> ORGANISM: Artificial Sequence
<220> FEATURE:
<223> OTHER INFORMATION: Primer/Probe/Quencher Sequence

<400> SEQUENCE: 143
gggcactgat atatgtgtaa aatctgaaaa                                    30

<210> SEQ ID NO 144
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 144
ttctctctgt atctgcctga agcgtaa                                       27

<210> SEQ ID NO 145
<211> LENGTH: 36
<212> TYPE: DNA
<213> ORGANISM: Artificial Sequence
<220> FEATURE:
<223> OTHER INFORMATION: Primer/Probe/Quencher Sequence
```

<400> SEQUENCE: 145
atttgccgta aagcgggagt caatgtaacg cgcacc                                    36

<210> SEQ ID NO 146
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 146
atttgccgta aagcgggagt caat                                                 24

<210> SEQ ID NO 147
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 147
tttgccgtaa agcgggagtc aatg                                                 24

<210> SEQ ID NO 148
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 148
ttgccgtaaa gcgggagtca atgt                                                 24

<210> SEQ ID NO 149
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 149
tgccgtaaag cgggagtcaa tgta                                                 24

<210> SEQ ID NO 150
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 150
gccgtaaagc gggagtcaat gtaa                                                 24

<210> SEQ ID NO 151
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 151
ccgtaaagcg ggagtcaatg taac                                                 24

<210> SEQ ID NO 152
<211> LENGTH: 24

```
<212> TYPE: DNA
<213> ORGANISM: Artificial Sequence
<220> FEATURE:
<223> OTHER INFORMATION: Primer/Probe/Quencher Sequence

<400> SEQUENCE: 152
cgtaaagcgg gagtcaatgt aacg                                      24

<210> SEQ ID NO 153
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 153
gtaaagcggg agtcaatgta acgc                                      24

<210> SEQ ID NO 154
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 154
taaagcggga gtcaatgtaa cgcg                                      24

<210> SEQ ID NO 155
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 155
aaagcgggag tcaatgtaac gcgc                                      24

<210> SEQ ID NO 156
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 156
aagcgggagt caatgtaacg cgca                                      24

<210> SEQ ID NO 157
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 157
agcgggagtc aatgtaacgc gcac                                      24

<210> SEQ ID NO 158
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 158
```

```
gcgggagtca atgtaacgcg cacc                                          24
```

```
<210> SEQ ID NO 159
<211> LENGTH: 18
<212> TYPE: DNA
<213> ORGANISM: Artificial Sequence
<220> FEATURE:
<223> OTHER INFORMATION: Primer/Probe/Quencher Sequence

<400> SEQUENCE: 159
aaagcgggag tcaatgta                                                 18
```

```
<210> SEQ ID NO 160
<211> LENGTH: 32
<212> TYPE: DNA
<213> ORGANISM: Artificial Sequence
<220> FEATURE:
<223> OTHER INFORMATION: Primer/Probe/Quencher Sequence

<400> SEQUENCE: 160
gaaaacatgc tggcatttgg tcaggtcggt gc                                 32
```

```
<210> SEQ ID NO 161
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 161
gaaaacatgc tggcatttgg                                               20
```

```
<210> SEQ ID NO 162
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 162
aaaacatgct ggcatttggt                                               20
```

```
<210> SEQ ID NO 163
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 163
aaacatgctg gcatttggtc                                               20
```

```
<210> SEQ ID NO 164
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 164
aacatgctgg catttggtca                                               20
```

```
<210> SEQ ID NO 165
<211> LENGTH: 20
<212> TYPE: DNA
<213> ORGANISM: Artificial Sequence
```

```
<220> FEATURE:
<223> OTHER INFORMATION: Primer/Probe/Quencher Sequence

<400> SEQUENCE: 165
acatgctggc atttggtcag                                               20

<210> SEQ ID NO 166
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 166
catgctggca tttggtcagg                                               20

<210> SEQ ID NO 167
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 167
atgctggcat ttggtcaggt                                               20

<210> SEQ ID NO 168
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 168
tgctggcatt tggtcaggtc                                               20

<210> SEQ ID NO 169
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 169
gctggcattt ggtcaggtcg                                               20

<210> SEQ ID NO 170
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 170
ctggcatttg gtcaggtcgg                                               20

<210> SEQ ID NO 171
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 171
tggcatttgg tcaggtcggt                                               20
```

<210> SEQ ID NO 172
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 172
ggcatttggt caggtcggtg                                                    20

<210> SEQ ID NO 173
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 173
gcatttggtc aggtcggtgc                                                    20

<210> SEQ ID NO 174
<211> LENGTH: 14
<212> TYPE: DNA
<213> ORGANISM: Artificial Sequence
<220> FEATURE:
<223> OTHER INFORMATION: Primer/Probe/Quencher Sequence

<400> SEQUENCE: 174
ctggcatttg gtca                                                          14

<210> SEQ ID NO 175
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 175
cagcgaccat gctggcattt ggtcaggtcg ctg                                     33

<210> SEQ ID NO 176
<211> LENGTH: 32
<212> TYPE: DNA
<213> ORGANISM: Artificial Sequence
<220> FEATURE:
<223> OTHER INFORMATION: Primer/Probe/Quencher Sequence

<400> SEQUENCE: 176
gcaccgacct gaccaaatgc cagcatgttt tc                                      32

<210> SEQ ID NO 177
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 177
gcaccgacct gaccaaatgc                                                    20

<210> SEQ ID NO 178
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 178
caccgacctg accaaatgcc                                          20

<210> SEQ ID NO 179
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 179
accgacctga ccaaatgcca                                          20

<210> SEQ ID NO 180
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 180
ccgacctgac caaatgccag                                          20

<210> SEQ ID NO 181
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 181
cgacctgacc aaatgccagc                                          20

<210> SEQ ID NO 182
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 182
gacctgacca aatgccagca                                          20

<210> SEQ ID NO 183
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 183
acctgaccaa atgccagcat                                          20

<210> SEQ ID NO 184
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 184
cctgaccaaa tgccagcatg                                          20

<210> SEQ ID NO 185

```
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 185
ctgaccaaat gccagcatgt                                             20

<210> SEQ ID NO 186
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 186
tgaccaaatg ccagcatgtt                                             20

<210> SEQ ID NO 187
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 187
gaccaaatgc cagcatgttt                                             20

<210> SEQ ID NO 188
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 188
accaaatgcc agcatgtttt                                             20

<210> SEQ ID NO 189
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 189
ccaaatgcca gcatgttttc                                             20

<210> SEQ ID NO 190
<211> LENGTH: 14
<212> TYPE: DNA
<213> ORGANISM: Artificial Sequence
<220> FEATURE:
<223> OTHER INFORMATION: Primer/Probe/Quencher Sequence

<400> SEQUENCE: 190
tgaccaaatg ccag                                                   14

<210> SEQ ID NO 191
<211> LENGTH: 41
<212> TYPE: DNA
<213> ORGANISM: Artificial Sequence
<220> FEATURE:
<223> OTHER INFORMATION: Primer/Probe/Quencher Sequence

<400> SEQUENCE: 191
```

```
gcagagtggt aataactttg acggtagttc actggacttc t              41
```

<210> SEQ ID NO 192
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 192

```
gcagagtggt aataactttg acggtagtt                            29
```

<210> SEQ ID NO 193
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 193

```
cagagtggta ataactttga cggtagttc                            29
```

<210> SEQ ID NO 194
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 194

```
agagtggtaa taactttgac ggtagttca                            29
```

<210> SEQ ID NO 195
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 195

```
gagtggtaat aactttgacg gtagttcac                            29
```

<210> SEQ ID NO 196
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 196

```
agtggtaata actttgacgg tagttcact                            29
```

<210> SEQ ID NO 197
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 197

```
gtggtaataa ctttgacggt agttcactg                            29
```

<210> SEQ ID NO 198
<211> LENGTH: 29
<212> TYPE: DNA

```
<213> ORGANISM: Artificial Sequence
<220> FEATURE:
<223> OTHER INFORMATION: Primer/Probe/Quencher Sequence

<400> SEQUENCE: 198
tggtaataac tttgacggta gttcactgg                                    29

<210> SEQ ID NO 199
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 199
ggtaataact tgacggtag ttcactgga                                     29

<210> SEQ ID NO 200
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 200
gtaataactt tgacggtagt tcactggac                                    29

<210> SEQ ID NO 201
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 201 taataactttt gacggtagtt cactggact                                   29

<210> SEQ ID NO 202
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 202
aataactttg acggtagttc actggactt                                    29

<210> SEQ ID NO 203
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 203
ataactttga cggtagttca ctggacttc                                    29

<210> SEQ ID NO 204
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 204
taactttgac ggtagttcac tggacttct                                    29
```

<210> SEQ ID NO 205
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 205
taataacttt gacggtagtt cac                                          23

<210> SEQ ID NO 206
<211> LENGTH: 41
<212> TYPE: DNA
<213> ORGANISM: Artificial Sequence
<220> FEATURE:
<223> OTHER INFORMATION: Primer/Probe/Quencher Sequence

<400> SEQUENCE: 206
cagctaaagt tcatggtttt cattgtcctg agtttagggg g                      41

<210> SEQ ID NO 207
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 207
cagctaaagt tcatggtttt cattgtcct                                    29

<210> SEQ ID NO 208
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 208
agctaaagtt catggttttc attgtcctg                                    29

<210> SEQ ID NO 209
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 209
gctaaagttc atggttttca ttgtcctga                                    29

<210> SEQ ID NO 210
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 210
ctaaagttca tggttttcat tgtcctgag                                    29

<210> SEQ ID NO 211
<211> LENGTH: 29
<212> TYPE: DNA
<213> ORGANISM: Artificial Sequence
<220> FEATURE:

<223> OTHER INFORMATION: Primer/Probe/Quencher Sequence

<400> SEQUENCE: 211
taaagttcat ggttttcatt gtcctgagt                                29

<210> SEQ ID NO 212
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 212
aaagttcatg gttttcattg tcctgagtt                                29

<210> SEQ ID NO 213
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 213
aagttcatgg ttttcattgt cctgagttt                                29

<210> SEQ ID NO 214
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 214
agttcatggt tttcattgtc ctgagttta                                29

<210> SEQ ID NO 215
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 215
gttcatggtt ttcattgtcc tgagtttag                                29

<210> SEQ ID NO 216
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 216
ttcatggttt tcattgtcct gagtttagg                                29

<210> SEQ ID NO 217
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 217
tcatggtttt cattgtcctg agtttaggg                                29

```
<210> SEQ ID NO 218
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 218
catggttttc attgtcctga gtttagggg                                29

<210> SEQ ID NO 219
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 219
atggttttca ttgtcctgag tttaggggg                                29

<210> SEQ ID NO 220
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 220
ttcatggttt tcattgtcct gag                                      23

<210> SEQ ID NO 221
<211> LENGTH: 43
<212> TYPE: DNA
<213> ORGANISM: Artificial Sequence
<220> FEATURE:
<223> OTHER INFORMATION: Primer/Probe/Quencher Sequence

<400> SEQUENCE: 221
gcgatacttt gaaccttata tcccaatata gtacccaccc ccc                43

<210> SEQ ID NO 222
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 222
gcgatacttt gaaccttata tcccaatata g                             31

<210> SEQ ID NO 223
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 223
cgatactttg aaccttatat cccaatatag t                             31

<210> SEQ ID NO 224
<211> LENGTH: 31
<212> TYPE: DNA
<213> ORGANISM: Artificial Sequence
<220> FEATURE:
<223> OTHER INFORMATION: Primer/Probe/Quencher Sequence
```

<400> SEQUENCE: 224
gatactttga accttatatc ccaatatagt a                               31

<210> SEQ ID NO 225
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 225
atactttgaa ccttatatcc caatatagta c                               31

<210> SEQ ID NO 226
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 226
tactttgaac cttatatccc aatatagtac c                               31

<210> SEQ ID NO 227
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 227
actttgaacc ttatatccca atatagtacc c                               31

<210> SEQ ID NO 228
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 228
ctttgaacct tatatcccaa tatagtaccc a                               31

<210> SEQ ID NO 229
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 229
tttgaacctt atatcccaat atagtaccca c                               31

<210> SEQ ID NO 230
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 230 ttgaaccttwa tatcccaata tagtacccac c                              31

<210> SEQ ID NO 231
<211> LENGTH: 31

```
<212> TYPE: DNA
<213> ORGANISM: Artificial Sequence
<220> FEATURE:
<223> OTHER INFORMATION: Primer/Probe/Quencher Sequence

<400> SEQUENCE: 231
tgaaccttat atcccaatat agtacccacc c                              31

<210> SEQ ID NO 232
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 232
gaaccttata tcccaatata gtacccaccc c                              31

<210> SEQ ID NO 233
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 233
aaccttatat cccaatatag tacccacccc c                              31

<210> SEQ ID NO 234
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 234
accttatatc ccaatatagt acccacccccc c                             31

<210> SEQ ID NO 235
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 235
tgaaccttat atcccaatat agtac                                     25

<210> SEQ ID NO 236
<211> LENGTH: 43
<212> TYPE: DNA
<213> ORGANISM: Artificial Sequence
<220> FEATURE:
<223> OTHER INFORMATION: Primer/Probe/Quencher Sequence

<400> SEQUENCE: 236 gggggggtggg tactatattg ggatataagg ttcaaagtat cgc                43

<210> SEQ ID NO 237
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 237
```

```
gggggtggg tactatattg ggatataagg t                                31
```

<210> SEQ ID NO 238
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 238

```
gggggtgggt actatattgg gatataaggt t                               31
```

<210> SEQ ID NO 239
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 239

```
ggggtgggta ctatattggg atataaggtt c                               31
```

<210> SEQ ID NO 240
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 240

```
gggtgggtac tatattggga tataaggttc a                               31
```

<210> SEQ ID NO 241
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 241

```
ggtgggtact atattgggat ataaggttca a                               31
```

<210> SEQ ID NO 242
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 242

```
gtgggtacta tattgggata taaggttcaa a                               31
```

<210> SEQ ID NO 243
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 243

```
tgggtactat attgggatat aaggttcaaa g                               31
```

<210> SEQ ID NO 244
<211> LENGTH: 31
<212> TYPE: DNA
<213> ORGANISM: Artificial Sequence

```
<220> FEATURE:
<223> OTHER INFORMATION: Primer/Probe/Quencher Sequence

<400> SEQUENCE: 244
gggtactata ttgggatata aggttcaaag t                              31

<210> SEQ ID NO 245
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 245
ggtactatat tgggatataa ggttcaaagt a                              31

<210> SEQ ID NO 246
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 246
gtactatatt gggatataag gttcaaagta t                              31

<210> SEQ ID NO 247
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 247
tactatattg ggatataagg ttcaaagtat c                              31

<210> SEQ ID NO 248
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 248
actatattgg gatataaggt tcaaagtatc g                              31

<210> SEQ ID NO 249
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 249
ctatattggg atataaggtt caaagtatcg c                              31

<210> SEQ ID NO 250
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 250
gtactatatt gggatataag gttca                                    25
```

```
<210> SEQ ID NO 251
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 251
tgaaattaga agcgcgttca tcc                                          23

<210> SEQ ID NO 252
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 252
cataaatatt gcaaaagaca ttattga                                      27

<210> SEQ ID NO 253
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 253
tccccataaa tattgcaaaa gacattattg a                                 31

<210> SEQ ID NO 254
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 254
tcaataatgt cttttgcaat atttatg                                      27

<210> SEQ ID NO 255
<211> LENGTH: 30
<212> TYPE: DNA
<213> ORGANISM: Artificial Sequence
<220> FEATURE:
<223> OTHER INFORMATION: Primer/Probe/Quencher Sequence

<400> SEQUENCE: 255
aatattatta ttcttggcac tcttgcttcg                                   30

<210> SEQ ID NO 256
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 256
ccgtcgcgta cagagacgtt gcaa                                         24

<210> SEQ ID NO 257
<211> LENGTH: 24
<212> TYPE: DNA
<213> ORGANISM: Artificial Sequence
<220> FEATURE:
<223> OTHER INFORMATION: Primer/Probe/Quencher Sequence
```

<400> SEQUENCE: 257
ttgcaacgtc tctgtacgcg acgg                                    24

<210> SEQ ID NO 258
<211> LENGTH: 40
<212> TYPE: DNA
<213> ORGANISM: Artificial Sequence
<220> FEATURE:
<223> OTHER INFORMATION: Primer/Probe/Quencher Sequence

<400> SEQUENCE: 258
tcttttttat accctcttat ggacaatcca accgaaccaa                   40

<210> SEQ ID NO 259
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 259
tcttttttat accctcttat ggacaatc                                28

<210> SEQ ID NO 260
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 260
cttttttata ccctcttatg gacaatcc                                28

<210> SEQ ID NO 261
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 261
ttttttatac cctcttatgg acaatcca                                28

<210> SEQ ID NO 262
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 262
tttttatacc ctcttatgga caatccaa                                28

<210> SEQ ID NO 263
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 263
ttttataccc tcttatggac aatccaac                                28

<210> SEQ ID NO 264

```
<210> SEQ ID NO 264
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 264 tttatacct cttatggaca atccaacc                                           28

<210> SEQ ID NO 265
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 265
ttataccctc ttatggacaa tccaaccg                                          28

<210> SEQ ID NO 266
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 266
tataccctct tatggacaat ccaaccga                                          28

<210> SEQ ID NO 267
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 267
ataccctctt atggacaatc caaccgaa                                          28

<210> SEQ ID NO 268
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 268
taccctctta tggacaatcc aaccgaac                                          28

<210> SEQ ID NO 269
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 269
accctcttat ggacaatcca accgaacc                                          28

<210> SEQ ID NO 270
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 270
```

```
ccctcttatg gacaatccaa ccgaacca                                       28
```

<210> SEQ ID NO 271
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 271

```
cctcttatgg acaatccaac cgaaccaa                                       28
```

<210> SEQ ID NO 272
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 272

```
taccctctta tggacaatcc aa                                             22
```

<210> SEQ ID NO 273
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 273

```
aatagttgaa acacccgtaa tggc                                           24
```

<210> SEQ ID NO 274
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 274

```
ttgatttaac ggggttgcta tgactga                                        27
```

<210> SEQ ID NO 275
<211> LENGTH: 41
<212> TYPE: DNA
<213> ORGANISM: Artificial Sequence
<220> FEATURE:
<223> OTHER INFORMATION: Primer/Probe/Quencher Sequence

<400> SEQUENCE: 275

```
gagattcaat tcacttttaa gaactttcag tgtgtaacaa a                        41
```

<210> SEQ ID NO 276
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 276

```
gagattcaat tcacttttaa gaactttca                                      29
```

<210> SEQ ID NO 277
<211> LENGTH: 29
<212> TYPE: DNA

```
<213> ORGANISM: Artificial Sequence
<220> FEATURE:
<223> OTHER INFORMATION: Primer/Probe/Quencher Sequence

<400> SEQUENCE: 277
agattcaatt cacttttaag aactttcag                                   29

<210> SEQ ID NO 278
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 278
gattcaattc acttttaaga actttcagt                                   29

<210> SEQ ID NO 279
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 279
attcaattca cttttaagaa ctttcagtg                                   29

<210> SEQ ID NO 280
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 280
ttcaattcac ttttaagaac tttcagtgt                                   29

<210> SEQ ID NO 281
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 281
tcaattcact tttaagaact ttcagtgtg                                   29

<210> SEQ ID NO 282
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 282
caattcactt ttaagaactt tcagtgtgt                                   29

<210> SEQ ID NO 283
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 283
aattcacttt taagaacttt cagtgtgta                                   29
```

<210> SEQ ID NO 284
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 284
attcactttt aagaactttc agtgtgtaa                              29

<210> SEQ ID NO 285
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 285
ttcactttta agaactttca gtgtgtaac                              29

<210> SEQ ID NO 286
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 286
tcacttttaa gaactttcag tgtgtaaca                              29

<210> SEQ ID NO 287
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 287
cacttttaag aactttcagt gtgtaacaa                              29

<210> SEQ ID NO 288
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 288
acttttaaga actttcagtg tgtaacaaa                              29

<210> SEQ ID NO 289
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 289
ttcacttttt agaactttca gtg                                    23

<210> SEQ ID NO 290
<211> LENGTH: 35
<212> TYPE: DNA
<213> ORGANISM: Artificial Sequence
<220> FEATURE:

```
<223> OTHER INFORMATION: Primer/Probe/Quencher Sequence

<400> SEQUENCE: 290
ttttctgaag gcgaggcaac acattatata gtgct                                35

<210> SEQ ID NO 291
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 291
ttttctgaag gcgaggcaac aca                                             23

<210> SEQ ID NO 292
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 292
tttctgaagg cgaggcaaca cat                                             23

<210> SEQ ID NO 293
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 293
ttctgaaggc gaggcaacac att                                             23

<210> SEQ ID NO 294
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 294
tctgaaggcg aggcaacaca tta                                             23

<210> SEQ ID NO 295
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 295
ctgaaggcga ggcaacacat tat                                             23

<210> SEQ ID NO 296
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 296
tgaaggcgag gcaacacatt ata                                             23
```

```
<210> SEQ ID NO 297
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 297
gaaggcgagg caacacatta tat                                              23

<210> SEQ ID NO 298
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 298
aaggcgaggc aacacattat ata                                              23

<210> SEQ ID NO 299
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 299
aggcgaggca acacattata tag                                              23

<210> SEQ ID NO 300
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 300
ggcgaggcaa cacattatat agt                                              23

<210> SEQ ID NO 301
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 301
gcgaggcaac acattatata gtg                                              23

<210> SEQ ID NO 302
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 302
cgaggcaaca cattatatag tgc                                              23

<210> SEQ ID NO 303
<211> LENGTH: 23
<212> TYPE: DNA
<213> ORGANISM: Artificial Sequence
<220> FEATURE:
<223> OTHER INFORMATION: Primer/Probe/Quencher Sequence
```

<400> SEQUENCE: 303
gaggcaacac attatatagt gct        23

<210> SEQ ID NO 304
<211> LENGTH: 17
<212> TYPE: DNA
<213> ORGANISM: Artificial Sequence
<220> FEATURE:
<223> OTHER INFORMATION: Primer/Probe/Quencher Sequence

<400> SEQUENCE: 304
ggcgaggcaa cacatta        17

<210> SEQ ID NO 305
<211> LENGTH: 37
<212> TYPE: DNA
<213> ORGANISM: Artificial Sequence
<220> FEATURE:
<223> OTHER INFORMATION: Primer/Probe/Quencher Sequence

<400> SEQUENCE: 305
cggcactgaa ggcgaggcaa cacattatat agtgccg        37

<210> SEQ ID NO 306
<211> LENGTH: 41
<212> TYPE: DNA
<213> ORGANISM: Artificial Sequence
<220> FEATURE:
<223> OTHER INFORMATION: Primer/Probe/Quencher Sequence

<400> SEQUENCE: 306
cgcggcactg aaggcgaggc aacacattat atagtgccgc g        41

<210> SEQ ID NO 307
<211> LENGTH: 35
<212> TYPE: DNA
<213> ORGANISM: Artificial Sequence
<220> FEATURE:
<223> OTHER INFORMATION: Primer/Probe/Quencher Sequence

<400> SEQUENCE: 307
agcactatat aatgtgttgc ctcgccttca gaaaa        35

<210> SEQ ID NO 308
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 308
agcactatat aatgtgttgc ctc        23

<210> SEQ ID NO 309
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 309
gcactatata atgtgttgcc tcg        23

<210> SEQ ID NO 310
<211> LENGTH: 23

```
<212> TYPE: DNA
<213> ORGANISM: Artificial Sequence
<220> FEATURE:
<223> OTHER INFORMATION: Primer/Probe/Quencher Sequence

<400> SEQUENCE: 310
cactatataa tgtgttgcct cgc                                              23

<210> SEQ ID NO 311
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 311
actatataat gtgttgcctc gcc                                              23

<210> SEQ ID NO 312
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 312
ctatataatg tgttgcctcg cct                                              23

<210> SEQ ID NO 313
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 313
tatataatgt gttgcctcgc ctt                                              23

<210> SEQ ID NO 314
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 314
atataatgtg ttgcctcgcc ttc                                              23

<210> SEQ ID NO 315
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 315
tataatgtgt tgcctcgcct tca                                              23

<210> SEQ ID NO 316
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 316
```
ataatgtgtt gcctcgcctt cag                                        23

<210> SEQ ID NO 317
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 317
taatgtgttg cctcgccttc aga                                        23

<210> SEQ ID NO 318
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 318
aatgtgttgc ctcgccttca gaa                                        23

<210> SEQ ID NO 319
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 319
atgtgttgcc tcgccttcag aaa                                        23

<210> SEQ ID NO 320
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 320
tgtgttgcct cgccttcaga aaa                                        23

<210> SEQ ID NO 321
<211> LENGTH: 17
<212> TYPE: DNA
<213> ORGANISM: Artificial Sequence
<220> FEATURE:
<223> OTHER INFORMATION: Primer/Probe/Quencher Sequence

<400> SEQUENCE: 321
taatgtgttg cctcgcc                                               17

<210> SEQ ID NO 322
<211> LENGTH: 37
<212> TYPE: DNA
<213> ORGANISM: Artificial Sequence
<220> FEATURE:
<223> OTHER INFORMATION: Primer/Probe/Quencher Sequence

<400> SEQUENCE: 322
cggcactata taatgtgttg cctcgccttc agtgccg                         37

<210> SEQ ID NO 323
<211> LENGTH: 41
<212> TYPE: DNA
<213> ORGANISM: Artificial Sequence

```
<220> FEATURE:
<223> OTHER INFORMATION: Primer/Probe/Quencher Sequence

<400> SEQUENCE: 323
cgcggcacta taaatgtgt tgcctcgcct tcagtgccgc g                    41

<210> SEQ ID NO 324
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 324
cacgatgttg atcatctggg aga                                       23

<210> SEQ ID NO 325
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 325
acacactgaa agttcttaaa agtgaat                                   27

<210> SEQ ID NO 326
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 326
attcactttt aagaactttc agtgtgt                                   27

<210> SEQ ID NO 327
<211> LENGTH: 34
<212> TYPE: DNA
<213> ORGANISM: Artificial Sequence
<220> FEATURE:
<223> OTHER INFORMATION: Primer/Probe/Quencher Sequence

<400> SEQUENCE: 327 attttttgt tccaggtggt aggattcgca aaaa                            34

<210> SEQ ID NO 328
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 328 attttttgt tccaggtggt ag                                         22

<210> SEQ ID NO 329
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 329
tttttttgtt ccaggtggta gg                                        22
```

<210> SEQ ID NO 330
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 330 tttttgttc caggtggtag ga                                          22

<210> SEQ ID NO 331
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 331
tttttgttcc aggtggtagg at                                         22

<210> SEQ ID NO 332
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 332
ttttgttcca ggtggtagga tt                                         22

<210> SEQ ID NO 333
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 333
tttgttccag gtggtaggat tc                                         22

<210> SEQ ID NO 334
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 334
ttgttccagg tggtaggatt cg                                         22

<210> SEQ ID NO 335
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 335
tgttccaggt ggtaggattc gc                                         22

<210> SEQ ID NO 336
<211> LENGTH: 22
<212> TYPE: DNA
<213> ORGANISM: Artificial Sequence
<220> FEATURE:
<223> OTHER INFORMATION: Primer/Probe/Quencher Sequence

```
<400> SEQUENCE: 336
gttccaggtg gtaggattcg ca                                              22

<210> SEQ ID NO 337
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 337
ttccaggtgg taggattcgc aa                                              22

<210> SEQ ID NO 338
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 338
tccaggtggt aggattcgca aa                                              22

<210> SEQ ID NO 339
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 339
ccaggtggta ggattcgcaa aa                                              22

<210> SEQ ID NO 340
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 340
caggtggtag gattcgcaaa aa                                              22

<210> SEQ ID NO 341
<211> LENGTH: 16
<212> TYPE: DNA
<213> ORGANISM: Artificial Sequence
<220> FEATURE:
<223> OTHER INFORMATION: Primer/Probe/Quencher Sequence

<400> SEQUENCE: 341
ttccaggtgg taggat                                                     16

<210> SEQ ID NO 342
<211> LENGTH: 34
<212> TYPE: DNA
<213> ORGANISM: Artificial Sequence
<220> FEATURE:
<223> OTHER INFORMATION: Primer/Probe/Quencher Sequence

<400> SEQUENCE: 342
accaatgaac cgaaatgatg ggtgctaaga aaaa                                 34

<210> SEQ ID NO 343
```

```
<210> SEQ ID NO 343
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 343
accaatgaac cgaaatgatg gg                                              22

<210> SEQ ID NO 344
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 344
ccaatgaacc gaaatgatgg gt                                              22

<210> SEQ ID NO 345
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 345
caatgaaccg aaatgatggg tg                                              22

<210> SEQ ID NO 346
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 346
aatgaaccga aatgatgggt gc                                              22

<210> SEQ ID NO 347
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 347
atgaaccgaa atgatgggtg ct                                              22

<210> SEQ ID NO 348
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 348
tgaaccgaaa tgatgggtgc ta                                              22

<210> SEQ ID NO 349
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 349
```
gaaccgaaat gatgggtgct aa                                              22

<210> SEQ ID NO 350
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 350
aaccgaaatg atgggtgcta ag                                              22

<210> SEQ ID NO 351
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 351
accgaaatga tgggtgctaa ga                                              22

<210> SEQ ID NO 352
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 352
ccgaaatgat gggtgctaag aa                                              22

<210> SEQ ID NO 353
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 353
cgaaatgatg ggtgctaaga aa                                              22

<210> SEQ ID NO 354
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 354
gaaatgatgg gtgctaagaa aa                                              22

<210> SEQ ID NO 355
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 355
aaatgatggg tgctaagaaa aa                                              22

<210> SEQ ID NO 356
<211> LENGTH: 16
<212> TYPE: DNA

<213> ORGANISM: Artificial Sequence
<220> FEATURE:
<223> OTHER INFORMATION: Primer/Probe/Quencher Sequence

<400> SEQUENCE: 356
ccgaaatgat gggtgc                                                            16

<210> SEQ ID NO 357
<211> LENGTH: 37
<212> TYPE: DNA
<213> ORGANISM: Artificial Sequence
<220> FEATURE:
<223> OTHER INFORMATION: Primer/Probe/Quencher Sequence

<400> SEQUENCE: 357
cttcactatc gctactattg gtggagtatt tctattt                                     37

<210> SEQ ID NO 358
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 358
cttcactatc gctactattg gtgga                                                  25

<210> SEQ ID NO 359
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 359
ttcactatcg ctactattgg tggag                                                  25

<210> SEQ ID NO 360
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 360
tcactatcgc tactattggt ggagt                                                  25

<210> SEQ ID NO 361
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 361
cactatcgct actattggtg gagta                                                  25

<210> SEQ ID NO 362
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 362
actatcgcta ctattggtgg agtat                                                  25

<210> SEQ ID NO 363
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 363
ctatcgctac tattggtgga gtatt                                   25

<210> SEQ ID NO 364
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 364
tatcgctact attggtggag tattt                                   25

<210> SEQ ID NO 365
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 365
atcgctacta ttggtggagt atttc                                   25

<210> SEQ ID NO 366
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 366
tcgctactat tggtggagta tttct                                   25

<210> SEQ ID NO 367
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 367
cgctactatt ggtggagtat ttcta                                   25

<210> SEQ ID NO 368
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 368
gctactattg gtggagtatt tctat                                   25

<210> SEQ ID NO 369
<211> LENGTH: 25
<212> TYPE: DNA
<213> ORGANISM: Artificial Sequence
<220> FEATURE:

```
<223> OTHER INFORMATION: Primer/Probe/Quencher Sequence

<400> SEQUENCE: 369
ctactattgg tggagtattt ctatt                                          25

<210> SEQ ID NO 370
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 370
tactattggt ggagtatttc tattt                                          25

<210> SEQ ID NO 371
<211> LENGTH: 19
<212> TYPE: DNA
<213> ORGANISM: Artificial Sequence
<220> FEATURE:
<223> OTHER INFORMATION: Primer/Probe/Quencher Sequence

<400> SEQUENCE: 371
cgctactatt ggtggagta                                                 19

<210> SEQ ID NO 372
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 372
cactatcgct actattggtg gagtattt                                       28

<210> SEQ ID NO 373
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 373
tcgctactat tggtggagta tttc                                           24

<210> SEQ ID NO 374
<211> LENGTH: 43
<212> TYPE: DNA
<213> ORGANISM: Artificial Sequence
<220> FEATURE:
<223> OTHER INFORMATION: Primer/Probe/Quencher Sequence

<400> SEQUENCE: 374
cctgcccact atcgctacta ttggtggagt atttgtgggc agg                      43

<210> SEQ ID NO 375
<211> LENGTH: 37
<212> TYPE: DNA
<213> ORGANISM: Artificial Sequence
<220> FEATURE:
<223> OTHER INFORMATION: Primer/Probe/Quencher Sequence

<400> SEQUENCE: 375
aaatagaaat actccaccaa tagtagcgat agtgaag                             37
```

```
<210> SEQ ID NO 376
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 376
aaatagaaat actccaccaa tagta                                              25

<210> SEQ ID NO 377
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 377
aatagaaata ctccaccaat agtag                                              25

<210> SEQ ID NO 378
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 378
atagaaatac tccaccaata gtagc                                              25

<210> SEQ ID NO 379
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 379
tagaaatact ccaccaatag tagcg                                              25

<210> SEQ ID NO 380
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 380
agaaatactc caccaatagt agcga                                              25

<210> SEQ ID NO 381
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 381
gaaatactcc accaatagta gcgat                                              25

<210> SEQ ID NO 382
<211> LENGTH: 25
<212> TYPE: DNA
<213> ORGANISM: Artificial Sequence
<220> FEATURE:
<223> OTHER INFORMATION: Primer/Probe/Quencher Sequence
```

<400> SEQUENCE: 382
aaatactcca ccaatagtag cgata                                  25

<210> SEQ ID NO 383
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 383
aatactccac caatagtagc gatag                                  25

<210> SEQ ID NO 384
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 384
atactccacc aatagtagcg atagt                                  25

<210> SEQ ID NO 385
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 385
tactccacca atagtagcga tagtg                                  25

<210> SEQ ID NO 386
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 386
actccaccaa tagtagcgat agtga                                  25

<210> SEQ ID NO 387
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 387
ctccaccaat agtagcgata gtgaa                                  25

<210> SEQ ID NO 388
<211> LENGTH: 25
<212> TYPE: DNA
<213> ORGANISM: Artificial Sequence
<220> FEATURE:
<223> OTHER INFORMATION: Primer/Probe/Quencher Sequence

<400> SEQUENCE: 388
tccaccaata gtagcgatag tgaag                                  25

<210> SEQ ID NO 389
<211> LENGTH: 19

```
<212> TYPE: DNA
<213> ORGANISM: Artificial Sequence
<220> FEATURE:
<223> OTHER INFORMATION: Primer/Probe/Quencher Sequence

<400> SEQUENCE: 389
tactccacca atagtagcg                                                  19

<210> SEQ ID NO 390
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 390
aaatactcca ccaatagtag cgatagtg                                        28

<210> SEQ ID NO 391
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 391
gaaatactcc accaatagta gcga                                            24

<210> SEQ ID NO 392
<211> LENGTH: 43
<212> TYPE: DNA
<213> ORGANISM: Artificial Sequence
<220> FEATURE:
<223> OTHER INFORMATION: Primer/Probe/Quencher Sequence

<400> SEQUENCE: 392
cctgcccaca aatactccac caatagtagc gatagtgggc agg                       43

<210> SEQ ID NO 393
<211> LENGTH: 39
<212> TYPE: DNA
<213> ORGANISM: Artificial Sequence
<220> FEATURE:
<223> OTHER INFORMATION: Primer/Probe/Quencher Sequence

<400> SEQUENCE: 393
ggtctcttag acttagggct aactccaaca attggtcgt                            39

<210> SEQ ID NO 394
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 394
ggtctcttag acttagggct aactcca                                         27

<210> SEQ ID NO 395
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 395
```
gtctcttaga cttagggcta actccaa                                         27

<210> SEQ ID NO 396
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 396
tctcttagac ttagggctaa ctccaac                                         27

<210> SEQ ID NO 397
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 397
ctcttagact tagggctaac tccaaca                                         27

<210> SEQ ID NO 398
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 398
tcttagactt agggctaact ccaacaa                                         27

<210> SEQ ID NO 399
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 399
cttagactta gggctaactc caacaat                                         27

<210> SEQ ID NO 400
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 400
ttagacttag ggctaactcc aacaatt                                         27

<210> SEQ ID NO 401
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 401
tagacttagg gctaactcca acaattg                                         27

<210> SEQ ID NO 402
<211> LENGTH: 27
<212> TYPE: DNA
<213> ORGANISM: Artificial Sequence

```
<220> FEATURE:
<223> OTHER INFORMATION: Primer/Probe/Quencher Sequence

<400> SEQUENCE: 402
agacttaggg ctaactccaa caattgg                                    27

<210> SEQ ID NO 403
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 403
gacttagggc taactccaac aattggt                                    27

<210> SEQ ID NO 404
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 404
acttagggct aactccaaca attggtc                                    27

<210> SEQ ID NO 405
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 405
cttagggcta actccaacaa ttggtcg                                    27

<210> SEQ ID NO 406
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 406
ttagggctaa ctccaacaat tggtcgt                                    27

<210> SEQ ID NO 407
<211> LENGTH: 21
<212> TYPE: DNA
<213> ORGANISM: Artificial Sequence
<220> FEATURE:
<223> OTHER INFORMATION: Primer/Probe/Quencher Sequence

<400> SEQUENCE: 407
gacttagggc taactccaac a                                          21

<210> SEQ ID NO 408
<211> LENGTH: 39
<212> TYPE: DNA
<213> ORGANISM: Artificial Sequence
<220> FEATURE:
<223> OTHER INFORMATION: Primer/Probe/Quencher Sequence

<400> SEQUENCE: 408
aactatgcag cagcacttca attggtcgat aactggtat                       39
```

<210> SEQ ID NO 409
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 409
aactatgcag cagcacttca attggtc                                    27

<210> SEQ ID NO 410
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 410
actatgcagc agcacttcaa ttggtcg                                    27

<210> SEQ ID NO 411
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 411
ctatgcagca gcacttcaat tggtcga                                    27

<210> SEQ ID NO 412
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 412
tatgcagcag cacttcaatt ggtcgat                                    27

<210> SEQ ID NO 413
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 413
atgcagcagc acttcaattg gtcgata                                    27

<210> SEQ ID NO 414
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 414
tgcagcagca cttcaattgg tcgataa                                    27

<210> SEQ ID NO 415
<211> LENGTH: 27
<212> TYPE: DNA
<213> ORGANISM: Artificial Sequence
<220> FEATURE:
<223> OTHER INFORMATION: Primer/Probe/Quencher Sequence

```
<400> SEQUENCE: 415
gcagcagcac ttcaattggt cgataac                                               27

<210> SEQ ID NO 416
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 416
cagcagcact tcaattggtc gataact                                               27

<210> SEQ ID NO 417
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 417
agcagcactt caattggtcg ataactg                                               27

<210> SEQ ID NO 418
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 418
gcagcacttc aattggtcga taactgg                                               27

<210> SEQ ID NO 419
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 419
cagcacttca attggtcgat aactggt                                               27

<210> SEQ ID NO 420
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 420
agcacttcaa ttggtcgata actggta                                               27

<210> SEQ ID NO 421
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 421
gcacttcaat tggtcgataa ctggtat                                               27

<210> SEQ ID NO 422
```

```
<211> LENGTH: 21
<212> TYPE: DNA
<213> ORGANISM: Artificial Sequence
<220> FEATURE:
<223> OTHER INFORMATION: Primer/Probe/Quencher Sequence

<400> SEQUENCE: 422
gcagcacttc aattggtcga t                                       21

<210> SEQ ID NO 423
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 423
gcagcacttc aattggtcga taac                                    24

<210> SEQ ID NO 424
<211> LENGTH: 45
<212> TYPE: DNA
<213> ORGANISM: Artificial Sequence
<220> FEATURE:
<223> OTHER INFORMATION: Primer/Probe/Quencher Sequence

<400> SEQUENCE: 424
aattggtgca attgcctgga caaacagaat acatattgca tacca             45

<210> SEQ ID NO 425
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 425
aattggtgca attgcctgga caaacagaat aca                          33

<210> SEQ ID NO 426
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 426
attggtgcaa ttgcctggac aaacagaata cat                          33

<210> SEQ ID NO 427
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 427
ttggtgcaat tgcctggaca aacagaatac ata                          33

<210> SEQ ID NO 428
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 428
```
tggtgcaatt gcctggacaa acagaataca tat    33

<210> SEQ ID NO 429
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 429
ggtgcaattg cctggacaaa cagaatacat att    33

<210> SEQ ID NO 430
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 430
gtgcaattgc ctggacaaac agaatacata ttg    33

<210> SEQ ID NO 431
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 431
tgcaattgcc tggacaaaca gaatacatat tgc    33

<210> SEQ ID NO 432
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 432
gcaattgcct ggacaaacag aatacatatt gca    33

<210> SEQ ID NO 433
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 433
caattgcctg gacaaacaga atacatattg cat    33

<210> SEQ ID NO 434
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 434
aattgcctgg acaaacagaa tacatattgc ata    33

<210> SEQ ID NO 435
<211> LENGTH: 33
<212> TYPE: DNA

```
<213> ORGANISM: Artificial Sequence
<220> FEATURE:
<223> OTHER INFORMATION: Primer/Probe/Quencher Sequence

<400> SEQUENCE: 435
attgcctgga caaacagaat acatattgca tac                           33

<210> SEQ ID NO 436
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 436
ttgcctggac aaacagaata catattgcat acc                           33

<210> SEQ ID NO 437
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 437
tgcctggaca aacagaatac atattgcata cca                           33

<210> SEQ ID NO 438
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 438
aattgcctgg acaaacagaa tacatat                                  27

<210> SEQ ID NO 439
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 439
tgcctggaca aacagaatac atattgca                                 28

<210> SEQ ID NO 440
<211> LENGTH: 45
<212> TYPE: DNA
<213> ORGANISM: Artificial Sequence
<220> FEATURE:
<223> OTHER INFORMATION: Primer/Probe/Quencher Sequence

<400> SEQUENCE: 440
tggtatgcaa tatgtattct gtttgtccag gcaattgcac caatt              45

<210> SEQ ID NO 441
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 441
tggtatgcaa tatgtattct gtttgtccag gca                           33
```

<210> SEQ ID NO 442
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 442
ggtatgcaat atgtattctg tttgtccagg caa    33

<210> SEQ ID NO 443
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 443
gtatgcaata tgtattctgt tgtccaggc aat    33

<210> SEQ ID NO 444
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 444
tatgcaatat gtattctgtt tgtccaggca att    33

<210> SEQ ID NO 445
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 445
atgcaatatg tattctgttt gtccaggcaa ttg    33

<210> SEQ ID NO 446
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 446
tgcaatatgt attctgtttg tccaggcaat tgc    33

<210> SEQ ID NO 447
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 447
gcaatatgta ttctgtttgt ccaggcaatt gca    33

<210> SEQ ID NO 448
<211> LENGTH: 33
<212> TYPE: DNA
<213> ORGANISM: Artificial Sequence
<220> FEATURE:

<223> OTHER INFORMATION: Primer/Probe/Quencher Sequence

<400> SEQUENCE: 448
caatatgtat tctgtttgtc caggcaattg cac            33

<210> SEQ ID NO 449
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 449
aatatgtatt ctgtttgtcc aggcaattgc acc            33

<210> SEQ ID NO 450
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 450
atatgtattc tgtttgtcca ggcaattgca cca            33

<210> SEQ ID NO 451
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 451
tatgtattct gtttgtccag gcaattgcac caa            33

<210> SEQ ID NO 452
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 452
atgtattctg tttgtccagg caattgcacc aat            33

<210> SEQ ID NO 453
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 453
tgtattctgt ttgtccaggc aattgcacca att            33

<210> SEQ ID NO 454
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 454
atatgtattc tgtttgtcca ggcaatt            27

```
<210> SEQ ID NO 455
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 455
tgcaatatgt attctgtttg tccaggca                                28

<210> SEQ ID NO 456
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 456
gcagggactt tcgttgcgtt gt                                      22

<210> SEQ ID NO 457
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 457
cagcaaaaaa tccccatgcc acca                                    24

<210> SEQ ID NO 458
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 458
tggtggcatg gggatttttt gctg                                    24

<210> SEQ ID NO 459
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 459
accagacaag gtaatttgag acgagcc                                 27

<210> SEQ ID NO 460
<211> LENGTH: 31
<212> TYPE: DNA
<213> ORGANISM: Artificial Sequence
<220> FEATURE:
<223> OTHER INFORMATION: Primer/Probe/Quencher Sequence

<400> SEQUENCE: 460
ctttcatcgt tggtttaaca tggtatcaaa g                            31

<210> SEQ ID NO 461
<211> LENGTH: 31
<212> TYPE: DNA
<213> ORGANISM: Artificial Sequence
<220> FEATURE:
<223> OTHER INFORMATION: Primer/Probe/Quencher Sequence
```

```
<400> SEQUENCE: 461
ctttgatacc atgttaaacc aacgatgaaa g                              31

<210> SEQ ID NO 462
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 462
tttcatcgtt ggtttaacat ggtatcaa                                  28

<210> SEQ ID NO 463
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 463
ccagacaagg taatttgaga cgagcctg                                  28

<210> SEQ ID NO 464
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 464
caggctcgtc tcaaattacc ttgtctgg                                  28

<210> SEQ ID NO 465
<211> LENGTH: 36
<212> TYPE: DNA
<213> ORGANISM: Artificial Sequence
<220> FEATURE:
<223> OTHER INFORMATION: Primer/Probe/Quencher Sequence

<400> SEQUENCE: 465
ggttactgca agtgtagcga aaacacaaaa aggcaa                         36

<210> SEQ ID NO 466
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 466
ggttactgca agtgtagcga aaac                                      24

<210> SEQ ID NO 467
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 467
gttactgcaa gtgtagcgaa aaca                                      24

<210> SEQ ID NO 468
<211> LENGTH: 24
```

<212> TYPE: DNA
<213> ORGANISM: Artificial Sequence
<220> FEATURE:
<223> OTHER INFORMATION: Primer/Probe/Quencher Sequence

<400> SEQUENCE: 468
ttactgcaag tgtagcgaaa acac                                          24

<210> SEQ ID NO 469
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 469
tactgcaagt gtagcgaaaa caca                                          24

<210> SEQ ID NO 470
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 470
actgcaagtg tagcgaaaac acaa                                          24

<210> SEQ ID NO 471
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 471
ctgcaagtgt agcgaaaaca caaa                                          24

<210> SEQ ID NO 472
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 472
tgcaagtgta gcgaaaacac aaaa                                          24

<210> SEQ ID NO 473
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 473
gcaagtgtag cgaaaacaca aaaa                                          24

<210> SEQ ID NO 474
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 474

```
caagtgtagc gaaaacacaa aaag                                          24
```

<210> SEQ ID NO 475
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 475

```
aagtgtagcg aaaacacaaa aagg                                          24
```

<210> SEQ ID NO 476
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 476

```
agtgtagcga aaacacaaaa aggc                                          24
```

<210> SEQ ID NO 477
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 477

```
gtgtagcgaa aacacaaaaa ggca                                          24
```

<210> SEQ ID NO 478
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 478

```
tgtagcgaaa acacaaaaag gcaa                                          24
```

<210> SEQ ID NO 479
<211> LENGTH: 18
<212> TYPE: DNA
<213> ORGANISM: Artificial Sequence
<220> FEATURE:
<223> OTHER INFORMATION: Primer/Probe/Quencher Sequence

<400> SEQUENCE: 479

```
aagtgtagcg aaaacaca                                                 18
```

<210> SEQ ID NO 480
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 480

```
gccaaaccaa ctatgaactg tctggac                                       27
```

<210> SEQ ID NO 481
<211> LENGTH: 22
<212> TYPE: DNA
<213> ORGANISM: Artificial Sequence

```
<220> FEATURE:
<223> OTHER INFORMATION: Primer/Probe/Quencher Sequence

<400> SEQUENCE: 481
tggcatgggg attttttgct gc                                              22

<210> SEQ ID NO 482
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 482
taacaatgag tttaattatt gcagctaaca taa                                  33

<210> SEQ ID NO 483
<211> LENGTH: 34
<212> TYPE: DNA
<213> ORGANISM: Artificial Sequence
<220> FEATURE:
<223> OTHER INFORMATION: Primer/Probe/Quencher Sequence

<400> SEQUENCE: 483
atatattcgc tatatcttct tgcggctgca gttt                                 34

<210> SEQ ID NO 484
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 484
atatattcgc tatatcttct tg                                              22

<210> SEQ ID NO 485
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 485
tatattcgct atatcttctt gc                                              22

<210> SEQ ID NO 486
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 486
atattcgcta tatcttcttg cg                                              22

<210> SEQ ID NO 487
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 487
tattcgctat atcttcttgc gg                                              22
```

```
<210> SEQ ID NO 488
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 488
attcgctata tcttcttgcg gc                                              22

<210> SEQ ID NO 489
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 489
ttcgctatat cttcttgcgg ct                                              22

<210> SEQ ID NO 490
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 490
tcgctatatc ttcttgcggc tg                                              22

<210> SEQ ID NO 491
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 491
cgctatatct tcttgcggct gc                                              22

<210> SEQ ID NO 492
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 492
gctatatctt cttgcggctg ca                                              22

<210> SEQ ID NO 493
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 493
ctatatcttc ttgcggctgc ag                                              22

<210> SEQ ID NO 494
<211> LENGTH: 22
<212> TYPE: DNA
<213> ORGANISM: Artificial Sequence
<220> FEATURE:
<223> OTHER INFORMATION: Primer/Probe/Quencher Sequence
```

<400> SEQUENCE: 494
tatatcttct tgcggctgca gt                                              22

<210> SEQ ID NO 495
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 495
atatcttctt gcggctgcag tt                                              22

<210> SEQ ID NO 496
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 496
tatcttcttg cggctgcagt tt                                              22

<210> SEQ ID NO 497
<211> LENGTH: 16
<212> TYPE: DNA
<213> ORGANISM: Artificial Sequence
<220> FEATURE:
<223> OTHER INFORMATION: Primer/Probe/Quencher Sequence

<400> SEQUENCE: 497
ctatatcttc ttgcgg                                                     16

<210> SEQ ID NO 498
<211> LENGTH: 41
<212> TYPE: DNA
<213> ORGANISM: Artificial Sequence
<220> FEATURE:
<223> OTHER INFORMATION: Primer/Probe/Quencher Sequence

<400> SEQUENCE: 498
cttactacgg cattgacagt ttattatttt ccaaaaactg c                         41

<210> SEQ ID NO 499
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 499
cttactacgg cattgacagt ttattattt                                       29

<210> SEQ ID NO 500
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 500
ttactacggc attgacagtt tattatttt                                       29

<210> SEQ ID NO 501

```
<210> SEQ ID NO 501
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 501
tactacggca ttgacagttt attattttc                                29

<210> SEQ ID NO 502
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 502
actacggcat tgacagttta ttattttcc                                29

<210> SEQ ID NO 503
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 503
ctacggcatt gacagtttat tattttcca                                29

<210> SEQ ID NO 504
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 504
tacggcattg acagtttatt attttccaa                                29

<210> SEQ ID NO 505
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 505
acggcattga cagtttatta ttttccaaa                                29

<210> SEQ ID NO 506
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 506
cggcattgac agtttattat tttccaaaa                                29

<210> SEQ ID NO 507
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 507
```

-continued

```
ggcattgaca gtttattatt ttccaaaaa                                        29

<210> SEQ ID NO 508
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 508
gcattgacag tttattattt tccaaaaac                                        29

<210> SEQ ID NO 509
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 509
cattgacagt ttattatttt ccaaaaact                                        29

<210> SEQ ID NO 510
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 510
attgacagtt tattattttc caaaaactg                                        29

<210> SEQ ID NO 511
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 511
ttgacagttt attattttcc aaaaactgc                                        29

<210> SEQ ID NO 512
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 512
gcattgacag tttattattt tcc                                              23

<210> SEQ ID NO 513
<211> LENGTH: 41
<212> TYPE: DNA
<213> ORGANISM: Artificial Sequence
<220> FEATURE:
<223> OTHER INFORMATION: Primer/Probe/Quencher Sequence

<400> SEQUENCE: 513
gcagtttttg gaaaataata aactgtcaat gccgtagtaa g                          41

<210> SEQ ID NO 514
<211> LENGTH: 29
<212> TYPE: DNA
```

```
<213> ORGANISM: Artificial Sequence
<220> FEATURE:
<223> OTHER INFORMATION: Primer/Probe/Quencher Sequence

<400> SEQUENCE: 514 gcagttttg gaaaataata aactgtcaa                                        29

<210> SEQ ID NO 515
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 515 cagttttgg aaaataataa actgtcaat                                        29

<210> SEQ ID NO 516
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 516 agttttgga aataataaa ctgtcaatg                                         29

<210> SEQ ID NO 517
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 517 gttttggaa aataataaac tgtcaatgc                                        29

<210> SEQ ID NO 518
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 518 ttttggaaa ataataaact gtcaatgcc                                        29

<210> SEQ ID NO 519
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 519 tttggaaaa taataaactg tcaatgccg                                        29

<210> SEQ ID NO 520
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 520
tttggaaaat aataaactgt caatgccgt                                       29
```

<210> SEQ ID NO 521
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 521
ttggaaaata ataaactgtc aatgccgta                                29

<210> SEQ ID NO 522
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 522
tggaaaataa taaactgtca atgccgtag                                29

<210> SEQ ID NO 523
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 523
ggaaaataat aaactgtcaa tgccgtagt                                29

<210> SEQ ID NO 524
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 524
gaaaataata aactgtcaat gccgtagta                                29

<210> SEQ ID NO 525
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 525
aaaataataa actgtcaatg ccgtagtaa                                29

<210> SEQ ID NO 526
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 526
aaataataaa ctgtcaatgc cgtagtaag                                29

<210> SEQ ID NO 527
<211> LENGTH: 23
<212> TYPE: DNA
<213> ORGANISM: Artificial Sequence
<220> FEATURE:

<223> OTHER INFORMATION: Primer/Probe/Quencher Sequence

<400> SEQUENCE: 527
ggaaaataat aaactgtcaa tgc                                    23

<210> SEQ ID NO 528
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 528
tactggaaaa aagcaccccc gtactt                                 26

<210> SEQ ID NO 529
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 529
tcaattaaat tatccttcat agcctgttgt ttt                         33

<210> SEQ ID NO 530
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 530
aaaacaacag gctatgaagg ataatttaat tga                         33

<210> SEQ ID NO 531
<211> LENGTH: 32
<212> TYPE: DNA
<213> ORGANISM: Artificial Sequence
<220> FEATURE:
<223> OTHER INFORMATION: Primer/Probe/Quencher Sequence

<400> SEQUENCE: 531
cacccccata taaagtaat ttttcatctg ag                           32

<210> SEQ ID NO 532
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 532
tgggtgggac atactcctcg gcataa                                 26

<210> SEQ ID NO 533
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 533
ttatgccgag gagtatgtcc caccca                                 26

```
<210> SEQ ID NO 534
<211> LENGTH: 30
<212> TYPE: DNA
<213> ORGANISM: Artificial Sequence
<220> FEATURE:
<223> OTHER INFORMATION: Primer/Probe/Quencher Sequence

<400> SEQUENCE: 534
catactcctc ggcataacat tactcagatg                                    30

<210> SEQ ID NO 535
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 535
acgctccaat caccccata taaaagtaa                                      29

<210> SEQ ID NO 536
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 536
ttacttttat atgggggtga ttggagcgt                                     29

<210> SEQ ID NO 537
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 537
tttggaaaat aataaactgt caatgccg                                      28

<210> SEQ ID NO 538
<211> LENGTH: 36
<212> TYPE: DNA
<213> ORGANISM: Artificial Sequence
<220> FEATURE:
<223> OTHER INFORMATION: Primer/Probe/Quencher Sequence

<400> SEQUENCE: 538
ctgtaaatag aatttctgag gcttatctgg ctgttc                             36

<210> SEQ ID NO 539
<211> LENGTH: 36
<212> TYPE: DNA
<213> ORGANISM: Artificial Sequence
<220> FEATURE:
<223> OTHER INFORMATION: Primer/Probe/Quencher Sequence

<400> SEQUENCE: 539
gaacagccag ataagcctca gaaattctat ttacag                             36

<210> SEQ ID NO 540
<211> LENGTH: 36
<212> TYPE: DNA
<213> ORGANISM: Artificial Sequence
<220> FEATURE:
<223> OTHER INFORMATION: Primer/Probe/Quencher Sequence
```

<400> SEQUENCE: 540 ggggtgatt ggagcgttaa ctggacctat ttcgat                36

<210> SEQ ID NO 541
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 541 ggggtgatt ggagcgttaa ctgg                24

<210> SEQ ID NO 542
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 542
ggggtgattg gagcgttaac tgga                24

<210> SEQ ID NO 543
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 543
gggtgattgg agcgttaact ggac                24

<210> SEQ ID NO 544
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 544
ggtgattgga gcgttaactg gacc                24

<210> SEQ ID NO 545
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 545
gtgattggag cgttaactgg acct                24

<210> SEQ ID NO 546
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 546
tgattggagc gttaactgga ccta                24

<210> SEQ ID NO 547
<211> LENGTH: 24

```
<212> TYPE: DNA
<213> ORGANISM: Artificial Sequence
<220> FEATURE:
<223> OTHER INFORMATION: Primer/Probe/Quencher Sequence

<400> SEQUENCE: 547
gattggagcg ttaactggac ctat                                          24

<210> SEQ ID NO 548
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 548
attggagcgt taactggacc tatt                                          24

<210> SEQ ID NO 549
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 549
ttggagcgtt aactggacct attt                                          24

<210> SEQ ID NO 550
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 550
tggagcgtta actggaccta tttc                                          24

<210> SEQ ID NO 551
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 551
ggagcgttaa ctggacctat ttcg                                          24

<210> SEQ ID NO 552
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 552
gagcgttaac tggacctatt tcga                                          24

<210> SEQ ID NO 553
<211> LENGTH: 24
<212> TYPE: DNA
<213> ORGANISM: Artificial Sequence
<220> FEATURE:
<223> OTHER INFORMATION: Primer/Probe/Quencher Sequence

<400> SEQUENCE: 553
```

```
agcgttaact ggacctattt cgat                                          24
```

<210> SEQ ID NO 554
<211> LENGTH: 18
<212> TYPE: DNA
<213> ORGANISM: Artificial Sequence
<220> FEATURE:
<223> OTHER INFORMATION: Primer/Probe/Quencher Sequence

<400> SEQUENCE: 554

```
tggagcgtta actggacc                                                 18
```

<210> SEQ ID NO 555
<211> LENGTH: 32
<212> TYPE: DNA
<213> ORGANISM: Artificial Sequence
<220> FEATURE:
<223> OTHER INFORMATION: Primer/Probe/Quencher Sequence

<400> SEQUENCE: 555

```
tttcacaagg agttaataga tattcagcag aa                                 32
```

<210> SEQ ID NO 556
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 556

```
cctcatcgtt gttatctatg gtgggct                                       27
```

<210> SEQ ID NO 557
<211> LENGTH: 30
<212> TYPE: DNA
<213> ORGANISM: Artificial Sequence
<220> FEATURE:
<223> OTHER INFORMATION: Primer/Probe/Quencher Sequence

<400> SEQUENCE: 557

```
gtagtaagaa cagccagata agcctcagaa                                    30
```

<210> SEQ ID NO 558
<211> LENGTH: 34
<212> TYPE: DNA
<213> ORGANISM: Artificial Sequence
<220> FEATURE:
<223> OTHER INFORMATION: Primer/Probe/Quencher Sequence

<400> SEQUENCE: 558

```
tatcctccca aaacttctag gcccgatatt tttt                               34
```

<210> SEQ ID NO 559
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 559

```
tatcctccca aaacttctag gc                                            22
```

<210> SEQ ID NO 560
<211> LENGTH: 22
<212> TYPE: DNA
<213> ORGANISM: Artificial Sequence

```
<220> FEATURE:
<223> OTHER INFORMATION: Primer/Probe/Quencher Sequence

<400> SEQUENCE: 560
atcctcccaa aacttctagg cc                                              22

<210> SEQ ID NO 561
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 561
tcctcccaaa acttctaggc cc                                              22

<210> SEQ ID NO 562
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 562
cctcccaaaa cttctaggcc cg                                              22

<210> SEQ ID NO 563
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 563
ctcccaaaac ttctaggccc ga                                              22

<210> SEQ ID NO 564
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 564
tcccaaaact tctaggcccg at                                              22

<210> SEQ ID NO 565
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 565
cccaaaactt ctaggcccga ta                                              22

<210> SEQ ID NO 566
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 566
ccaaaacttc taggcccgat at                                              22
```

```
<210> SEQ ID NO 567
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 567
caaaacttct aggcccgata tt                                              22

<210> SEQ ID NO 568
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 568
aaaacttcta ggcccgatat tt                                              22

<210> SEQ ID NO 569
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 569
aaacttctag gcccgatatt tt                                              22

<210> SEQ ID NO 570
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 570
aacttctagg cccgatattt tt                                              22

<210> SEQ ID NO 571
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 571
acttctaggc ccgatatttt tt                                              22

<210> SEQ ID NO 572
<211> LENGTH: 16
<212> TYPE: DNA
<213> ORGANISM: Artificial Sequence
<220> FEATURE:
<223> OTHER INFORMATION: Primer/Probe/Quencher Sequence

<400> SEQUENCE: 572
aaaacttcta ggcccg                                                     16

<210> SEQ ID NO 573
<211> LENGTH: 39
<212> TYPE: DNA
<213> ORGANISM: Artificial Sequence
<220> FEATURE:
<223> OTHER INFORMATION: Primer/Probe/Quencher Sequence
```

```
<400> SEQUENCE: 573 aggcttttc acgtttgata gattcgcggt agaaaaaat                              39

<210> SEQ ID NO 574
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 574 aggcttttc acgtttgata gattcgc                                           27

<210> SEQ ID NO 575
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 575 ggcttttca cgtttgatag attcgcg                                           27

<210> SEQ ID NO 576
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 576
gctttttcac gtttgataga ttcgcgg                                          27

<210> SEQ ID NO 577
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 577
ctttttcacg tttgatagat tcgcggt                                          27

<210> SEQ ID NO 578
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 578
tttttcacgt ttgatagatt cgcggta                                          27

<210> SEQ ID NO 579
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 579
ttttcacgtt tgatagattc gcggtag                                          27

<210> SEQ ID NO 580
```

```
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 580
tttcacgttt gatagattcg cggtaga                                              27

<210> SEQ ID NO 581
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 581
ttcacgtttg atagattcgc ggtagaa                                              27

<210> SEQ ID NO 582
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 582
tcacgtttga tagattcgcg gtagaaa                                              27

<210> SEQ ID NO 583
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 583
cacgtttgat agattcgcgg tagaaaa                                              27

<210> SEQ ID NO 584
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 584
acgtttgata gattcgcggt agaaaaa                                              27

<210> SEQ ID NO 585
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 585
cgtttgatag attcgcggta gaaaaaa                                              27

<210> SEQ ID NO 586
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 586
```

```
gtttgataga ttcgcggtag aaaaaat                                           27

<210> SEQ ID NO 587
<211> LENGTH: 21
<212> TYPE: DNA
<213> ORGANISM: Artificial Sequence
<220> FEATURE:
<223> OTHER INFORMATION: Primer/Probe/Quencher Sequence

<400> SEQUENCE: 587
cacgtttgat agattcgcgg t                                                 21

<210> SEQ ID NO 588
<211> LENGTH: 39
<212> TYPE: DNA
<213> ORGANISM: Artificial Sequence
<220> FEATURE:
<223> OTHER INFORMATION: Primer/Probe/Quencher Sequence

<400> SEQUENCE: 588 atttttcta ccgcgaatct atcaaacgtg aaaaagcct                               39

<210> SEQ ID NO 589
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 589
attttttcta ccgcgaatct atcaaac                                           27

<210> SEQ ID NO 590
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 590 tttttctac cgcgaatcta tcaaacg                                            27

<210> SEQ ID NO 591
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 591
tttttctacc gcgaatctat caaacgt                                           27

<210> SEQ ID NO 592
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 592
ttttctaccg cgaatctatc aaacgtg                                           27

<210> SEQ ID NO 593
<211> LENGTH: 27
<212> TYPE: DNA
```

```
<213> ORGANISM: Artificial Sequence
<220> FEATURE:
<223> OTHER INFORMATION: Primer/Probe/Quencher Sequence

<400> SEQUENCE: 593
tttctaccgc gaatctatca aacgtga                                    27

<210> SEQ ID NO 594
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 594
ttctaccgcg aatctatcaa acgtgaa                                    27

<210> SEQ ID NO 595
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 595
tctaccgcga atctatcaaa cgtgaaa                                    27

<210> SEQ ID NO 596
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 596
ctaccgcgaa tctatcaaac gtgaaaa                                    27

<210> SEQ ID NO 597
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 597
taccgcgaat ctatcaaacg tgaaaaa                                    27

<210> SEQ ID NO 598
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 598
accgcgaatc tatcaaacgt gaaaaag                                    27

<210> SEQ ID NO 599
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 599
ccgcgaatct atcaaacgtg aaaaagc                                    27
```

<210> SEQ ID NO 600
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 600
cgcgaatcta tcaaacgtga aaaagcc                              27

<210> SEQ ID NO 601
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 601
gcgaatctat caaacgtgaa aagcct                               27

<210> SEQ ID NO 602
<211> LENGTH: 21
<212> TYPE: DNA
<213> ORGANISM: Artificial Sequence
<220> FEATURE:
<223> OTHER INFORMATION: Primer/Probe/Quencher Sequence

<400> SEQUENCE: 602
accgcgaatc tatcaaacgt g                                    21

<210> SEQ ID NO 603
<211> LENGTH: 34
<212> TYPE: DNA
<213> ORGANISM: Artificial Sequence
<220> FEATURE:
<223> OTHER INFORMATION: Primer/Probe/Quencher Sequence

<400> SEQUENCE: 603
atattacaaa ctgggattgg acgtggataa aaaa                      34

<210> SEQ ID NO 604
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 604
atattacaaa ctgggattgg ac                                   22

<210> SEQ ID NO 605
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 605
tattacaaac tgggattgga cg                                   22

<210> SEQ ID NO 606
<211> LENGTH: 22
<212> TYPE: DNA
<213> ORGANISM: Artificial Sequence
<220> FEATURE:

<223> OTHER INFORMATION: Primer/Probe/Quencher Sequence

<400> SEQUENCE: 606
attacaaact gggattggac gt                                              22

<210> SEQ ID NO 607
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 607
ttacaaactg ggattggacg tg                                              22

<210> SEQ ID NO 608
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 608
tacaaactgg gattggacgt gg                                              22

<210> SEQ ID NO 609
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 609
acaaactggg attggacgtg ga                                              22

<210> SEQ ID NO 610
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 610
caaactggga ttggacgtgg at                                              22

<210> SEQ ID NO 611
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 611
aaactgggat tggacgtgga ta                                              22

<210> SEQ ID NO 612
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 612
aactgggatt ggacgtggat aa                                              22

```
<210> SEQ ID NO 613
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 613
actgggattg gacgtggata aa                                              22

<210> SEQ ID NO 614
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 614
ctgggattgg acgtggataa aa                                              22

<210> SEQ ID NO 615
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 615
tgggattgga cgtggataaa aa                                              22

<210> SEQ ID NO 616
<211> LENGTH: 22
<212> TYPE: DNA
<213> ORGANISM: Artificial Sequence
<220> FEATURE:
<223> OTHER INFORMATION: Primer/Probe/Quencher Sequence

<400> SEQUENCE: 616
gggattggac gtggataaaa aa                                              22

<210> SEQ ID NO 617
<211> LENGTH: 16
<212> TYPE: DNA
<213> ORGANISM: Artificial Sequence
<220> FEATURE:
<223> OTHER INFORMATION: Primer/Probe/Quencher Sequence

<400> SEQUENCE: 617
actgggattg gacgtg                                                     16

<210> SEQ ID NO 618
<211> LENGTH: 38
<212> TYPE: DNA
<213> ORGANISM: Artificial Sequence
<220> FEATURE:
<223> OTHER INFORMATION: Primer/Probe/Quencher Sequence

<400> SEQUENCE: 618
ctggtggagg aagcaagggt aatttttaac caggtgat                             38

<210> SEQ ID NO 619
<211> LENGTH: 26
<212> TYPE: DNA
<213> ORGANISM: Artificial Sequence
<220> FEATURE:
<223> OTHER INFORMATION: Primer/Probe/Quencher Sequence
```

<400> SEQUENCE: 619
ctggtggagg aagcaagggt aatttt                                           26

<210> SEQ ID NO 620
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 620
tggtggagga agcaagggta attttt                                           26

<210> SEQ ID NO 621
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 621
ggtggaggaa gcaagggtaa ttttta                                           26

<210> SEQ ID NO 622
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 622
gtggaggaag caagggtaat ttttaa                                           26

<210> SEQ ID NO 623
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 623
tggaggaagc aagggtaatt tttaac                                           26

<210> SEQ ID NO 624
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 624
ggaggaagca agggtaattt ttaacc                                           26

<210> SEQ ID NO 625
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 625
gaggaagcaa gggtaatttt taacca                                           26

<210> SEQ ID NO 626
<211> LENGTH: 26

```
<212> TYPE: DNA
<213> ORGANISM: Artificial Sequence
<220> FEATURE:
<223> OTHER INFORMATION: Primer/Probe/Quencher Sequence

<400> SEQUENCE: 626
aggaagcaag ggtaattttt aaccag                                      26

<210> SEQ ID NO 627
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 627
ggaagcaagg gtaatttta accagg                                       26

<210> SEQ ID NO 628
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 628
gaagcaaggg taatttttaa ccaggt                                      26

<210> SEQ ID NO 629
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 629
aagcaagggt aatttttaac caggtg                                      26

<210> SEQ ID NO 630
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 630
agcaagggta atttttaacc aggtga                                      26

<210> SEQ ID NO 631
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 631
gcaagggtaa tttttaacca ggtgat                                      26

<210> SEQ ID NO 632
<211> LENGTH: 20
<212> TYPE: DNA
<213> ORGANISM: Artificial Sequence
<220> FEATURE:
<223> OTHER INFORMATION: Primer/Probe/Quencher Sequence

<400> SEQUENCE: 632
```

```
gaagcaaggg taatttttaa                                             20

<210> SEQ ID NO 633
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 633
aagcaagggt aattttaac cag                                          23

<210> SEQ ID NO 634
<211> LENGTH: 45
<212> TYPE: DNA
<213> ORGANISM: Artificial Sequence
<220> FEATURE:
<223> OTHER INFORMATION: Primer/Probe/Quencher Sequence

<400> SEQUENCE: 634
aacgttacga aatcaatgtt gcaagcattc aagaatcacc tggtt                 45

<210> SEQ ID NO 635
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 635
aacgttacga aatcaatgtt gcaagcattc aag                              33

<210> SEQ ID NO 636
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 636
acgttacgaa atcaatgttg caagcattca aga                              33

<210> SEQ ID NO 637
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 637
cgttacgaaa tcaatgttgc aagcattcaa gaa                              33

<210> SEQ ID NO 638
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 638
gttacgaaat caatgttgca agcattcaag aat                              33

<210> SEQ ID NO 639
<211> LENGTH: 33
<212> TYPE: DNA
<213> ORGANISM: Artificial Sequence
```

```
<220> FEATURE:
<223> OTHER INFORMATION: Primer/Probe/Quencher Sequence

<400> SEQUENCE: 639
ttacgaaatc aatgttgcaa gcattcaaga atc                              33

<210> SEQ ID NO 640
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 640
tacgaaatca atgttgcaag cattcaagaa tca                              33

<210> SEQ ID NO 641
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 641
acgaaatcaa tgttgcaagc attcaagaat cac                              33

<210> SEQ ID NO 642
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 642
cgaaatcaat gttgcaagca ttcaagaatc acc                              33

<210> SEQ ID NO 643
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 643
gaaatcaatg ttgcaagcat tcaagaatca cct                              33

<210> SEQ ID NO 644
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 644
aaatcaatgt tgcaagcatt caagaatcac ctg                              33

<210> SEQ ID NO 645
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 645
aatcaatgtt gcaagcattc aagaatcacc tgg                              33
```

<210> SEQ ID NO 646
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 646
atcaatgttg caagcattca agaatcacct ggt                         33

<210> SEQ ID NO 647
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 647
tcaatgttgc aagcattcaa gaatcacctg gtt                         33

<210> SEQ ID NO 648
<211> LENGTH: 27
<212> TYPE: DNA
<213> ORGANISM: Artificial Sequence
<220> FEATURE:
<223> OTHER INFORMATION: Primer/Probe/Quencher Sequence

<400> SEQUENCE: 648
aaatcaatgt tgcaagcatt caagaat                                27

<210> SEQ ID NO 649
<211> LENGTH: 43
<212> TYPE: DNA
<213> ORGANISM: Artificial Sequence
<220> FEATURE:
<223> OTHER INFORMATION: Primer/Probe/Quencher Sequence

<400> SEQUENCE: 649
cctcggtgaa atcaatgttg caagcattca agaatcaccg agg              43

<210> SEQ ID NO 650
<211> LENGTH: 43
<212> TYPE: DNA
<213> ORGANISM: Artificial Sequence
<220> FEATURE:
<223> OTHER INFORMATION: Primer/Probe/Quencher Sequence

<400> SEQUENCE: 650
cctcgacgaa atcaatgttg caagcattca agaatcgtcg agg              43

<210> SEQ ID NO 651
<211> LENGTH: 47
<212> TYPE: DNA
<213> ORGANISM: Artificial Sequence
<220> FEATURE:
<223> OTHER INFORMATION: Primer/Probe/Quencher Sequence

<400> SEQUENCE: 651
gcagcctcgc gaaatcaatg ttgcaagcat tcaagaatcg aggctgc          47

<210> SEQ ID NO 652
<211> LENGTH: 52
<212> TYPE: DNA
<213> ORGANISM: Artificial Sequence
<220> FEATURE:
<223> OTHER INFORMATION: Primer/Probe/Quencher Sequence -continued

```
<400> SEQUENCE: 652
cccagcctcg ttacgaaatc aatgttgcaa gcattcaaga atcgaggctg gg          52

<210> SEQ ID NO 653
<211> LENGTH: 50
<212> TYPE: DNA
<213> ORGANISM: Artificial Sequence
<220> FEATURE:
<223> OTHER INFORMATION: Primer/Probe/Quencher Sequence

<400> SEQUENCE: 653
cccagcctcg acgaaatcaa tgttgcaagc attcaagaat cgaggctggg             50

<210> SEQ ID NO 654
<211> LENGTH: 35
<212> TYPE: DNA
<213> ORGANISM: Artificial Sequence
<220> FEATURE:
<223> OTHER INFORMATION: Primer/Probe/Quencher Sequence

<400> SEQUENCE: 654
ttcttgaatg cttgcaacat tgatttcgta acgtt                             35

<210> SEQ ID NO 655
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 655
ttcttgaatg cttgcaacat tga                                          23

<210> SEQ ID NO 656
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 656
tcttgaatgc ttgcaacatt gat                                          23

<210> SEQ ID NO 657
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 657
cttgaatgct tgcaacattg att                                          23

<210> SEQ ID NO 658
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 658
ttgaatgctt gcaacattga ttt                                          23

<210> SEQ ID NO 659
```

```
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 659
tgaatgcttg caacattgat ttc                                          23

<210> SEQ ID NO 660
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 660
gaatgcttgc aacattgatt tcg                                          23

<210> SEQ ID NO 661
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 661
aatgcttgca acattgattt cgt                                          23

<210> SEQ ID NO 662
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 662
atgcttgcaa cattgatttc gta                                          23

<210> SEQ ID NO 663
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 663
tgcttgcaac attgatttcg taa                                          23

<210> SEQ ID NO 664
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 664
gcttgcaaca ttgatttcgt aac                                          23

<210> SEQ ID NO 665
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 665
```
cttgcaacat tgatttcgta acg                                           23

<210> SEQ ID NO 666
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 666
ttgcaacatt gatttcgtaa cgt                                           23

<210> SEQ ID NO 667
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 667
tgcaacattg atttcgtaac gtt                                           23

<210> SEQ ID NO 668
<211> LENGTH: 17
<212> TYPE: DNA
<213> ORGANISM: Artificial Sequence
<220> FEATURE:
<223> OTHER INFORMATION: Primer/Probe/Quencher Sequence

<400> SEQUENCE: 668
gcttgcaaca ttgattt                                                  17

<210> SEQ ID NO 669
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 669
gtgattcttg aatgcttgca acattgattt cgt                                33

<210> SEQ ID NO 670
<211> LENGTH: 28
<212> TYPE: DNA
<213> ORGANISM: Artificial Sequence
<220> FEATURE:
<223> OTHER INFORMATION: Primer/Probe/Quencher Sequence

<400> SEQUENCE: 670
tcttgaatgc ttgcaacatt gatttcgt                                      28

<210> SEQ ID NO 671
<211> LENGTH: 35
<212> TYPE: DNA
<213> ORGANISM: Artificial Sequence
<220> FEATURE:
<223> OTHER INFORMATION: Primer/Probe/Quencher Sequence

<400> SEQUENCE: 671
ctatcccgat gagctaatgg cggtatgtga tggtg                              35

<210> SEQ ID NO 672
<211> LENGTH: 23
<212> TYPE: DNA

```
<213> ORGANISM: Artificial Sequence
<220> FEATURE:
<223> OTHER INFORMATION: Primer/Probe/Quencher Sequence

<400> SEQUENCE: 672
ctatcccgat gagctaatgg cgg                                              23

<210> SEQ ID NO 673
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 673
tatcccgatg agctaatggc ggt                                              23

<210> SEQ ID NO 674
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 674
atcccgatga gctaatggcg gta                                              23

<210> SEQ ID NO 675
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 675
tcccgatgag ctaatggcgg tat                                              23

<210> SEQ ID NO 676
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 676
cccgatgagc taatggcggt atg                                              23

<210> SEQ ID NO 677
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 677
ccgatgagct aatggcggta tgt                                              23

<210> SEQ ID NO 678
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 678
cgatgagcta atggcggtat gtg                                              23
```

<210> SEQ ID NO 679
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 679
gatgagctaa tggcggtatg tga                                              23

<210> SEQ ID NO 680
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 680
atgagctaat ggcggtatgt gat                                              23

<210> SEQ ID NO 681
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 681
tgagctaatg gcggtatgtg atg                                              23

<210> SEQ ID NO 682
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 682
gagctaatgg cggtatgtga tgg                                              23

<210> SEQ ID NO 683
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 683
agctaatggc ggtatgtgat ggt                                              23

<210> SEQ ID NO 684
<211> LENGTH: 23
<212> TYPE: DNA
<213> ORGANISM: Artificial Sequence
<220> FEATURE:
<223> OTHER INFORMATION: Primer/Probe/Quencher Sequence

<400> SEQUENCE: 684
gctaatggcg gtatgtgatg gtg                                              23

<210> SEQ ID NO 685
<211> LENGTH: 17
<212> TYPE: DNA
<213> ORGANISM: Artificial Sequence
<220> FEATURE:

<223> OTHER INFORMATION: Primer/Probe/Quencher Sequence

<400> SEQUENCE: 685
tgagctaatg gcggtat                                                        17

<210> SEQ ID NO 686
<211> LENGTH: 493
<212> TYPE: DNA
<213> ORGANISM: Artificial Sequence
<220> FEATURE:
<223> OTHER INFORMATION: Hybridization/Amplification Target Region

<400> SEQUENCE: 686
ttttctttgt tatcttttca gttaatgtgg tggcgaagga atttaccttga gacttctcga        60 ctgcaaagac gtatgtagat tcgctgaatg tcattcgctc tgcaataggt actccattac       120
agactatttc atcaggaggt acgtctttac tgatgattga tagtggcaca ggggataatt       180
tgtttgcagt tgatgtcaga gggatagatc cagaggaagg gcggtttaat aatctacggc       240
ttattgttga acgaaataat ttatatgtga caggatttgt taacaggaca aataatgttt       300
tttatcgctt tgctgatttt tcacatgtta cctttccagg tacaacagcg gttacattgt       360
ctggtgacag tagctatacc acgttacagc gtgttgcagg gatcagtcgt acggggatgc       420
agataaatcg ccattcgttg actacttctt atctggatt aatgtcgcat agtggaacct       480
cactgacgca gtc                                                          493

<210> SEQ ID NO 687
<211> LENGTH: 546
<212> TYPE: DNA
<213> ORGANISM: Artificial Sequence
<220> FEATURE:
<223> OTHER INFORMATION: Hybridization/Amplification Target Region

<400> SEQUENCE: 687
gttattaacc acaccccgcc gggcagttat tttgctgtgg atatacgagg gcttgatgtc        60
tatcaggcgc gttttgacca tcttcgtctg attattgagc aaaataattt atatgtggcc       120
gggttcgtta atacggcaac aaatactttc taccgttttt cagattttac acatatatca       180
gtgcccgatg tgacaacggt ttccatgaca acggacagca gttataccac tctgcaacgt       240
gtcgcagcgc tggaacgttc cggaatgcaa atcagtcgtc actcactggt ttcatcatat       300
ctggcgttaa tggagttcag tggtaataca atgaccagag atgcatccag agcagttctg       360
cgttttgtca ctgtcacggc agaagcctta cgcttcaggc agatacagag agaatttcgt       420
caggcactgt ctgaaactgc tcctgtgtat acgatgacgc cgggagacgt ggacctcact       480
ctgaactggg ggcgaatcag caatgtgctt ccggagtatc ggggagagga tggtgtcaga       540
gtgggg                                                                  546

<210> SEQ ID NO 688
<211> LENGTH: 212
<212> TYPE: DNA
<213> ORGANISM: Artificial Sequence
<220> FEATURE:
<223> OTHER INFORMATION: Hybridization/Amplification Target Region

<400> SEQUENCE: 688
ttgcaggcct ggttacaaca ttatggaacg gcagaggtta atctgcagag tggtaataac        60
tttgacggta gttcactgga cttcttatta ccgttctatg attccgaaaa catgctggca       120
tttggtcagg tcggtgcgcg ttacattgac tcccgcttta cggcaaattt aggtgctggc       180
cagcgttttt tccttcctga aaatatgttg gg 212

<210> SEQ ID NO 689
<211> LENGTH: 538
<212> TYPE: DNA
<213> ORGANISM: Artificial Sequence
<220> FEATURE:
<223> OTHER INFORMATION: Hybridization/Amplification Target Region

<400> SEQUENCE: 689
gttatcatct gtttattgct aatatatttg ttattctata cagaaatagt aatattatta 60
ttcttggcac tcttgcttcg cctgttgcaa cgtctctgta cgcgacggca gagaaaatta 120
ttaaatgtat tcagtctata gcaaccccgt taaatcaata ctatttcacg aggttgataa 180
agcaacatga attgaaatta gaaccataca aagttggaga atataaaagc ctgctatatg 240
caagcacaaa tattcagcta aagttcatgg ttttcattgt cctgagttta ggggggtgg 300
gtactatatt gggatataag gttcaaagta tcgctgaaat tagaagcgcg ttcatccctt 360
tatcaataat gtcttttgca atatttatgg ggatatacaa ttttatgttt ggttcggttg 420
gattgtccat aagagggtat aaaaaagaat tttcttatat agtggccatt acgggtgttt 480
caactattat tttatcatta tgcctgagtt atttctttgc tgaaataggc gctgcaat 538

<210> SEQ ID NO 690
<211> LENGTH: 343
<212> TYPE: DNA
<213> ORGANISM: Artificial Sequence
<220> FEATURE:
<223> OTHER INFORMATION: Hybridization/Amplification Target Region

<400> SEQUENCE: 690
gaatggtgaa tatttatttg gtcttaggaa taatcgaccg gccaaaaatt atttttttgt 60
tccaggtggt aggattcgca aaaatgaatc tattaaaaat gcttttaaaa gaatatcatc 120
tatggaatta ggtaaagagt atggtatttc aggaagtgtt tttaatggtg tatgggaaca 180
tttctatgat gatggttttt tttctgaagg cgaggcaaca cattatatag tgctttgtta 240
cacactgaaa gttcttaaaa gtgaattgaa tctcccagat gatcaacatc gtgaatacct 300
ttggctaact aaacaccaaa taaatgctaa acaagatgtt cat 343

<210> SEQ ID NO 691
<211> LENGTH: 272
<212> TYPE: DNA
<213> ORGANISM: Artificial Sequence
<220> FEATURE:
<223> OTHER INFORMATION: Hybridization/Amplification Target Region

<400> SEQUENCE: 691
catatggatt aattggcttt tttactatgc ttcaggcgct gtttggtctc ttagacttag 60
ggctaactcc aacaattggt cgtgaaacag ctcgctatca tggcgggaca atgacagtgc 120
tggactacag aaaattgcta agaactcttc atattttgtt cttcactatc gctactattg 180
gtggagtatt tctattttc ttagcaccca tcatttcggt tcattggtta aaggttacaa 240
caatatcaat tgacaccgta aattactgtg ta 272

<210> SEQ ID NO 692
<211> LENGTH: 305
<212> TYPE: DNA
<213> ORGANISM: Artificial Sequence
<220> FEATURE:

<223> OTHER INFORMATION: Hybridization/Amplification Target Region

<400> SEQUENCE: 692

```
catctaacat aaataccaca atgagcaacg tgattatatt acgtctggct gcagggactt      60
tcgttgcgtt gtgcatggtg gcatggggat ttttgctgc aagtgggctg tccagacagt     120
tcatagttgg tttggccata tctgtcgcat tacgagaaac tttcatcgtt ggtttaacat    180
ggtatcaaag ccaggctcgt ctcaaattac cttgtctggt acttatgtta gctgcaataa    240
ttaaactcat tgttatttat attggtttaa ggaatcagtt gccaataaat tatctttggg    300
tagca                                                                305
```

<210> SEQ ID NO 693
<211> LENGTH: 256
<212> TYPE: DNA
<213> ORGANISM: Artificial Sequence
<220> FEATURE:
<223> OTHER INFORMATION: Hybridization/Amplification Target Region

<400> SEQUENCE: 693

```
agtttgatcg tgtttatctg gaaggtaaaa tttccggaga aatgtattca aactatgcag      60
cagcacttca attggtcgat aactggtatg caatatgtat tctgtttgtc caggcaattg     120
caccattttt tatatttaaa ttcattgata taataaatat taaagaaaa ttgccttttt      180
gtgttttcgc tacacttgca gtaacctgca cgggcgcatt atttacaaca gttcttgcag    240
acatgatcat tcatat                                                    256
```

<210> SEQ ID NO 694
<211> LENGTH: 289
<212> TYPE: DNA
<213> ORGANISM: Artificial Sequence
<220> FEATURE:
<223> OTHER INFORMATION: Hybridization/Amplification Target Region

<400> SEQUENCE: 694

```
actcctcggc ataacattac tcagatgaaa aattactttt atatgggggt gattggagcg      60
ttaactggac ctatttcgat gatagttgtt cgaactattc tcactaataa ttttctttta    120
gaggatgccg atattggca agctgtaaat agaatttctg aggcttatct ggctgttctt     180
actacggcat tgacagttta ttattttcca aaaactgcag ccgcaagaag atatagcgaa    240
tatataactc ttttaaagac cggggcttgt attgttgtac cgctcgcgt                289
```

<210> SEQ ID NO 695
<211> LENGTH: 236
<212> TYPE: DNA
<213> ORGANISM: Artificial Sequence
<220> FEATURE:
<223> OTHER INFORMATION: Hybridization/Amplification Target Region

<400> SEQUENCE: 695

```
tgtgcttgga gtggcttata ttttaaataa aaaaaaacaa agcgatatta caaactggga      60
ttggacgtgg ataaaaaaag gtataaagct gtctgtacca atgctaattg cagcccttgc    120
actacgaggc ttttttcacgt tgatagatt cgcggtagaa aaaatatcgg gcctagaagt     180
tttgggagga tatacattat ttgttagtat gacttcagct attcaatcat ttttgg        236
```

<210> SEQ ID NO 696
<211> LENGTH: 280
<212> TYPE: DNA
<213> ORGANISM: Artificial Sequence
<220> FEATURE:
<223> OTHER INFORMATION: Hybridization/Amplification Target Region

<400> SEQUENCE: 696
tcggagactc gaaccccgcg aaaccagctt cgaaggctgg cgttctatcc cgatgagcta    60
atggcggtat gtgatggtgg cccttgctgg atttgaacca gcggcctggc gattatgagt   120
cgctcgctct caccactgag ctaaagggcc gggcgcagga taataacgtt acgaaatcaa   180
tgttgcaagc attcaagaat cacctggtta aaaattaccc ttgcttcctc caccagcgca   240
ttcaccatgt ctatccgaga taagtggcac aaaaaaaccc                         280

<210> SEQ ID NO 697
<211> LENGTH: 26
<212> TYPE: DNA
<213> ORGANISM: Artificial Sequence
<220> FEATURE:
<223> OTHER INFORMATION: Primer/Probe/Quencher Sequence

<400> SEQUENCE: 697
tatttacacc acaaaggaaa aagctg                                         26

<210> SEQ ID NO 698
<211> LENGTH: 33
<212> TYPE: DNA
<213> ORGANISM: Artificial Sequence
<220> FEATURE:
<223> OTHER INFORMATION: Primer/Probe/Quencher Sequence

<400> SEQUENCE: 698
ctttgctatt tacaccacaa aggaaaaagc tgc                                 33

<210> SEQ ID NO 699
<211> LENGTH: 32
<212> TYPE: DNA
<213> ORGANISM: Artificial Sequence
<220> FEATURE:
<223> OTHER INFORMATION: Primer/Probe/Quencher Sequence

<400> SEQUENCE: 699
gaatattttt ccataatttt cttgtatagc ag                                  32

<210> SEQ ID NO 700
<211> LENGTH: 29
<212> TYPE: DNA
<213> ORGANISM: Artificial Sequence
<220> FEATURE:
<223> OTHER INFORMATION: Primer/Probe/Quencher Sequence

<400> SEQUENCE: 700
aatagcagac actctatgcc tgtgtggag                                      29